US012670984B2

(12) United States Patent
Mizobe et al.

(10) Patent No.: US 12,670,984 B2
(45) Date of Patent: Jun. 30, 2026

(54) MEDICAL IMAGE PROCESSING APPARATUS, MEDICAL IMAGE PROCESSING METHOD AND COMPUTER-READABLE MEDIUM

(71) Applicant: CANON KABUSHIKI KAISHA, Tokyo (JP)

(72) Inventors: Hideaki Mizobe, Kanagawa (JP); Yoshihiko Iwase, Kanagawa (JP); Manabu Yamazoe, Tokyo (JP); Hiroki Uchida, Tokyo (JP); Ritsuya Tomita, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 240 days.

(21) Appl. No.: 18/731,570

(22) Filed: Jun. 3, 2024

(65) Prior Publication Data

US 2024/0321435 A1 Sep. 26, 2024

Related U.S. Application Data

(63) Continuation of application No. 17/120,718, filed on Dec. 14, 2020, now Pat. No. 12,040,079, which is a
(Continued)

(30) Foreign Application Priority Data

Jun. 15, 2018 (JP) ................................ 2018-114760
Oct. 10, 2018 (JP) ................................ 2018-192132
(Continued)

(51) Int. Cl.
*G16H 30/40* (2018.01)
*G06N 20/00* (2019.01)
(Continued)

(52) U.S. Cl.
CPC ............ *G16H 30/40* (2018.01); *G06N 20/00* (2019.01); *G06T 5/70* (2024.01); *G06T 7/0012* (2013.01);
(Continued)

(58) Field of Classification Search
CPC . G06T 2207/20081; G06T 2207/20084; G06T 2207/30168; G06T 7/0012;
(Continued)

(56) References Cited

U.S. PATENT DOCUMENTS 5,467,442 A 11/1995 Tsubota et al.
6,943,842 B2 9/2005 Stavely
(Continued)

FOREIGN PATENT DOCUMENTS

CA 3040419 A1 4/2018
CN 1735837 A 2/2006
(Continued)

OTHER PUBLICATIONS

Chinese Office Action issued by the China National Intellectual Property Administration on Nov. 12, 2024 in corresponding CN Patent Application No. 201980040325.3, with English translation.
(Continued)

*Primary Examiner* — Courtney Joan Nelson
(74) *Attorney, Agent, or Firm* — Carter, DeLuca & Farrell LLP

(57) ABSTRACT

A medical image processing apparatus includes: an obtaining unit configured to obtain a first image that is a medical image of a predetermined site of a subject; an image quality improving unit configured to generate, from the first image, a second image in which the image quality is improved compared to the first image by using an image quality improving engine that includes a machine learning engine; and a display controlling unit configured to cause a display
(Continued)

unit to display a composite image obtained by combining the first image and the second image according to a ratio obtained using information relating to at least a partial region of the first image.

16 Claims, 36 Drawing Sheets

Related U.S. Application Data continuation of application No. PCT/JP2019/023640, filed on Jun. 14, 2019.

(30) Foreign Application Priority Data

Mar. 11, 2019 (JP) ................................ 2019-044265
Mar. 29, 2019 (JP) ................................ 2019-068895

(51) Int. Cl.
*G06T 5/70* (2024.01)
*G06T 7/00* (2017.01)

(52) U.S. Cl.
CPC ............... *G06T 2207/20081* (2013.01); *G06T 2207/20182* (2013.01); *G06T 2207/30168* (2013.01)

(58) Field of Classification Search
CPC ..................... G06T 5/70; G06T 7/0002; G06T 2207/10101; G06T 2207/30041; G06T 5/00; G06T 3/4046; G06T 7/70; G06N 3/08; G06N 20/00; G06V 10/82; G06V 10/14; G06V 10/30; A61B 3/102; A61B 6/5258; A61B 8/5223; A61B 3/12; A61B 3/14; A61B 5/0066; A61B 5/7264; A61B 6/5217; A61B 8/5269; A61B 1/000096; A61B 8/10; G16H 30/40; G16H 30/20
See application file for complete search history.

(56) References Cited

U.S. PATENT DOCUMENTS 8,421,885 B2 * 4/2013 Kameyama ........... H04N 19/17 386/242
8,870,377 B2 10/2014 Iwase et al.
9,053,536 B2 6/2015 Imamura et al.
9,149,183 B2 10/2015 Iwase et al.
9,265,418 B2 2/2016 Iwase
9,330,233 B2 * 5/2016 Bhatia .................... G16H 30/20
9,436,994 B2 9/2016 Furukawa et al.
9,439,562 B2 9/2016 Natsuhori et al.
9,566,002 B2 2/2017 Nakahara et al.
9,741,098 B2 8/2017 Cox
9,824,273 B2 11/2017 Iwase et al.
10,010,249 B1 7/2018 Sadda
10,482,326 B2 11/2019 Iwase et al.
10,529,045 B2 1/2020 Iwase et al.
10,552,672 B2 2/2020 Iwase et al.
10,588,505 B2 3/2020 Natsuhori et al.
10,872,237 B2 12/2020 Iwase et al.
11,935,241 B2 3/2024 Tomita
2009/0097728 A1 4/2009 Lee
2011/0091128 A1 4/2011 Jeon
2012/0007863 A1 1/2012 Endo
2012/0200747 A1 8/2012 Higuchi
2012/0287401 A1 11/2012 Bizios
2013/0136326 A1 5/2013 Iwase et al.
2013/0195340 A1 8/2013 Iwase et al.
2014/0232899 A1 8/2014 Ootsuki et al.
2016/0063720 A1 3/2016 Han
2017/0154413 A1 6/2017 Yu et al.
2017/0252002 A1 9/2017 Mine et al.
2018/0012359 A1 1/2018 Prentasic
2018/0018757 A1 1/2018 Suzuki
2018/0122077 A1 5/2018 Wada
2018/0137605 A1 5/2018 Otsuka et al.
2018/0144447 A1 5/2018 Tate et al.
2018/0153395 A1 6/2018 Goto
2018/0199807 A1 7/2018 Ohta
2018/0214087 A1 8/2018 Balaji et al.
2021/0104313 A1 4/2021 Mizobe et al.
2021/0158525 A1 5/2021 Iwase et al.
2021/0183019 A1 6/2021 Uchida et al.
2021/0304363 A1 9/2021 Uchida
2021/0390696 A1 12/2021 Yamazoe

FOREIGN PATENT DOCUMENTS

CN 102802505 A 11/2012
CN 103096785 A 5/2013
CN 104080400 A 10/2014
CN 104471389 A 3/2015
CN 106157297 A 11/2016
CN 107157512 A 9/2017
EP 3417401 A1 12/2018
JP H01-170438 A 7/1989
JP H06180569 A 6/1994
JP H11-031214 A 2/1999
JP 2001-014444 A 1/2001
JP 2008-119195 A 5/2008
JP 2010-164351 A 7/2010
JP 2011-013334 A 1/2011
JP 2011-171843 A 9/2011
JP 2011-200635 A 10/2011
JP 2012-045298 A 3/2012
JP 2013090194 A 5/2013
JP 2014002497 A 1/2014
JP 2014-229115 A 12/2014
JP 2015-009126 A 1/2015
JP 2015129987 A 7/2015
JP 2015-160105 A 9/2015
JP 2015171437 A 10/2015
JP 2015198757 A 11/2015
JP 2016-209147 A 12/2016
JP 2017-047113 A 3/2017
JP 2017094097 A 6/2017
JP 2017-158687 A 9/2017
JP 2017-158962 A 9/2017
JP 2017159027 A 9/2017
JP 2017-189608 A 10/2017
JP 2017-221555 A 12/2017
JP 2018-007078 A 1/2018
JP 2018005841 A 1/2018
JP 2018033717 A 3/2018
JP 2018055516 A 4/2018
JP 2018068748 A 5/2018
JP 2018077786 A 5/2018
JP 2018084982 A 5/2018
JP 2018-089301 A 6/2018
JP 2018089160 A 6/2018
JP 2018114068 A 7/2018
JP 2018121885 A 8/2018
JP 2018-138159 A 9/2018
JP 2018-153611 A 10/2018
JP 2019025044 A 2/2019
WO 2009107770 A1 9/2009
WO 2010050333 A1 5/2010
WO 2012-092132 A2 7/2012
WO 2013057932 A1 4/2013
WO 2014203901 A1 12/2014
WO 2017030276 A2 2/2017
WO 2017143300 A1 8/2017
WO 2017-155015 A1 9/2017
WO 2018210978 A1 11/2018

OTHER PUBLICATIONS

Notice of Reasons for Refusal issued by the Japanese Patent Office on Feb. 12, 2026 in corresponding JP Patent Application No. 2025-022210.

(56) References Cited

OTHER PUBLICATIONS

Notice of Reasons for Refusal issued by the Japanese Patent Office on Aug. 20, 2024 in corresponding JP Patent Application No. 2023-208259, with English translation.
Chinese Notification to Grant issued by the China National Intellectual Property Administration on Jul. 11, 2024 in corresponding CN Patent Application No. 201980093820.0, with English translation.
Chinese Office Action issued by the China National Intellectual Property Administration on Jul. 4, 2024 in corresponding CN Patent Application No. 201980093906.3, with English translation.
Notice of Reasons for Refusal issued by the Japanese Patent Office on Jan. 31, 2023 in corresponding JP Patent Application No. 2019-183346, with English translation.
Combined Search and Examination Report issued by the Great Britain Patent Office on Dec. 21, 2022 in corresponding GB Patent Application No. GB2215912.3.
Notice of Reasons for Refusal issued by the Japanese Patent Office on Sep. 13, 2022 in corresponding JP Patent Application No. 2018-192132, with English translation.
Office Action issued by the Korean Patent Office on Jun. 27, 2022 in corresponding KR Patent Application No. 10-2021-7000477.
Examination Report issued by the Intellectual Property Office of GB on Mar. 1, 2022 in corresponding GB Patent Application No. 2019907.1.
Notice of Reasons for Refusal issued by the Japan Patent Office on Feb. 1, 2022 in corresponding JP Patent Application No. 2018-192132, with English translation.
Notice of Reasons for Refusal issued by the Japan Patent Office on Jan. 20, 2022 in corresponding JP Patent Application No. 2018-114760, with English translation.
Examination Report issued by the Intellectual Property Office of India on Jan. 7, 2022 in corresponding IN Patent Application No. 202147000592, with English translation.
Office Action issued by the Chinese Patent Office on Jul. 25, 2023 in corresponding CN Patent Application No. 201980093820.0, with partial English translation.
Chinese Office Action issued in corresponding CN Patent Application No. 201980057669.5, dated Jan. 4, 2024, with English translation.
Notice of Reasons for Refusal issued by the Japanese Patent Office on Nov. 28, 2023 in corresponding JP Patent Application No. 2022-197060, with English translation.
Chinese Office Action issued in corresponding CN Patent Application No. 201980040325.3, dated Sep. 26, 2023, with English translation.
Chinese Office Action issued in corresponding CN Patent Application No. 201980093906.3, dated Sep. 27, 2023, with English translation.
Chinese Office Action issued in corresponding CN Patent Application No. 201980040325.3, dated Mar. 20, 2024, with English translation.
Chinese Office Action issued in corresponding CN Patent Application No. 201980066871.4, dated Jan. 8, 2024, with English translation.
Notice of Reasons for Refusal issued by the Japanese Patent Office on Sep. 21, 2023 in corresponding JP Patent Application No. 2022-118982, with English translation.
Notice of Reasons for Refusal issued by the Japanese Patent Office on Aug. 1, 2023 in corresponding JP Patent Application No. 2022-197060, with English translation.
Notice of Reasons for Refusal issued by the Japanese Patent Office on Jul. 11, 2023 in corresponding JP Patent Application No. 2022-118982, with English translation.
Hasegawa, "AI, noise reduction treatment PixelShine" INNERVISION (Jun. 2017) pp. 31-34, vol. 32, No. 7, with English abstract.
Notice of Reasons for Refusal issued by the Japanese Patent Office on May 23, 2023 in corresponding JP Patent Application No. 2019-183351, with English translation.
Kurihara, S. et al., "Amomaly Detection of Fundus Image Using Image Completion", Proceedings of Workshop of the Institute of Electrical Engineers of Japan (Sep. 2018) pp. 105-109, with English Abstract.
Notice of Reasons for Refusal issued by the Japanese Patent Office on May 30, 2023 in corresponding JP Patent Application No. 2019-183348, with English translation.
International Search Report issued by the Japan Patent Office on Feb. 4, 2020 in corresponding International Application No. PCT/JP2019/045301, with English translation.
International Preliminary Report on Patentability issued on Apr. 8, 2021 by the International Bureau of WIPO on behalf of the Japan Patent Office acting as International Searching Authority in corresponding International Application No. PCT/JP2019/023657, with English translation.
International Search Report issued on Aug. 13, 2019 by the Japan Patent Office acting as International Searching Authority in corresponding International Application No. PCT/JP2019023657, with English translation.
International Preliminary Report on Patentability issued on Mar. 9, 2021 by the International Bureau on behalf of the Japan Patent Office acting as International Searching Authority in corresponding International Application No. PCT/JP2019/023650, with English translation.
International Preliminary Report on Patentability issued on Dec. 15, 2020 by the International Bureau on behalf of the Japan Patent Office acting as International Searching Authority in corresponding International Application No. PCT/JP2019/023640, with English translation.
Devalla Sripad Krishna, A Deep Learning Approach to Denoise Optical Coherence Tomography Images of the Optic Nerve Head, [online], Sep. 27, 2018, [retrieved on Aug. 19, 2019], Retrieved from the Internet: <URL: https://arxiv.org/pdf/1809.10589v1.pdf>.
Devalla Sripad Krishna, DRUNET: A Dliated-Residual U-Net Deep Learning Network to Digitally Strain Optic Nerve Head Tissues in Optical Coherence Tomography Images, [online], Mar. 1, 2018, [retrieved on Aug. 19, 2019], Retrieved from the Internet: <URL: https://arxiv.org/pdf/1803.00232v1.pdf>.
Sheet Debdoot, Deep Learning of Tissue Specific Speckle Representations in Optical Coherence Tomography and Deeper Exploration for in Situ Histology, 2015 IEEE 12th International Symposium on Biomedical Imaging (ISBI), Apr. 2015, pp. 777-780.
International Search Report issued in International Application No. PCT/JP2019/023650 dated Sep. 3, 2019, pp. 1-2, English Translation.
International Search Report issued in International Application No. PCT/JP2019/023640 dated Sep. 3, 2019, pp. 1-2.
F. Russo, "An image enhancement technique combining sharpening and noise reduction," IMTC 2001. Proceedings of the 18th IEEE Instrumentation and Measurement Technology Conference. Rediscovering Measurement in the Age of Informatics (Cat. No .01CH 37188), Budapest, Hungary, 2001, pp. 1921-1924 vol. 3 (Year: 2021).
T. Wang, M. Sun and K. Hu, "Dilated Deep Residual Network for Image Denoising," 2017 IEEE 29th International Conference on Tools with Artificial Intelligence (ICTAI), Boston, MA, USA, 2017, pp. 1272-1279, doi: 10.1109/ICTAI.2017.00192 (Year: 2017).
Duan, Jinming, et al. "Automated Segmentation of Retinal Layers from Optical Coherent Tomography Images Using Geodesic Distance." arXiv.Org, Sep. 7, 2016, arxiv.org/abs/1609.02214. (Year: 2016).
Chinese Office Action issued by the China National Intellectual Property Administration on Mar. 11, 2025 in corresponding CN Patent Application No. 201980066871.4, with English translation.

* cited by examiner

MEDICAL IMAGE PROCESSING APPARATUS, MEDICAL IMAGE PROCESSING METHOD AND COMPUTER-READABLE MEDIUM

CROSS-REFERENCE TO RELATED APPLICATIONS

This application is a Continuation U.S. patent application Ser. No. 17/120,718, filed on Dec. 14, 2020, which is a Continuation of International Patent Application No. PCT/JP2019/023640, filed Jun. 14, 2019, which claims the benefits of Japanese Patent Application No. 2018-114760, filed Jun. 15, 2018, Japanese Patent Application No. 2018-192132, filed Oct. 10, 2018, Japanese Patent Application No. 2019-044265, filed Mar. 11, 2019, and Japanese Patent Application No. 2019-068895, filed Mar. 29, 2019, all of which are hereby incorporated by reference herein in their entirety.

BACKGROUND OF THE INVENTION

Field of the Invention

The present invention relates to a medical image processing apparatus, a medical image processing method and a computer-readable medium.

Description of the Related Art

In the field of medical treatment, in order to identify a disease of a subject and observe the extent of the disease, images are acquired by various kinds of imaging apparatuses, and an image diagnosis is performed by a medical professional. The different kinds of imaging apparatuses include, for example, in the field of radiology, an X-ray imaging apparatus, an X-ray computed tomography (CT) apparatus, a magnetic resonance imaging (MRI) apparatus, a positron emission tomography (PET) apparatus, and a single photon-emission computed tomography (SPECT) apparatus. Further, for example, in the field of ophthalmology, the different kinds of imaging apparatuses include a fundus camera, a scanning laser ophthalmoscope (SLO), an optical coherence tomography (OCT) apparatus and an OCT angiography (OCTA) apparatus.

In order to perform an image diagnosis accurately and to complete the image diagnosis in a short time, the level of quality of an image acquired by an imaging apparatus is important, namely, it is important for the image to have a low amount of noise, high resolution and spatial resolution, and appropriate gradation. Further, an image in which a site or a lesion which it is desired to observe is enhanced may also be useful in some cases.

However, with many imaging apparatuses, it is necessary to pay some kind of price in order to obtain an image that is suitable for image diagnosis, such as an image that has high image quality. For example, although one method is to purchase a high-performance imaging apparatus in order to obtain an image that has high image quality, in most cases a larger investment is required in comparison to purchasing a low-performance imaging apparatus.

Further, for example, when using CT, in order to obtain an image with less noise, it is sometimes necessary to increase the amount of radiation that the subject is exposed to. Furthermore, for example, when using MRI, in some cases a contrast medium for which there is a risk of side effects is used in order to obtain an image in which a site which it is desired to observe is enhanced. In addition, for example, when using OCT, when it is necessary to widen a region to be imaged or to obtain a high spatial resolution, in some cases the imaging time becomes long. Further, for example, with some imaging apparatuses it is necessary to acquire an image multiple times in order to obtain an image that has high image quality, and the time required to perform imaging increases accordingly.

Japanese Patent Application Laid-Open No. 2018-5841 discloses technology that, in order to respond to the rapid advances being made in medical techniques and also to correspond to simple imaging in an emergency, converts a previously acquired image into an image with higher resolution by means of an artificial intelligence engine. According to this technology, for example, an image that is acquired by simple imaging with less of a cost can be converted into an image with a higher resolution.

However, even when an image has a high resolution, there are cases in which it cannot be said that the image is an image that is suitable for image diagnosis. For example, even when the resolution of an image is high, if there is a large amount of noise or the contrast is low or the like in the image, in some cases an object that should be observed cannot be appropriately ascertained.

In this regard, one objective of the present invention is to provide a medical image processing apparatus, a medical image processing method and a computer-readable medium having stored thereon a program, which can generate an image that is more suitable for image diagnosis than in the conventional technology.

SUMMARY OF THE INVENTION

A medical image processing apparatus according to one embodiment of the present invention includes: an obtaining unit configured to obtain a first image that is a medical image of a predetermined site of a subject; an image quality improving unit configured to generate, from the first image, a second image in which image quality is improved compared to the first image, using an image quality improving engine including a machine learning engine; and a display controlling unit configured to cause a composite image obtained by combining the first image and the second image according to a ratio obtained using information relating to at least a partial region of the first image to be displayed on a display unit.

Further, a medical image processing method according to another embodiment of the present invention includes: obtaining a first image that is a medical image of a predetermined site of a subject; generating, from the first image, a second image in which image quality is improved compared to the first image, using an image quality improving engine including a machine learning engine; and causing a composite image obtained by combining the first image and the second image according to a ratio obtained using information relating to at least a partial region of the first image to be displayed on a display unit.

Further features of the present invention will become apparent from the following description of exemplary embodiments with reference to the attached drawings.

DESCRIPTION OF THE EMBODIMENTS

Figure 1:
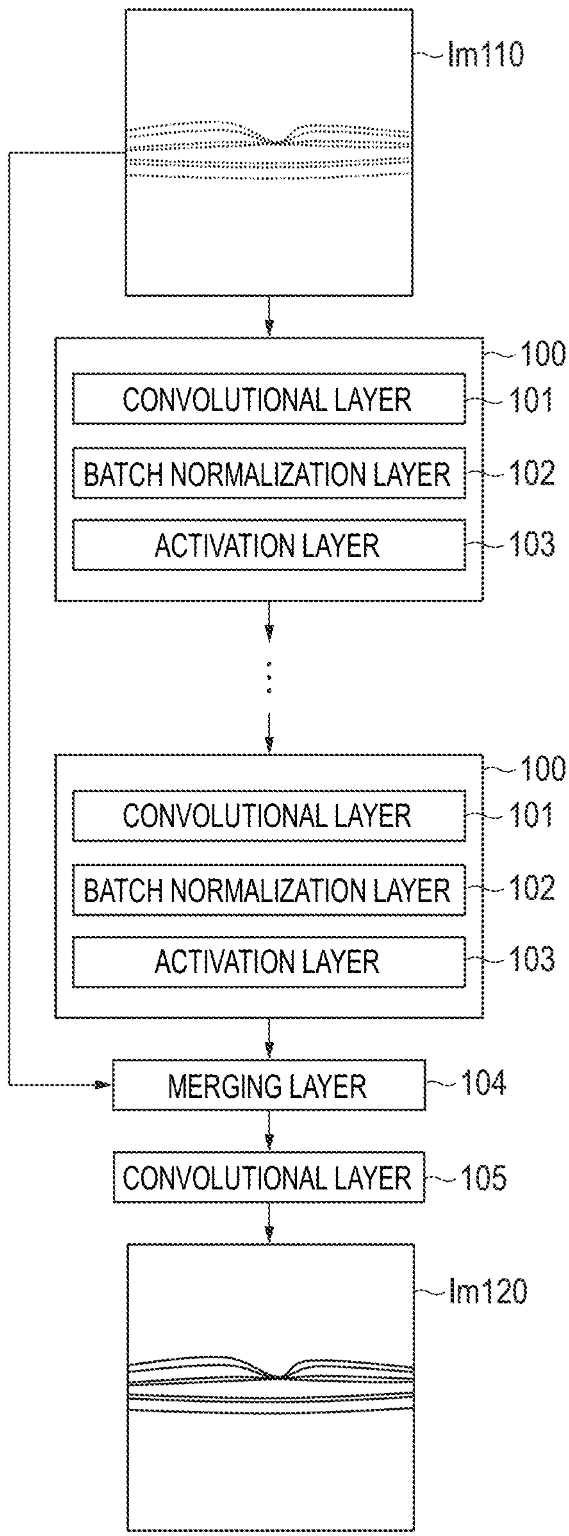
FIG. 1 is a view illustrating an example of a configuration of a neural network relating to image quality improving processing.

Exemplary embodiments of the present invention will now be described in detail in accordance with the accompanying drawings. However, the dimensions, materials, shapes and relative positions of the components described in the following embodiments are not determinate, and can be changed according to a configuration of an apparatus to which the present invention is applied or to various conditions. Further, identical or functionally similar elements are denoted by the same reference numerals in different drawings.

Explanation of Terms

First, terms used in the present description will be described.

In a network described in the present description, respective apparatuses may be connected using wired or wireless connections. Here, the types of connections that connect each apparatus in the network include, for example, a dedicated line, a local area network (hereunder, described as "LAN") connection, a wireless LAN connection, an Internet connection, Wi-Fi (registered trademark) and Bluetooth (registered trademark).

A medical image processing apparatus may be constituted by two or more apparatuses which are capable of communicating with each other, or may be constituted by a single apparatus. Further, the respective components of a medical image processing apparatus may be implemented by a software module that is executed by a processor such as a CPU (central processing unit) or an MPU (micro processing unit). Further, the respective components may be implemented by a circuit or the like that serves a specific function such as an ASIC. Furthermore, the respective components may be implemented by a combination of any other hardware or any software.

Medical images to be processed by a medical image processing apparatus or a medical image processing method according to embodiments described hereinafter include images obtained using an arbitrary modality (imaging apparatus or imaging method). The medical images to be processed can include a medical image obtained by any imaging apparatus or the like, and images created by a medical image processing apparatus or a medical image processing method in accordance with embodiments that are described hereinafter.

In addition, a medical image to be processed is an image of a predetermined site of a subject (examinee), and the image of the predetermined site includes at least one part of the predetermined site of the subject. The medical image may also include another site of the subject. The medical image may be a still image or a moving image, and may be a black and white image or a color image. In addition, the medical image may be an image representing the structure (form) of the predetermined site or may be an image representing a function of the predetermined site. Images that represent a function include, for example, an image representing hemodynamics (blood flow volume, blood flow velocity or the like) such as an OCTA image, a Doppler OCT image, an fMRI image, and an ultrasound Doppler image. Note that, the predetermined site of the subject may be determined according to the imaging target, and such predetermined sites include organs such as the human eye (eye to be examined), brain, lung, intestine, heart, pancreas, kidney, and liver, and any sites such as the head, chest, legs and arms.

Further, the medical image may be a tomographic image of the subject, or may be a front image. Examples of a front image include a front image of the ocular fundus, a front image of the anterior ocular segment, a fundus image obtained by fluorescence imaging, and an en-face image generated using at least a partial range of data in the depth direction of the imaging target with respect to data obtained by OCT (three-dimensional OCT data). Note that, an en-face image may be an OCTA en-face image (motion contrast front image) generated using at least a partial range of data in the depth direction of the imaging target with respect to three-dimensional OCTA data (three-dimensional motion contrast data). Further, three-dimensional OCT data or three-dimensional motion contrast data is an example of three-dimensional medical image data.

In addition, the term "imaging apparatus" refers to an apparatus for performing imaging to obtain an image to be used for diagnosis. Examples of an imaging apparatus include an apparatus that obtains an image of a predetermined site of the subject by irradiating the predetermined site with light, radioactive rays such as X-rays, electromagnetic waves, or ultrasonic waves or the like, and an apparatus that obtains an image of a predetermined site by detecting radioactive rays emitted from the subject. More specifically, examples of an imaging apparatus according to the embodiments described hereinafter include, at least, an X-ray imaging apparatus, a CT apparatus, an MRI apparatus, a PET apparatus, a SPECT apparatus, an SLO apparatus, an OCT apparatus, an OCTA apparatus, a fundus camera and an endoscope.

Note that, a time domain OCT (TD-OCT) apparatus and a Fourier domain OCT (FD-OCT) apparatus may be included as examples of an OCT apparatus. Further, examples of a Fourier domain OCT apparatus may include a spectral domain OCT (SD-OCT) apparatus and a swept source OCT (SS-OCT) apparatus. Further, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-SLO) apparatus and a polarization-sensitive OCT (PS-OCT) apparatus and the like for visualizing information relating to polarization phase differences or depolarization may be included as examples of an SLO apparatus or an OCT apparatus, respectively.

The term "image management system" refers to an apparatus and a system which receive and store images that were imaged by an imaging apparatus and images that were subjected to image processing. An image management system can also transmit an image in response to a request from a connected apparatus, perform image processing on a stored image, and request another apparatus to carry out a request for image processing. Examples of an image management system include a picture archiving and communication system (PACS). In particular, an image management system according to embodiments that are described hereinafter includes a database that is also capable of storing, together with a received image, various kinds of information such as information pertaining to the subject and the imaging time which is associated with the image. Further, the image management system is connected to a network and, in response to a request from another apparatus, can transmit and receive images, convert images, and transmit and receive various kinds of information associated with stored images.

The term "imaging conditions" refers to various kinds of information pertaining to the conditions when imaging of an image obtained by an imaging apparatus. The imaging conditions include, for example, information relating to the imaging apparatus, information relating to the facility where imaging was performed, information regarding an examination pertaining to the imaging, information relating to the person performing the imaging, and information relating to the subject. The imaging conditions also include, for example, the imaging date and time, an imaged site name, an imaged region, an imaging angle of view, an imaging system, an image resolution and gradation, an image size, an applied image filter, information regarding the image data format, and information regarding the amount of radiation. Note that, examples of the imaged region can include a peripheral region that deviates from a specific imaged site, and a region which includes a plurality of imaged sites.

The imaging conditions can be stored in a data structure constituting the image, can be stored as imaging conditions data that is separate from the image, or can be stored in a database or image management system that is associated with the imaging apparatus. Therefore, imaging conditions can be obtained by procedures that correspond to the unit for storing the imaging conditions of the imaging apparatus. Specifically, the imaging conditions, for example, are obtained by analyzing the data structure of an image that is output by the imaging apparatus, acquiring imaging conditions data corresponding to the image, or accessing an interface for obtaining imaging conditions from a database associated with the imaging apparatus.

Note that, depending on the imaging apparatus, there may also be imaging conditions that cannot be obtained due to reasons such that the imaging conditions are not stored. Examples of such a case include a case where the imaging apparatus does not have a function for obtaining and storing specific imaging conditions, or a case where such a function has been disabled. Further, for example, there are also cases where an imaging condition is not stored because it is an imaging condition that is not related to the imaging apparatus or imaging. In addition, for example, there are also cases where an imaging condition is concealed, encrypted, or cannot be obtained without the right to obtain the imaging condition. However, there are cases where even an imaging condition that is not stored can be obtained. For example, an imaged site name or an imaged region can be identified by performing image analysis.

The term "machine learning model" refers to a model which, with respect to any machine learning algorithm, performed training (learning) using appropriate training data in advance. The training data is composed of one or more pair groups composed of input data and ground truth (correct answer data). Note that, the format and combination of the input data and ground truth of a pair group constituting the training data may be suited for a desired configuration, such as one of the pair may be an image and the other may be a numerical value, or one of the pair may be constituted by a plurality of images groups and the other may be a character string, or both elements of the pair may be images.

Specifically, an example of training data may include training data (hereinafter, referred to as "first training data") composed of a pair group in which each pair includes an image obtained by OCT and an imaged site label corresponding to the relevant image. Note that, the imaged site label is a unique numerical value or a character string representing a site. Further, an example of other training data may include training data (hereinafter, referred to as "second training data") composed of a pair group in which each pair includes a low quality image with a large amount of noise that was obtained by normal OCT imaging, and a high quality image obtained by performing OCT imaging multiple times and performing image quality improving processing.

When input data is input to a machine learning model, output data in accordance with the design of the relevant machine learning model is output. The machine learning model, for example, in accordance with a tendency for which the machine learning model was trained using training data, outputs output data which has a high probability of corresponding to the input data. Further, the machine learning model, for example, can output a probability of corresponding to the input data as a numerical value with respect to each kind of output data, according to the tendency for which the machine learning model was trained using training data. Specifically, for example, when an image acquired by OCT is input to a machine learning model trained with the first training data, the machine learning model outputs an imaged site label of an imaged site that is imaged in the relevant image, or outputs a probability for each imaged site label. Further, for example, when a low quality image which has a large amount of noise obtained by normal OCT imaging is input to a machine learning model trained with the second training data, the machine learning model outputs a high quality image equivalent to an image obtained by performing imaging multiple times by OCT and performing image quality improving processing. Note that, with regard to the machine learning model, from the viewpoint of maintaining quality, the machine learning model can be configured so as not to use output data which the machine learning model itself output, as training data.

Further, machine learning algorithms include techniques relating to deep learning such as a convolutional neural network (CNN). In a technique relating to deep learning, if the settings of parameters with respect to a layer group and a node group constituting a neural network differ, in some cases the degrees to which a tendency trained using training data is reproducible in the output data will differ. For example, in a machine learning model of deep learning that uses the first training data, if more appropriate parameters are set, the probability of outputting a correct imaged site label may become higher. Further, for example, in a machine learning model of deep learning that uses the second training data, if more appropriate parameters are set, in some cases an image with higher image quality can be output.

Specifically, the parameters in the case of a CNN can include, for example, the kernel size of the filters, the number of filters, the value of a stride, and the dilation value which are set with respect to the convolutional layers, and also the number of nodes output from a fully connected layer. Note that, the parameter group and the number of training epochs can be set to values preferable for the utilization form of the machine learning model based on the training data. For example, based on the training data, a parameter group or a number of epochs can be set that enables the output of a correct imaged site label with a higher probability or the output of an image with higher image quality.

One method for determining such a parameter group or the number of epochs will now be described as an example. First, 70% of the pair groups constituting the training data is set for training use, and the remaining 30% is set at random for evaluation use. Next, training of the machine learning model is performed using the pair groups for training use, and at the end of each training epoch, a training evaluation value is calculated using the pair groups for evaluation use. The term "training evaluation value" refers to, for example, an average value of a group of values obtained by evaluating, by a loss function, the output when input data included in each pair is input to the machine learning model that is being trained, and the ground truth that corresponds to the input data. Finally, the parameter group and the number of epochs when the training evaluation value is smallest are determined as the parameter group and the number of epochs of the relevant machine learning model. Note that, by dividing a pair group constituting the training data into a pair group for training use and a pair group for evaluation use and determining the number of epochs in this way, the occurrence of a situation in which the machine learning model overlearns with respect to the pair group for training can be prevented.

The term "image quality improving engine (learned model for improving image quality)" refers to a module which outputs a high quality image obtained by improving image quality of a low quality image that was input. Here, the term "improving image quality" as used in the present description refers to converting an input image to an image with image quality that is more suitable for image diagnosis, and the term "high quality image" refers to an image that has been converted into an image with image quality that is more suitable for image diagnosis. Further, the term "low quality image" refers to an image obtained by imaging without setting any particular settings in order to obtain high image quality such as, for example, a two-dimensional image or three-dimensional image obtained by X-ray imaging, CT, MRI, OCT, PET, or SPECT, or a three-dimensional CT moving image obtained by serial imaging. Specifically, examples of a low quality image include an image obtained by an X-ray imaging apparatus or by imaging with a low amount of radiation by CT, an image obtained by imaging by MRI without using a contrast medium, an image obtained by OCT imaging that is short-time imaging, and an OCTA image obtained by performing imaging a small number of times.

Further, the content of image quality which is suitable for image diagnosis depends on what it is desired to diagnose using various kinds of image diagnosis. Therefore, while it is not possible to say so unconditionally, for example, image quality that is suitable for image diagnosis includes image quality in which the amount of noise is low, the contrast is high, the imaging target is displayed in colors and gradations which make the imaging target easy to observe, the image size is large and the resolution is high. In addition, image quality that is suitable for image diagnosis can include image quality such that objects or gradations which do not actually exist that were rendered during the process of image generation are removed from the image.

Furthermore, if a high quality image with a little noise and high contrast is utilized for image analysis such as blood vessel analysis processing of an OCTA image or the like, or region segmentation processing of a CT or OCT image or the like, in many cases analysis can be performed more accurately than if utilizing a low quality image. Therefore, a high quality image output by the image quality improving engine is sometimes useful for not only image diagnosis but also for image analysis.

In image processing techniques constituting image quality improving techniques in the embodiments described hereinafter, processing which uses various kinds of machine learning algorithms such as deep learning is performed. Note that, in the image processing techniques in question, in addition to processing which uses machine learning algorithms, any existing processing such as various kinds of image filter processing, matching processing using a database of high quality images corresponding to similar images, and knowledge-based image processing may be performed.

In particular, a configuration illustrated in FIG. 1 is available as an example of the configuration of a CNN that improves the image quality of a two-dimensional image. The configuration of the CNN includes a group of a plurality of convolutional processing blocks 100. Each convolutional processing block 100 includes a convolutional layer 101, a batch normalization layer 102, and an activation layer 103 that uses a rectifier linear unit. The configuration of the CNN also includes a merging layer 104 and a final convolutional layer 105. An output value group of the convolutional processing blocks 100 and a pixel value group that constitutes the relevant image are concatenated and added and merged by the merging layer 104. The final convolutional layer 105 outputs a pixel value group constituting a high quality image Im120 that was merged by the merging layer 104. In such a configuration, a value group obtained when the pixel value group constituting the input image Im110 is output after undergoing processing by the convolutional processing block 100 group, and a pixel value group constituting the input image Im110 are merged by the merging layer 104. Thereafter, the merged pixel value group is formed into a high quality image Im120 by the final convolutional layer 105.

Note that, for example, by setting the number of convolutional processing blocks 100 to 16 and, as the parameters of the convolutional layer 101 group, setting the kernel size of the filters to a width of three pixels and a height of three pixels, and the number of filters to 64, a certain image quality improving effect is obtained. However, in practice, as mentioned in the description of the aforementioned machine learning model, a better parameter group can be set by using training data corresponding to the utilization form of the machine learning model. Note that, in a case where it is necessary to process a three-dimensional image or a four-dimensional image, the kernel size of the filters may be extended to three dimensions or four dimensions.

Note that, when using some image processing techniques such as image processing using a CNN, it is necessary to pay attention to the image size. Specifically, it should be kept in mind that, to overcome a problem such as the image quality of a peripheral part of a high quality image not being sufficiently improved, in some cases different image sizes are required for a low quality image that is input and a high quality image that is output.

Although it is not specifically described in the embodiments described later in order to provide a clear description, in a case where an image quality improving engine is adopted that requires different image sizes for an image that is input to the image quality improvement engine and an image that is output therefrom, it is assumed that the image sizes are adjusted in an appropriate manner. Specifically, padding is performed with respect to an input image such as an image that is used in training data for training a machine learning model or an image to be input to an image quality improving engine, or imaging regions at the periphery of the relevant input image are joined together to thereby adjust the image size. Note that, a region which is subjected to padding is filled using a fixed pixel value, or is filled using a neighboring pixel value, or is mirror-padded, in accordance with the characteristics of the image quality improving technique so that image quality improving can be effectively performed.

Further, an image quality improving technique is sometimes performed using only one image processing technique, and is sometimes performed using a combination of two or more image processing techniques. In addition, there are also cases in which processing of a group of a plurality of high image quality techniques is carried out in parallel to generate a group of a plurality of high quality images, and a high quality image with the highest image quality is then finally selected as the high quality image. Note that, selection of a high quality image with the highest image quality may be automatically performed using image quality evaluation indexes, or may be performed by displaying a group of a plurality of high quality images on a user interface equipped with any display unit or the like so that selection can be performed according to an instruction of the examiner (user).

Note that, since there are also cases where an input image that has not been subjected to image quality improvement is suitable for image diagnosis, the input image may be added to the objects for selection of the final image. Further, parameters may be input into the image quality improving engine together with the low quality image. For example, a parameter specifying the degree to which to perform image quality improving, or a parameter specifying an image filter size to be used in an image processing technique may be input to the image quality improving engine together with the input image.

The term "imaging location estimating engine" refers to a module that estimates an imaged site or imaged region of an input image. The imaging location estimating engine can output the location of an imaged site or imaged region that is depicted in an input image, or for each imaged site label or imaged region label of a required detail level, can output a probability of being the relevant imaged site or imaged region.

In some cases, the imaged site or imaged region is not stored as an imaging condition by the imaging apparatus, or the imaging apparatus could not acquire and store the imaged site or imaged region. There are also cases where even though an imaged site or imaged region is stored, an imaged site or imaged region of a required detail level is not stored. For example, if only "posterior segment of eyeball" is stored as an imaged site, it may not be known if the detailed location of the imaged site is the "macular area", the "optic nerve head", or is the "macular area and optic nerve head", or is an "other area". Further, as another example, if only "breast" is stored as the imaged site, it may not be known whether, in more detail, this means "right breast", "left breast" or "both". Therefore, by using the imaging location estimating engine, the imaged site or imaged region of an input image in such cases can be estimated.

In the image and data processing techniques constituting the estimating method of the imaging location estimating engine, processing that uses various kinds of machine learning algorithms such as deep learning is performed. Note that, in the image and data processing techniques in question, in addition to or instead of processing using machine learning algorithms, any existing estimation processing such as natural language processing, matching processing using a database of similar images and similar data, and knowledge-based processing may be performed. Note that, images to which a label of an imaged site or imaged region is attached can be adopted as training data for training a machine learning model that was built using a machine learning algorithm. In this case, an image of the training data is used as input data, and a label of the imaged site or imaged region is used as ground truth.

Figure 2:
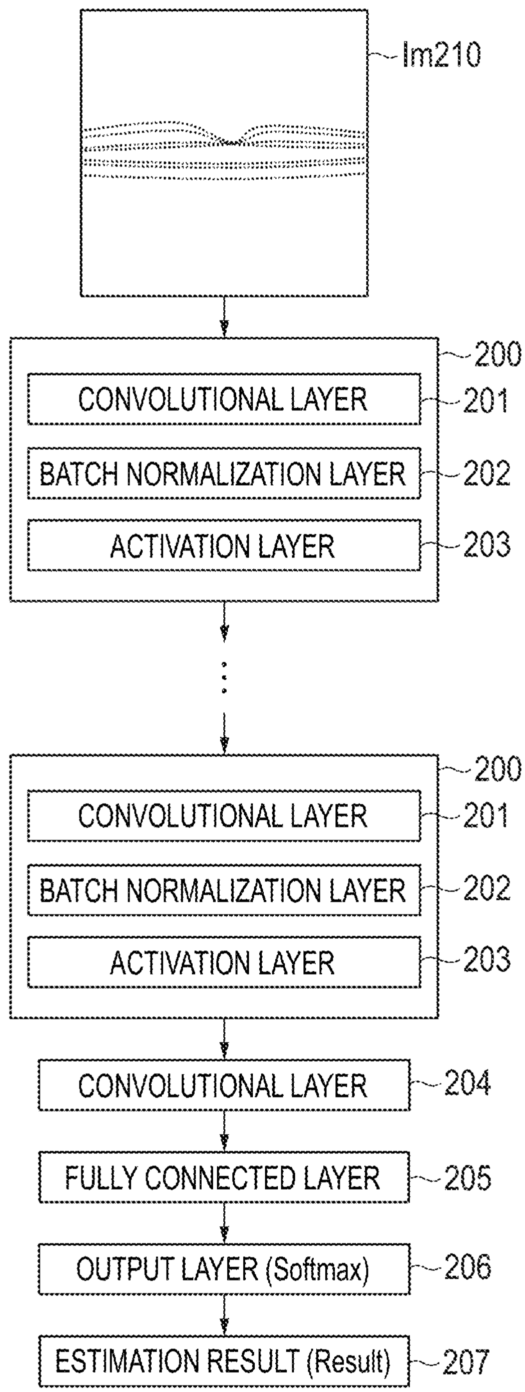
FIG. 2 is a view illustrating an example of a configuration of a neural network relating to imaging location estimation processing.

In particular, the configuration illustrated in FIG. 2 is available as an example of the configuration of a CNN that estimates the imaging location of a two-dimensional image. The configuration of the CNN includes a group of a plurality of convolutional processing blocks 200 which are each constituted by a convolutional layer 201, a batch normalization layer 202, and an activation layer 203 that uses a rectifier linear unit. The configuration of the CNN also includes a final convolutional layer 204, a fully connected layer 205, and an output layer 206. The fully connected layer 205 fully connects output value groups of the convolutional processing blocks 200. Further, the output layer 206 utilizes the softmax function to output the probability for each assumed imaged site label with respect to the input image Im210 as an estimation result (Result) 207. In such a configuration, for example, if the input image Im210 is an image obtained by imaging a "macular area", the highest probability is output for an imaged site label corresponding to "macular area".

Note that, for example, by setting the number of convolutional processing blocks 200 to 16, and, as the parameters of the convolutional layer 201 group, setting the kernel size of the filters to a width of three pixels and a height of three pixels, and the number of filters to 64, an imaged site can be estimated with a certain accuracy. However, in practice, as mentioned in the description of the aforementioned machine learning model, a better parameter group can be set by using training data corresponding to the utilization form of the machine learning model. Note that, in a case where it is necessary to process a three-dimensional image or a four-dimensional image, the kernel size of the filters may be extended to three dimensions or four dimensions. Note that, the estimating method is sometimes carried out using only one image and data processing technique, and is sometimes carried out using a combination of two or more image and data processing techniques.

The term "image quality evaluating engine" refers to a module that outputs an image quality evaluation index with respect to an input image. In an image quality evaluation processing technique that calculates an image quality evaluation index, processing that uses various kinds of machine learning algorithms such as deep learning is performed. Note that, in the image quality evaluation processing technique, any existing evaluation processing such as processing utilizing an image noise measurement algorithm and matching processing using a database of image quality evaluation indexes corresponding to similar images or fundus images may be performed. Note that, such kinds of evaluation processing may be performed in addition to or instead of processing that uses a machine learning algorithm.

For example, an image quality evaluation index can be obtained by a machine learning model that was built using a machine learning algorithm. In this case, the input data of pairs constituting training data for training the machine learning model is an image group constituted by a low quality image group and a high quality image group which were imaged beforehand according to various imaging conditions. Further, the ground truth of the pairs constituting the training data for training the machine learning model is, for example, an image quality evaluation index group which the examiner who performs the image diagnosis sets with respect to each of the image groups of the input data.

The term "authenticity evaluating engine" as used in the description of the present invention refers to a module that evaluates the rendering of an input image and, with a certain degree of accuracy, evaluates whether or not the image was obtained by imaging by a target imaging apparatus. In the authenticity evaluation processing technique, processing using various kinds of machine learning algorithms such as deep learning is performed. Note that, in the authenticity evaluation processing technique, any existing evaluation processing such as knowledge-based processing may be performed in addition to or instead of processing that uses a machine learning algorithm.

For example, the authenticity evaluation processing can be implemented by a machine learning model built using a machine learning algorithm. First, training data for the machine learning model will be described. The training data includes a pair group composed of a high quality image group imaged beforehand according to various imaging conditions and a label (hereinafter, referred to as a "real label") indicating that the relevant image was obtained by imaging by the target imaging apparatus. Further, the training data includes a pair group composed of a high quality image group generated by inputting low quality images into an image quality improving engine (image quality improving engine of a first level) and a label (hereinafter, referred to as a "fake label") indicating that the relevant image was not obtained by imaging by the target imaging apparatus. When a high quality image that the image quality improving engine of the first level generates is input to a machine learning model trained using such kind of training data, the machine learning model outputs a fake label.

Figure 3:
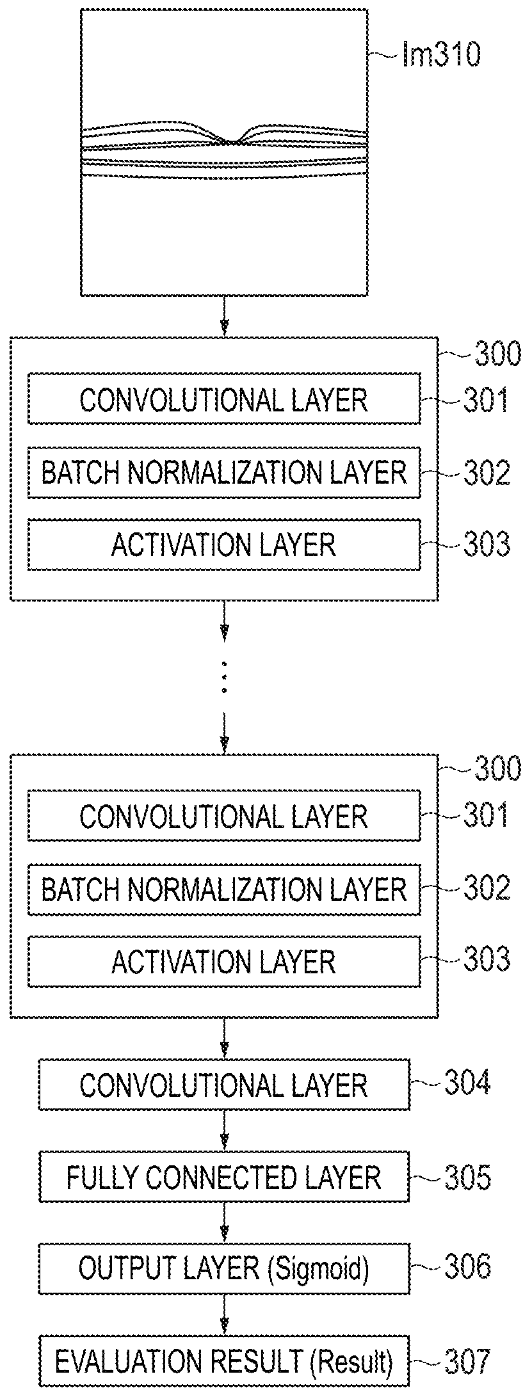
FIG. 3 is a view illustrating an example of a configuration of a neural network relating to authenticity evaluation processing of an image.

In particular, a configuration illustrated in FIG. 3 is available as an example of the configuration of a CNN which performs authenticity evaluation processing on a two-dimensional image. The configuration of the CNN includes a group of a plurality of convolutional processing blocks 300 that are each constituted by a convolutional layer 301, a batch normalization layer 302, and an activation layer 303 that uses a rectifier linear unit. The configuration of the CNN also includes a final convolutional layer 304, a fully connected layer 305, and an output layer 306. The fully connected layer 305 fully connects output value groups of the convolutional processing blocks 300. In addition, the output layer 306 utilizes a sigmoid function to output a value of 1 (True) that represents a real label or a value of 0 (False) that represents a fake label as a result (Result) 307 of the authenticity evaluation processing with respect to an input image Im310.

Note that, by setting the number of convolutional processing blocks 300 to 16, and, as the parameters of the convolutional layer 301 group, setting the kernel size of the filters to a width of three pixels and a height of three pixels, and the number of filters to 64, a correct result of the authenticity evaluation processing is obtained with a certain accuracy. However, in practice, as mentioned in the description of the aforementioned machine learning model, a better parameter group can be set by using training data corresponding to the utilization form of the machine learning model. Note that, in a case where it is necessary to process a three-dimensional image or a four-dimensional image, the kernel size of the filters may be extended to three dimensions or four dimensions.

In some cases, when a high quality image generated by an image quality improving engine (image quality improving engine of a second level) that performs more advanced image quality improving than the image quality improving engine of the first level is input to the authenticity evaluating engine, the authenticity evaluating engine outputs a real label. In other words, while it is not the case that the authenticity evaluating engine can definitely evaluate whether or not an input image was obtained by imaging by an imaging apparatus, the authenticity evaluating engine can evaluate whether or not the image seems like an image obtained by imaging by an imaging apparatus. Utilizing this characteristic, by inputting a high quality image that the image quality improving engine generated into the authenticity evaluating engine, it can be evaluated whether or not the high quality image which the image quality improving engine generated was subjected to sufficient image quality improving.

Further, the efficiency and accuracy of both the image quality improving engine and the authenticity evaluating engine may be improved by coordinating and training the machine learning model of the image quality improving engine and the machine learning model of the authenticity evaluating engine. In this case, first, the machine learning model of the image quality improving engine is trained so that a real label is output when the authenticity evaluating engine is caused to evaluate a high quality image that the high image quality engine generates. Further, in parallel therewith, the machine learning model of the authenticity evaluating engine is trained so as to output a fake label when the authenticity evaluating engine is caused to evaluate an image that the image quality improving engine generates. In addition, in parallel therewith, the machine learning model of the authenticity evaluating engine is trained so as to output a real label when the authenticity evaluating engine is caused to evaluate an image that was obtained by an imaging apparatus. By this means, the efficiency and accuracy of the image quality improving engine and the authenticity evaluating engine improves.

First Embodiment

Figure 4:
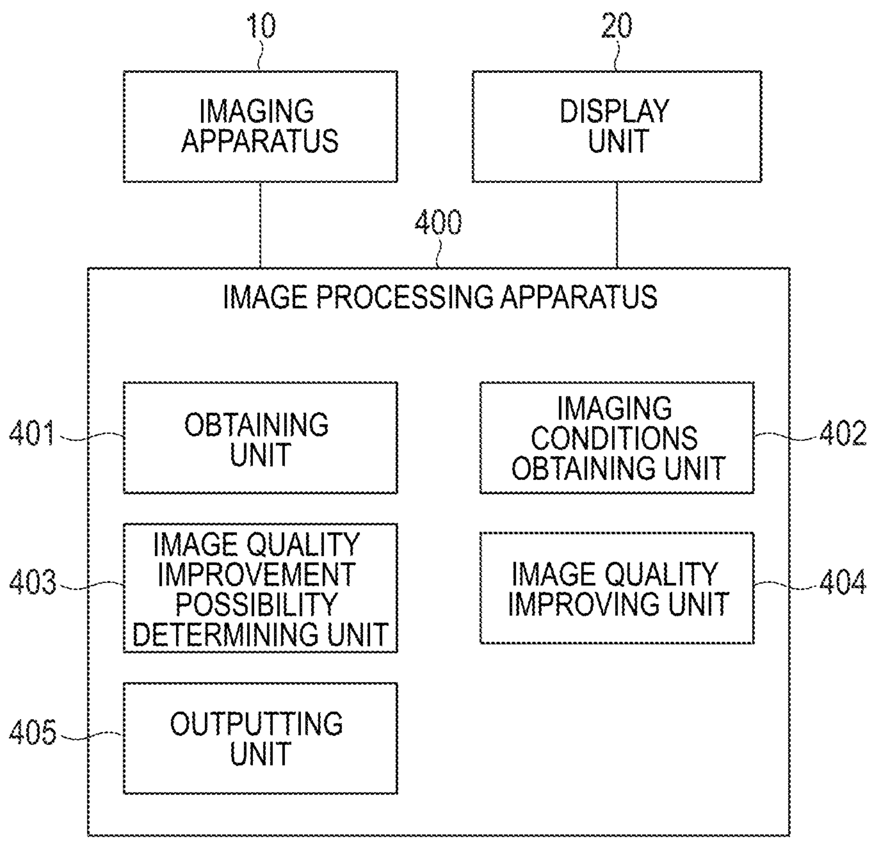
FIG. 4 is a view illustrating an example of a schematic configuration of an image processing apparatus according to a first embodiment.
Figure 5:
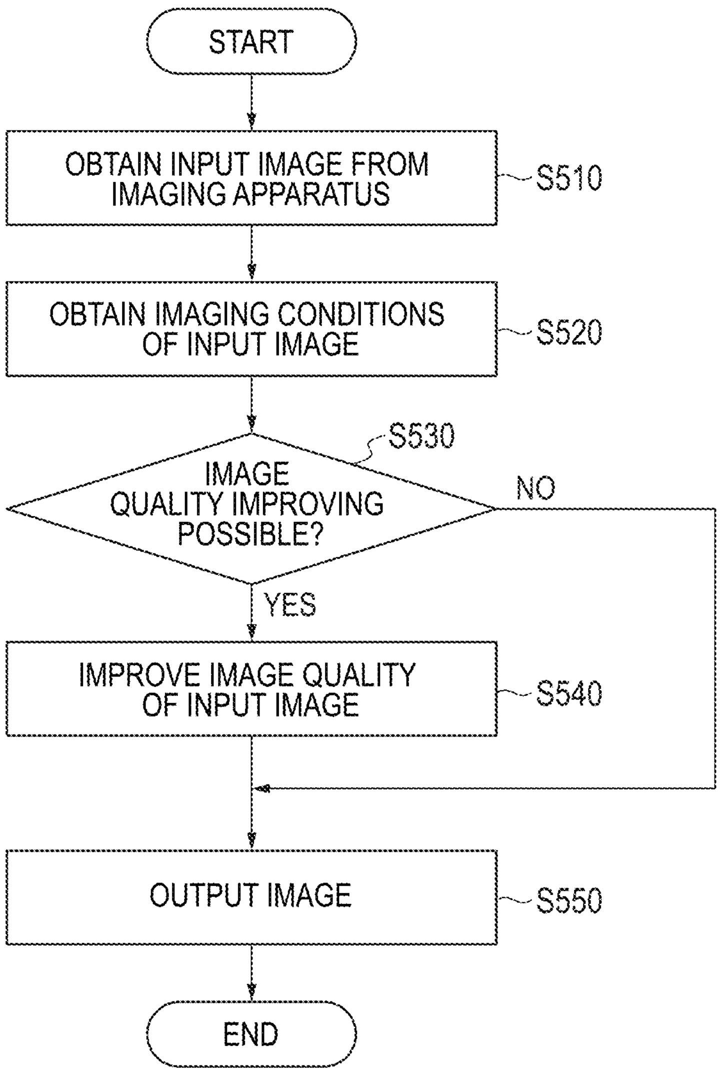
FIG. 5 is a flowchart illustrating an example of a flow of image processing according to the first embodiment.

Hereunder, a medical image processing apparatus according to a first embodiment is described while referring to FIG. 4 and FIG. 5. FIG. 4 is a view illustrating an example of a schematic configuration of the image processing apparatus according to the present embodiment.

An image processing apparatus 400 is connected through a circuit or a network to an imaging apparatus 10 and a display unit 20. The imaging apparatus 10 and the display unit 20 may also be directly connected. Note that, although in the present embodiment these apparatuses are assumed to be separate apparatuses to each other, some or all of these apparatuses may be constituted integrally with each other. Further, these apparatuses may be connected through a circuit or network to any other apparatuses, and may be constituted integrally with any other apparatus.

An obtaining unit 401, an imaging conditions obtaining unit 402, an image quality improvement possibility determining unit 403, an image quality improving unit 404 and an outputting unit 405 (display controlling unit) are provided in the image processing apparatus 400. Note that, the image processing apparatus 400 may be constituted by a plurality of apparatuses which are each provided with one or more of these components. The obtaining unit 401 can obtain various kinds of data and images from the imaging apparatus 10 or another apparatus, and can obtain an input by an examiner through an input apparatus (not illustrated). A mouse, a keyboard, a touch panel and any other input apparatuses may be adopted as an input apparatus. In addition, the display unit 20 may be configured as a touch panel display.

The imaging conditions obtaining unit 402 obtains imaging conditions of a medical image (input image) that the obtaining unit 401 obtained. Specifically, in accordance with the data format of the medical image, an imaging conditions group that is stored in the data structure constituting the medical image is obtained. Note that, in a case where imaging conditions are not stored in the medical image, an imaging information group that includes an imaging conditions group can be obtained from the imaging apparatus 10 or the image management system through the obtaining unit 401.

The image quality improvement possibility determining unit 403 determines whether or not the relevant medical image can be handled by the image quality improving unit 404, using the imaging conditions group obtained by the imaging conditions obtaining unit 402. The image quality improving unit 404 performs processing to improve the image quality of a medical image which can be handled, to thereby generate a high quality image suitable for image diagnosis. The outputting unit 405 causes the display unit 20 to display the high quality image which the image quality improving unit 404 generated, the input image, and various kinds of information or the like. The outputting unit 405 may also store the generated high quality image and the like in a storage apparatus (storage unit) connected to the image processing apparatus 400.

Next, the image quality improving unit 404 will be described in detail. An image quality improving engine is provided in the image quality improving unit 404. According to an image quality improving technique of the image quality improving engine according to the present embodiment, processing that uses a machine learning algorithm is performed.

In the present embodiment, training data that is constituted by a pair group composed of pairs of input data which is a low quality image having specific imaging conditions which are assumed as a processing object, and ground truth which is a high quality image corresponding to the input data is used for training a machine learning model pertaining to a machine learning algorithm. Note that, the specific imaging conditions include, specifically, an imaged site, imaging system, imaging angle of view, image size and the like which are determined in advance.

In the present embodiment, the input data of the training data is a low quality image that is obtained by the same model of equipment as the imaging apparatus 10 and using the same settings as the imaging apparatus 10. Further, the ground truth of the training data is a high quality image obtained using settings and image processing which the same model of equipment as the imaging apparatus 10 is equipped with. Specifically, the ground truth, for example, is a high quality image (averaged image) obtained by performing image quality processing such as an averaging processing on an image (source image) group acquired by performing imaging a plurality of times. Here, OCTA motion contrast data will be described as an example with respect to the high quality images and the low quality images. In this case, the term "motion contrast data" refers to data which is used with OCTA and the like, and which is obtained by repeatedly imaging the same location of the imaging target and detecting temporal changes in the imaging target during the imaging. At such time, an OCTA en-face image (motion contrast front image) can be generated by generating a front image using data of a desired range in the depth direction of the imaging target from among the calculated motion contrast data (one example of three-dimensional medical image data). Note that, hereinafter, the number of images obtained when imaging is repeatedly performed to obtain OCT data at the same location is referred to as "NOR" (number of repeats).

Figure 28A:
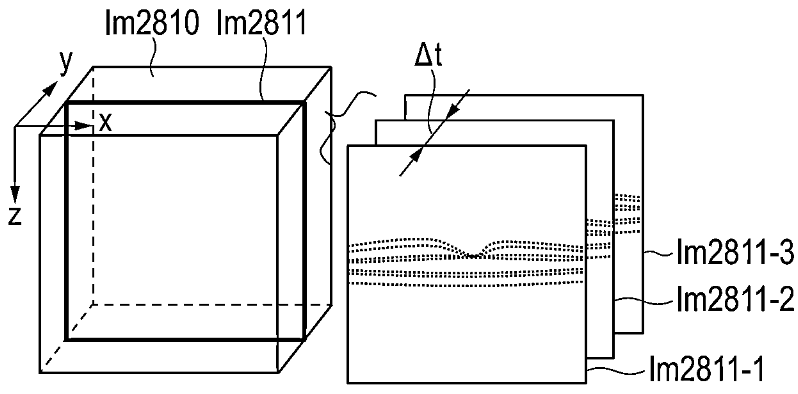
FIG. 28A is a view illustrating an example of a training image relating to image quality improving processing.
Figure 28B:
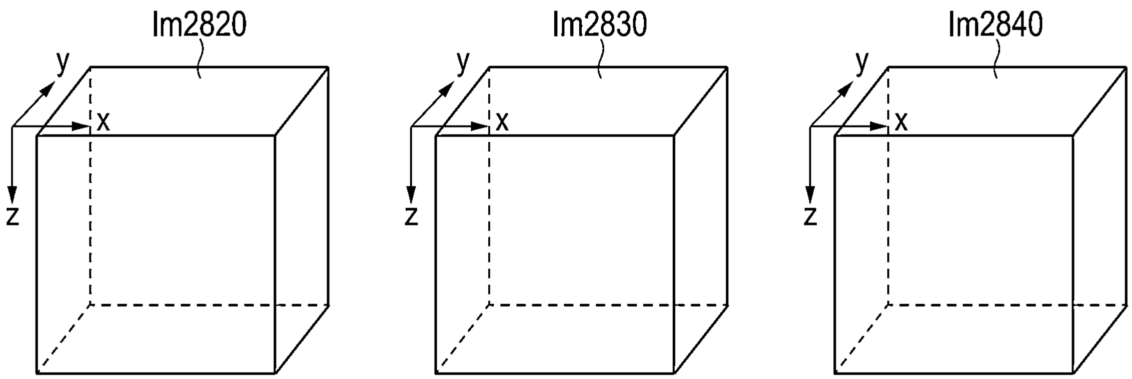
FIG. 28B is a view illustrating examples of training images relating to image quality improving processing.

In the present embodiment, two different kinds of methods will be described as examples of generating a high quality image and a low quality image by averaging processing, using FIG. 28A and FIG. 28B.

A first method relates to motion contrast data generated from OCT data obtained by repeatedly imaging the same location of an imaging target, and will be described using FIG. 28A taking a high quality image as an example. In FIG. 28A, reference characters Im2810 denote three-dimensional motion contrast data, and reference characters Im2811 denote two-dimensional motion contrast data constituting the three-dimensional motion contrast data. Further, reference characters Im2811-1 to Im2811-3 denote OCT tomographic images (B-scans) for generating the motion contrast data Im2811. Here, the term "NOR" refers to the number of OCT tomographic images with respect to Im2811-1 to Im2811-3 in FIG. 28A, and in the example illustrated in the drawing the NOR is 3. The images Im2811-1 to Im2811-3 are imaged at a predetermined time interval (Δt). Note that, the term "same location" refers to one line in the front direction (X-Y) of an eye to be examined, and in FIG. 28A corresponds to the location of Im2811. Note that, the front direction is an example of a direction that intersects with the depth direction. Since motion contrast data is data obtained by detecting temporal changes, it is necessary to make the NOR at least two times in order to generate this data. For example, when the NOR is 2, one piece of motion contrast data is generated. When the NOR is 3, in a case of generating motion contrast data using only OCT obtained at contiguous time intervals (first time and second time, second time and third time), two pieces of data are generated. When motion contrast data is generated by also using OCT data obtained at separated time intervals (first time and third time), a total of three pieces of data are generated. In other words, as the NOR is increased to three times, four times, . . . , the number of pieces of motion contrast data for the same location also increases. Motion contrast data of high image quality can be generated by aligning a plurality of pieces of motion contrast data obtained by repeatedly imaging the same location, and performing an image quality improving processing such as an averaging processing of the aligned pieces of motion contrast data. For this reason, the NOR is set to at least 3 or more, and setting the NOR to 5 or more is desirable. On the other hand, motion contrast data in a state before performing an image quality improving processing such as an averaging processing is taken as an example of a low quality image corresponding thereto. In this case, it is desirable to adopt the low quality image as a reference image when performing the image quality improving processing such as the averaging processing. When performing averaging processing, if alignment is performed in advance by changing the position or deforming the shape of the target image relative to the reference image, there will be almost no spatial displacement between the reference image and the image after the averaging processing. Therefore, a pair that includes a low quality image and a high quality image can be easily made. Note that, the target image that underwent image deformation processing for alignment may be adopted as the low quality image instead of the reference image. A group of a plurality of pairs can be generated by adopting each image of the source image group (reference image and target images) as input data, and the corresponding averaged image as ground truth. For example, in a case where one averaged image is obtained from a group of 15 source images, a pair consisting of the first source image among the source image group and the averaged image can be generated, and a pair consisting of the second source image among the source image group and the averaged image can be generated. Thus, in a case where one averaged image is obtained from a group of 15 source images, it is possible to generate a group of 15 pairs by using one image among the source image group and the averaged image in each pair. Note that, three-dimensional high image quality data can be generated by repeatedly imaging the same location in the main scanning (X) direction and performing scanning while shifting the imaging location in the sub-scanning (Y) direction.

The second method relates to processing that generates a high quality image by performing averaging processing on motion contrast data obtained by imaging the same region of the imaging target a plurality of times, and will be described using FIG. 28B. Note that, the term "same region" refers to a region such as a region of 3×3 mm or 10×10 mm in the front direction (X-Y) of the eye to be examined, and means obtaining three-dimensional motion contrast data including the depth direction of a tomographic image. When imaging the same region a plurality of times and performing averaging processing, in order to shorten the imaging performed at one time, it is desirable to make the NOR two times or three times. Further, in order to generate three-dimensional motion contrast data with high image quality, at least two or more pieces of three-dimensional data of the same region are obtained. FIG. 28B illustrates an example of a plurality of pieces of three-dimensional motion contrast data. Reference characters Im2820 to Im2840 denote three-dimensional motion contrast data, similarly to the example described above using FIG. 28A. Alignment processing in the front direction (X-Y) and depth direction (Z) is performed using these two or more pieces of three-dimensional motion contrast data, and after data which would become an artifact is removed from each piece of data, averaging processing is perform. Thus, one piece of three-dimensional motion contrast data with high image quality from which artifacts were removed can be generated. A high quality image is obtained by generating an arbitrary plane from the three-dimensional motion contrast data. On the other hand, it is desirable that an arbitrary plane which is generated from the reference data when performing the image quality improving processing such as the averaging processing is adopted as a low quality image that corresponds to the high quality image. As described above in regard to the first method, since there is almost no spatial displacement between the reference image and the image after the averaging, a pair that includes a low quality image and a high quality image can be easily made. Note that, an arbitrary plane generated from the target data on which image deformation processing for alignment was performed, and not the reference data, may be adopted as the low quality image.

In the first method, the burden on the subject is smaller because the imaging itself is completed after one round of imaging. However, the time required for one round of imaging increases as the number of the NOR is increased. In addition, a favorable image is not always obtained in a case where an artifact such as turbidity of the eye or an eyelash enters while imaging is being performed. In the second method, the burden on the subject slightly increases because imaging is performed a plurality of times. However, the time required for one round of imaging is short, and even if an artifact is generated in one round of imaging, as long as the artifact is not imaged in another round of imaging it is possible to ultimately obtain a clear image in which there are few artifacts. When collecting data, an arbitrary method is selected according to the circumstances of the subject taking these characteristics into consideration.

Although the present embodiment has been described taking motion contrast data as an example, the present invention is not limited thereto. Since OCT data is obtained in order to generate motion contrast data, it is possible to perform the aforementioned methods in the same way using OCT data. In addition, although a description regarding tracking processing has been omitted from the present embodiment, it is desirable to perform imaging while performing tracking of the eye to be examined in order to image the same location or same region of the eye to be examined.

Figure 29A:
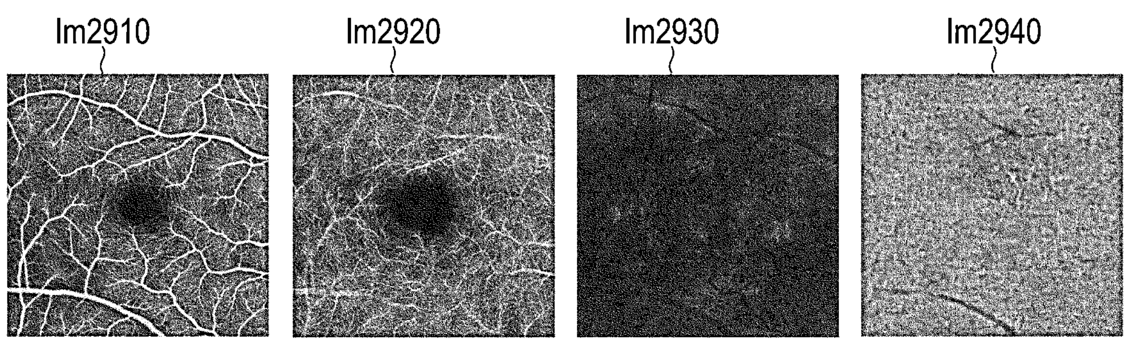
FIG. 29A is a view illustrating examples of input images relating to image quality improving processing.

In the present embodiment, since a pair consisting of three-dimensional high image quality data and three-dimensional low image quality data can be made, an arbitrary pair of two-dimensional images can be generated from the three-dimensional data. This will now be described using FIG. 29A and FIG. 29B. For example, when the target image is taken as an OCTA en-face image, an OCTA en-face image is generated in a desired depth range based on the three-dimensional data. The term "desired depth range" refers to a range in the Z-direction in FIG. 28A and FIG. 28B. Examples of OCTA en-face images generated in such a case are illustrated in FIG. 29A. Learning is performed using OCTA en-face images generated in different depth ranges as OCTA en-face images, such as a surface layer (Im2910), a deep layer (Im2920), an outer layer (Im2930), and a choroidal vascular network (Im2940). Note that, the kinds of OCTA en-face images are not limited to these examples, and the kinds may be increased by generating OCTA en-face images in which different depth ranges are set by changing the layer that serves as a reference and the offset values. When performing learning, learning may be performed separately for each of the OCTA en-face images at the different depths, learning may be performed by combining a plurality of images in different depth ranges (for example, splitting images between the surface layer side and the deep layer side), or learning may be performed by learning the OCTA en-face images for all the depth ranges together. In the case of an intensity en-face image that is generated from OCT data also, similarly to an OCTA en-face image, learning is performed using a plurality of en-face images generated from an arbitrary depth range. For example, let us consider a case where the image quality improving engine includes a machine learning engine obtained using training data including a plurality of motion contrast front images corresponding to different depth ranges of the eye to be examined. At such time, the obtaining unit can obtain, as a first image, a motion contrast front image corresponding to a partial depth range among a long depth range that includes different depth ranges. In other words, a motion contrast front image corresponding to a depth range that is different from a plurality of depth ranges corresponding to a plurality of motion contrast front images included in the training data can be used as an input image when performing image quality improving. Naturally, a motion contrast front image in the same depth range as the depth range used for learning may be used as an input image when performing image quality improving. Further, a partial depth range may be set in response to the examiner pressing an arbitrary button on the user interface or the like, or may be set automatically. Note that, the contents described above are not limited to a motion contrast front image, and for example can also be applied to an intensity en-face image.

Figure 29B:
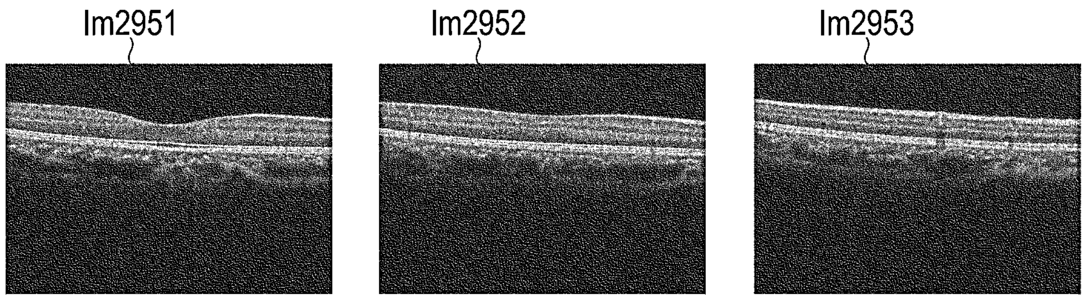
FIG. 29B is a view illustrating examples of input images relating to image quality improving processing.
Figure 30:
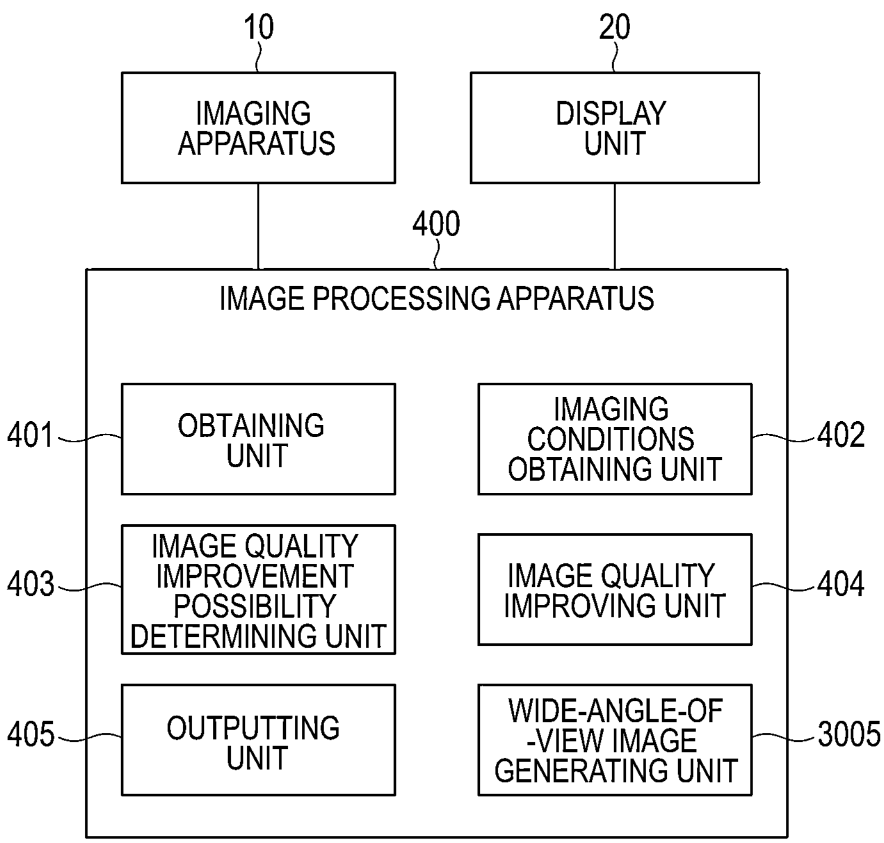
FIG. 30 is a view illustrating an example of a schematic configuration of an image processing apparatus according to a twenty-second embodiment.

Note that, when the image that is the processing object is a tomographic image, learning is performed using an OCT tomographic image that is a B-scan image or a tomographic image of motion contrast data. This will now be described using FIG. 29B. In FIG. 29B, reference characters Im2951 to Im2953 denote OCT tomographic images. The reason the images in FIG. 29B differ is that they show tomographic image at locations where the respective positions in the sub-scanning (Y) direction differ. The tomographic images may be used together to perform learning without being concerned about differences in the respective positions in the sub-scanning direction. However, in the case of images obtained by imaging of locations where the imaged sites (for example, the center of the macular area and the center of the optic nerve head) differ, a configuration may be adopted so as to perform learning separately for each site, or a configuration may be adopted so as to perform learning together without being concerned about the imaged sites. Note that, since image feature values differ significantly between an OCT tomographic image and a tomographic image of motion contrast data, it is better to perform learning separately for such images.

An averaged image that underwent averaging processing is a high quality image that is suitable for image diagnosis because pixels that are commonly visualized in a source image group are enhanced. In this case, as a result of pixels commonly visualized being enhanced, the generated high quality image is a high contrast image in which a difference between a low intensity region and a high intensity region is clear. In addition, for example, in an averaged image, random noise that is generated at each round of imaging can be reduced, and a region that was not rendered well in a source image at a certain time point can be subjected to interpolation using another source image group.

Further, in a case where it is necessary to construct the input data of a machine learning model with a plurality of images, a necessary number of source image groups can be selected from among the source image groups and adopted as input data. For example, in a case where one averaged image is obtained from a group of 15 source images, if two images are required as input data of the machine learning model, it is possible to generate a group of 105 (15C2=105) pairs.

Note that, among the pair groups constituting the training data, pairs that do not contribute to improving image quality can be removed from the training data. For example, if the image quality of a high quality image that is ground truth included in one pair of the training data is not suitable for image diagnosis, there is a possibility that an image output by an image quality improving engine that learned using the relevant training data will have image quality that is not suitable for image diagnosis. Therefore, by removing pairs for which the image quality of the ground truth is not suitable for image diagnosis from the training data, the possibility of the image quality improving engine generating an image with image quality that is not suitable for image diagnosis can be reduced.

Further, in a case where the average intensity or a intensity distribution differs greatly in an image group which is a pair, there is a possibility that an image quality improving engine that learned using the relevant training data will output an image which is not suitable for image diagnosis which has a intensity distribution that greatly differs from the intensity distribution of the low quality image. Therefore, a pair of input data and ground truth in which the average intensity or an intensity distribution differs greatly can be removed from the training data.

In addition, in a case where the structure or position of an imaging target to be rendered differs greatly in an image group which is a pair, there is a possibility that an image quality improving engine that learned using the relevant training data will output an image which is not suitable for image diagnosis in which the imaging target is rendered with a structure or at a position that greatly differs from the low quality image. Therefore, a pair of input data and ground truth in which the structure or position of the imaging target to be rendered differs greatly between the input data and ground truth can also be removed from the training data. Further, with regard to the image quality improving engine, from the viewpoint of maintaining quality, the image quality improving engine can be configured so as not to use a high quality image which the image quality improving engine itself outputs, as training data.

By using the image quality improving engine that has performed machine learning in this way, in a case where a medical image obtained by one round of imaging is input, the image quality improving unit 404 can output a high quality image for which the contrast was increased or noise was reduced or the like by averaging processing. Therefore, the image quality improving unit 404 can generate a high quality image that is suitable for image diagnosis based on a low quality image that is an input image.

Next, a series of image processing operations according to the present embodiment will be described referring to a flowchart illustrated in FIG. 5. FIG. 5 is a flowchart illustrating the series of image processing operations according to the present embodiment. First, when the series of image processing operations according to the present embodiment is started, the processing shifts to step S510.

In step S510, an image that was imaged by the imaging apparatus 10 is obtained as an input image by the obtaining unit 401 from the imaging apparatus 10 connected to the obtaining unit 401 through a circuit or a network. Note that, the obtaining unit 401 may obtain an input image in response to a request from the imaging apparatus 10. Such a request may be issued, for example, when the imaging apparatus 10 generated an image, or when displaying an image which the imaging apparatus 10 generated on the display unit 20 before storing the image in a storage apparatus which the imaging apparatus 10 includes or displaying the stored image on the display unit 20 after storing the image in the storage apparatus, or when utilizing a high quality image for image analysis processing.

Note that, the obtaining unit 401 may obtain data for generating an image from the imaging apparatus 10, and the image processing apparatus 400 may obtain an image generated based on the relevant data as an input image. In this case, the image processing apparatus 400 may employ any existing image generating method as an image generating method for generating various kinds of images.

In step S520, the imaging conditions obtaining unit 402 obtains an imaging conditions group for the input image. Specifically, in accordance with the data format of the input image, the imaging conditions obtaining unit 402 obtains an imaging conditions group stored in the data structure constituting the input image. Note that, as mentioned above, in a case where imaging conditions are not stored in the input image, the imaging conditions obtaining unit 402 can obtain an imaging information group including an imaging conditions group from the imaging apparatus 10 or the image management system which is not illustrated in the drawings.

In step S530, the image quality improvement possibility determining unit 403 uses the obtained imaging conditions group to determine whether or not it is possible for the image quality of the input image to be improved by the image quality improving engine which the image quality improving unit 404 includes. Specifically, the image quality improvement possibility determining unit 403 determines whether or not the imaged site, imaging system, imaging angle of view and image size of the input image match conditions which can be handled by the image quality improving engine.

The image quality improvement possibility determining unit 403 makes determination regarding all of the imaging conditions, and if the image quality improvement possibility determining unit 403 determines that the image quality improving engine is capable of handling the imaging conditions, the processing shifts to step S540. On the other hand, if, based on these imaging conditions, the image quality improvement possibility determining unit 403 determines that the image quality improving engine is not capable of handling the input image, the processing shifts to step S550.

Note that, depending on the settings and implementation form of the image processing apparatus 400, even if it is determined that the input image cannot be processed based on some conditions among the imaged site, imaging system, imaging angle of view and image size, the image quality improving processing in step S540 may be performed. For example, such processing may be performed in a case where it is assumed that the image quality improving engine is capable of comprehensively handling any imaged site of the subject, and is implemented so as to be capable of handling input data even if an unknown imaged site is included in the input data. In addition, the image quality improvement possibility determining unit 403 may determine whether or not at least one condition among the imaged site, imaging system, imaging angle of view and image size of an input image matches a condition which the image quality improving engine is capable of handling according to a desired configuration.

In step S540, the image quality improving unit 404 improves the image quality of the input image using the image quality improving engine, to thereby generate a high quality image that is more suitable for image diagnosis than the input image. Specifically, the image quality improving unit 404 inputs the input image to the image quality improving engine to cause the image quality improving engine to generate a high quality image which has been subjected to image quality improving. The image quality improving engine generates a high quality image obtained by performing averaging processing using the input image based on the machine learning model which performed machine learning using training data. Thus, the image quality improving engine can generate a high quality image in which noise is reduced or contrast is enhanced compared to the input image.

Note that, depending on the settings or implementation form of the image processing apparatus 400, the image quality improving unit 404 may input parameters together with the input image into the image quality improving engine in accordance with the imaging conditions group, to adjust the degree of image quality improving or the like. Further, the image quality improving unit 404 may also input parameters in accordance with an input by the examiner together with the input image into the image quality improving engine to adjust the degree of image quality improving or the like.

In step S550, if a high quality image has been generated in step S540, the outputting unit 405 outputs the high quality image and causes the high quality image to be displayed on the display unit 20. On the other hand, in a case where it was not possible to perform image quality improving processing in step S530, the outputting unit 405 outputs the input image and causes the input image to be displayed on the display unit 20. Note that, instead of causing an output image to be displayed on the display unit 20, the outputting unit 405 may cause the output image to be displayed on the imaging apparatus 10 or another apparatus or may store the output image. Further, depending on the settings or implementation form of the image processing apparatus 400, the outputting unit 405 may process the output image so that the output image can be utilized by the imaging apparatus 10 or another apparatus, or may convert the data format of the output image so that the output image can be transmitted to the image management system or the like. As mentioned above, the image processing apparatus 400 according to the present embodiment includes the obtaining unit 401 and the image quality improving unit 404. The obtaining unit 401 obtains an input image (first image) that is an image of a predetermined site of the subject. The image quality improving unit 404 uses an image quality improving engine that includes a machine learning engine to generate, from the input image, a high quality image (second image) which has undergone at least one of noise reduction and contrast enhancement relative to the input image. The image quality improving engine includes a machine learning engine for which images obtained by averaging processing were adopted as training data.

By this configuration, the image processing apparatus 400 according to the present embodiment can output a high quality image in which noise is reduced and/or contrast is enhanced from an input image. Therefore, the image processing apparatus 400 can obtain an image suitable for image diagnosis such as a clearer image or an image in which a site or lesion that it is desired to observe is enhanced, while paying less of a price and without increasing the invasiveness with respect to the subject or the labor of the person performing the imaging in comparison to the conventional technology.

The image processing apparatus 400 also includes the image quality improvement possibility determining unit 403 for determining, with respect to an input image, whether or not a high quality image can be generated using the image quality improving engine. The image quality improvement possibility determining unit 403 performs the determination in question based on at least one of the imaged site, imaging system, imaging angle of view and image size of the input image.

By this configuration, the image processing apparatus 400 according to the present embodiment can omit an input image which the image quality improving unit 404 cannot process from the image quality improving processing, and thus the processing load of the image processing apparatus 400 and the occurrence of errors can be decreased.

Note that, although in the present embodiment the outputting unit 405 (display controlling unit) is configured to cause a generated high quality image to be displayed on the display unit 20, the operations of the outputting unit 405 are not limited thereto. For example, the outputting unit 405 can also output a high quality image to the imaging apparatus 10 or to another apparatus connected to the image processing apparatus 400. Therefore, a high quality image can be displayed on a user interface of these apparatuses, can be stored in any storage apparatus, can be utilized for any image analysis, or can be transmitted to an image management system.

Figure 6:
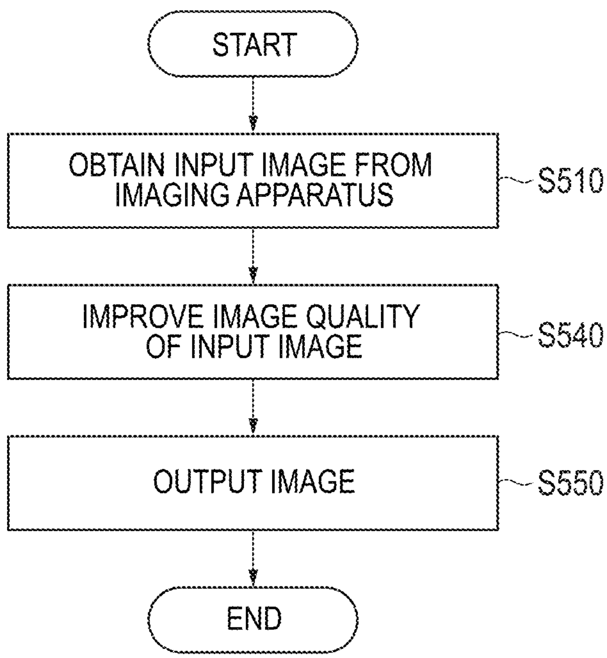
FIG. 6 is a flowchart illustrating a different example of the flow of image processing according to the first embodiment.

In the present embodiment, the image quality improvement possibility determining unit 403 determines whether or not an input image is an image whose image quality can be improved by the image quality improving engine, and if the input image is an image whose image quality can be improved, the image quality improving unit 404 performs processing to improve the image quality. In this regard, in a case where only imaging under imaging conditions which enable image quality improving is performed by the imaging apparatus 10 or the like, an image obtained from the imaging apparatus 10 may be unconditionally subjected to image quality improving. In this case, as illustrated in FIG. 6, the processing in step S520 and step S530 can be omitted, and step S540 can be executed after step S510.

In the present embodiment, the outputting unit 405 is configured to cause a high quality image to be displayed on the display unit 20. However, the outputting unit 405 may cause a high quality image to be displayed on the display unit 20 in response to an instruction from the examiner. For example, the outputting unit 405 may display a high quality image on the display unit 20 in response to the examiner pressing an arbitrary button on a user interface of the display unit 20. In this case, the outputting unit 405 may switch from displaying the input image to display the high quality image, or may display the high quality image side by side with the input image.

In addition, when displaying a high quality image on the display unit 20, the outputting unit 405 may cause a display which indicates that the image being displayed is a high quality image generated by processing that used a machine learning algorithm to be displayed together with the high quality image. In this case, since a user can easily discern by the relevant display that the displayed high quality image is not the actual image obtained by imaging, misdiagnosis can be reduced and the diagnosis efficiency can be improved. Note that, a display indicating that a high quality image was generated by processing that used a machine learning algorithm may be of any form as long as it is a display which makes it possible to distinguish between the input image and the high quality image generated by the relevant processing.

Further, with respect to the display indicating that a high quality image was generated by processing that used a machine learning algorithm, the outputting unit 405 may cause a display indicating what kind of training data the machine learning algorithm used when the machine learning algorithm performed learning to be displayed on the display unit 20. The display in question may include a description of the kinds of input data and ground truth of the training data, or any display relating to the training data such as an imaged site included in the input data and ground truth.

Although an averaged image is used as the ground truth of the training data in the image quality improving engine according to the present embodiment, the training data is not limited thereto. A high quality image obtained by performing at least one of averaging processing, processing of a processing group to be described later, and an imaging method to be described later, which are units for obtaining a high quality image, may be used as ground truth of the training data.

For example, a high quality image obtained by performing maximum a posteriori processing (MAP estimation processing) with respect to a source image group may be used as ground truth of the training data. In MAP estimation processing, a likelihood function is obtained based on the probability density of each pixel value in a plurality of low quality images, and a true signal value (pixel value) is estimated using the obtained likelihood function.

A high quality image obtained by MAP estimation processing is a high contrast image that is based on pixel values that are close to the true signal values. Further, since the estimated signal values are determined based on the probability density, randomly generated noise is reduced in a high quality image obtained by MAP estimation processing. Therefore, by using a high quality image obtained by MAP estimation processing as training data, the image quality improving engine can generate, from an input image, a high quality image that is suitable for image diagnosis in which noise is reduced and which has high contrast. Note that, with regard to the method for generating a pair of input data and ground truth of the training data, a method that is similar to a case where an averaged image is used as training data may be performed.

Further, as ground truth of the training data, a high quality image obtained by applying smoothing filter processing to a source image may be used. In this case, the image quality improving engine can generate a high quality image in which random noise is reduced from an input image. In addition, an image obtained by applying gradation conversion processing to a source image may also be used as ground truth of the training data. In this case, the image quality improving engine can generate a high quality image with enhanced contrast from an input image. Note that, with regard to the method for generating a pair of input data and ground truth of the training data, a method that is similar to a case where an averaged image is used as training data may be performed.

Note that, the input data of the training data may be an image obtained from an imaging apparatus having the same image quality tendency as the imaging apparatus 10. Further, the ground truth of the training data may be a high quality image obtained by high-cost processing such as processing using the method of successive approximation, or may be a high quality image obtained by imaging a subject corresponding to the input data using an imaging apparatus with higher performance than the imaging apparatus 10. In addition, the ground truth may be a high quality image obtained by performing rule-based noise reduction processing. Here, the noise reduction processing can include, for example, processing that replaces a high intensity pixel that is only one pixel which is clearly noise that appears in a low intensity region with the average value of neighboring low-intensity pixel values. Thus, as training data, the image quality improving engine may adopt an image imaged by an imaging apparatus with higher performance than the imaging apparatus used to image an input image, or an image obtained by an imaging step that involves a greater number of steps than the imaging step used to obtain the input image. For example, in the case of adopting a motion contrast front image as an input image, the image quality improving engine may adopt, as training data, an image obtained by OCTA imaging performed by an OCT imaging apparatus with higher performance than the OCT imaging apparatus used for OCTA imaging of the input image, or an image obtained by an OCTA imaging step that involves a greater number of steps than the OCTA imaging step for the input image.

Note that, although omitted in the description of the present embodiment, a high quality image generated from a plurality of images to be used as ground truth of the training data can be generated from a plurality of images which have been aligned. As the alignment processing, for example, processing may be adopted in which one image among the plurality of images is selected as a template, then the degree of similarity with the other images is determined while changing the position and angle of the template, the amount of displacement of each image relative to the template is determined, and each image is corrected based on the amount of displacement. Further, any other existing alignment processing may also be performed.

Note that, in the case of aligning a three-dimensional image, alignment of the three-dimensional image may be performed by breaking down the three-dimensional image into a plurality of two-dimensional images, and then aligning the respective two-dimensional images and integrating the aligned two-dimensional images. Further, alignment of a two-dimensional image may be performed by breaking down the two-dimensional image into one-dimensional images, and then aligning the respective one-dimensional images and integrating the aligned one-dimensional images. Note that, instead of an image, these alignment processes may be performed with respect to data for generating an image.

Further, in the present embodiment, if the image quality improvement possibility determining unit 403 determines that an input image can be handled by the image quality improving unit 404, the processing shifts to step S540, and image quality improving processing by the image quality improving unit 404 is started. In this regard, a configuration may also be adopted in which the outputting unit 405 causes the result of determination by the image quality improvement possibility determining unit 403 to be displayed on the display unit 20, and the image quality improving unit 404 starts image quality improving processing in response to an instruction from the examiner. At such time, together with the result of the determination, the outputting unit 405 can also cause the input image or imaging conditions such as the imaged site obtained with respect to the input image to be displayed on the display unit 20. In this case, since image quality improving processing is performed after the examiner has determined whether or not the result of the determination by the image quality improvement possibility determining unit 403 is correct, image quality improving processing based on an erroneous determination can be reduced.

Further, a configuration may also be adopted in which determination is not performed by the image quality improvement possibility determining unit 403, the outputting unit 405 causes the input image or imaging conditions such as the imaged site obtained with respect to the input image to be displayed on the display unit 20, and the image quality improving unit 404 starts image quality improving processing in response to an instruction from the examiner.

Second Embodiment

Figure 7:
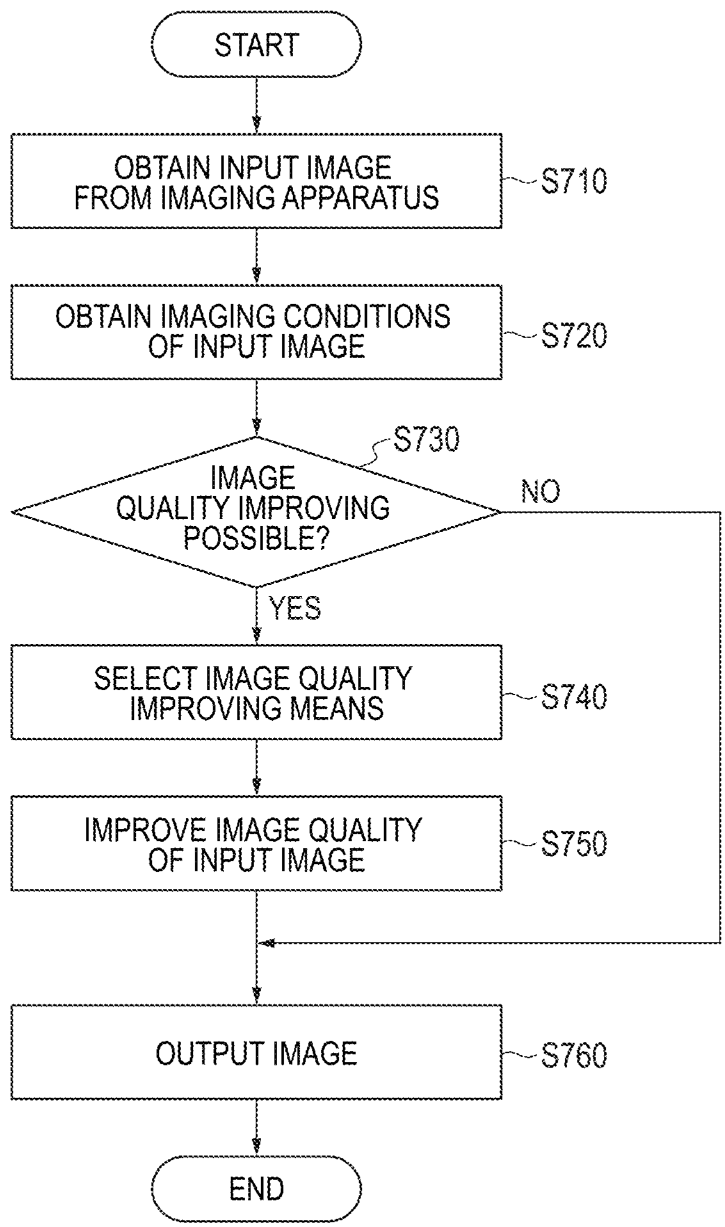
FIG. 7 is a flowchart illustrating an example of a flow of image processing according to a second embodiment.

Next, an image processing apparatus according to a second embodiment is described referring to FIG. 4 and FIG. 7. In the first embodiment, the image quality improving unit 404 includes one image quality improving engine. In contrast, in the present embodiment, an image quality improving unit includes a plurality of image quality improving engines which performed machine learning using different training data to each other, and generates a plurality of high quality images with respect to an input image.

Unless explicitly stated otherwise, the configuration and processing of the image processing apparatus according to the present embodiment are the same as the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The image quality improving unit 404 according to the present embodiment includes two or more image quality improving engines which performed machine learning using different training data to each other. A method for creating a training data group according to the present embodiment will now be described. Specifically, first, imaging of various imaged sites is performed, and a pair group composed of pairs of a source image as input data and an averaged image as ground truth are prepared. Next, a pair group is grouped for each imaged site to create a training data group. For example, a training data group is created by creating first training data composed of a pair group obtained by imaging a first imaged site, and creating second training data composed of a pair group obtained by imaging a second imaged site.

Thereafter, the respective image quality improving engines are caused to perform machine learning using the respective training data. For example, an image quality improving engine group is prepared that includes a first image quality improving engine corresponding to a machine learning model that was trained using the first training data, and a second image quality improving engine corresponding to a machine learning model that was trained using the second training data.

Because different training data is used for training the respective machine learning models corresponding to each of these image quality improving engines, the degree to which each of these image quality improving engines can improve the image quality of an input image input to the image quality improving engines will differ according to the imaging conditions of the input image. Specifically, in the case of the first image quality improving engine, the degree of image quality improving with respect to an input image obtained by imaging the first imaged site is high, and the degree of image quality improving with respect to an input image obtained by imaging the second imaged site is low. Similarly, in the case of the second image quality improving engine, the degree of image quality improving with respect to an input image obtained by imaging the second imaged site is high, and the degree of image quality improving with respect to an input image obtained by imaging the first imaged site is low.

Since each set of training data is composed of a pair group which is grouped according to the imaged site, images in the image group constituting the pair group have a similar image quality tendency. Therefore, if the imaged site corresponds to the relevant image quality improving engine, the image quality improving engine can perform image quality improving more effectively than the image quality improving engine according to the first embodiment. Note that, an imaging condition for grouping pairs of the training data is not limited to the imaged site, and may be the imaging angle of view or the resolution of the image, or a combination of two or more of these conditions.

Hereunder, a series of image processing operations according to the present embodiment is described referring to FIG. 7. FIG. 7 is a flowchart of the series of image processing operations according to the present embodiment. Note that, the processing in step S710 and step S720 is the same as the processing in step S510 and step S520 according to the first embodiment, and hence a description of the processing is omitted here. Note that, in a case where the image quality of an input image is to be improved unconditionally, after performing the processing in step S720, the processing in step S730 can be omitted and the processing can shift to step S740.

Upon the imaging conditions of the input image being obtained in step S720, the processing shifts to step S730. In step S730, the image quality improvement possibility determining unit 403 uses the imaging conditions group obtained in step S720 to determine whether or not any of the group of image quality improving engines which the image quality improving unit 404 includes can handle the input image.

If the image quality improvement possibility determining unit 403 determines that none of the group of image quality improving engines is capable of handling the input image, the processing shifts to step S760. On the other hand, if the image quality improvement possibility determining unit 403 determines that any of the group of image quality improving engines is capable of handling the input image, the processing shifts to step S740. Note that, depending on the settings or implementation form of the image processing apparatus 400, similarly to the first embodiment, even if it is determined that the image quality improving engines are not capable of handling some of the imaging conditions, the processing in step S740 may be executed.

In step S740, the image quality improving unit 404 selects the image quality improving engine to perform image quality improving processing from the image quality improving engine group, based on the imaging conditions of the input image obtained in step S720 and information pertaining to the training data of the image quality improving engine group. Specifically, for example, the image quality improving unit 404 selects an image quality improving engine which, with respect to the imaged site in the imaging conditions group obtained in step S720, has information of training data relating to the same imaged site or a peripheral imaged site and can perform image quality improving with high degree of image quality improving. In the aforementioned example, if the imaged site is the first imaged site, the image quality improving unit 404 selects the first image quality improving engine.

In step S750, the image quality improving unit 404 uses the image quality improving engine selected in step S740 to generate a high quality image generated by improving the image quality of the input image. Thereafter, in step S760, if a high quality image was generated in step S750, the outputting unit 405 outputs the high quality image and causes the display unit 20 to display the high quality image. On the other hand, if it was determined in step S730 that image quality improving processing is not possible, the outputting unit 405 outputs the input image and causes the display unit 20 to display the input image. Note that, when causing the display unit 20 to display the high quality image, the outputting unit 405 may also cause the display unit 20 to display information indicating that the high quality image is a high quality image generated using an image quality improving engine selected by the image quality improving unit 404.

As described above, the image quality improving unit 404 according to the present embodiment includes a plurality of image quality improving engines which performed learning using different training data to each other. Here, each of the plurality of image quality improving engines performed learning using different training data to each other with regard to at least one imaging condition among the imaged site, the imaging angle of view, a front image at different depths, and the image resolution. The image quality improving unit 404 generates a high quality image using an image quality improving engine in accordance with at least one imaging condition among the imaged site, the imaging angle of view, a front image at different depths, and the image resolution of the input image.

By this configuration, the image processing apparatus 400 according to the present embodiment can generate a more effective high quality image.

Although in the present embodiment the image quality improving unit 404 selects an image quality improving engine to be used for image quality improving processing based on an imaging condition of the input image, processing for selecting an image quality improving engine is not limited thereto. For example, the outputting unit 405 may cause the imaging conditions of the obtained input image and an image quality improving engine group to be displayed on a user interface of the display unit 20, and the image quality improving unit 404 may select the image quality improving engine to be used for image quality improving processing in accordance with an instruction from the examiner. Note that, the outputting unit 405 may cause information pertaining to the training data used for learning by the respective image quality improving engines to be displayed on the display unit 20 together with the image quality improving engine group. Note that, information pertaining to training data used for learning by an image quality improving engine may be displayed in any form, and for example the image quality improving engine group may be displayed using names associated with the training data used for learning.

Further, the outputting unit 405 may cause an image quality improving engine that was selected by the image quality improving unit 404 to be displayed on the user interface of the display unit 20, and may accept an instruction from the examiner. In this case, the image quality improving unit 404 may determine whether or not to ultimately select the relevant image quality improving engine as the image quality improving engine to be used for image quality improving processing in accordance with the instruction from the examiner.

Note that, similarly to the first embodiment, the outputting unit 405 may output a generated high quality image to the imaging apparatus 10 or to another apparatus connected to the image processing apparatus 400. Further, similarly to the first embodiment, the ground truth of training data for an image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Third Embodiment

Next, an image processing apparatus according to a third embodiment is described referring to FIG. 4 and FIG. 7. In the first and second embodiments, the imaging conditions obtaining unit 402 obtains an imaging conditions group from the data structure of the input image or the like. In contrast, in the present embodiment, an imaging conditions obtaining unit uses an imaged location estimating engine to estimate an imaged site or imaged region of an input image, based on the input image.

Unless explicitly stated otherwise, the configuration and processing of the image processing apparatus according to the present embodiment are the same as the image processing apparatus 400 according to the second embodiment. Therefore, hereunder, the image processing apparatus according to the present embodiment is described centering on differences from the image processing apparatus according to the second embodiment. Note that, since the configuration of the image processing apparatus according to the present embodiment is the same as the configuration of the image processing apparatus according to the first and second embodiments, components illustrated in FIG. 4 are denoted by the same reference numerals as in the first and second embodiments, and a description of the components is omitted hereunder.

The imaging conditions obtaining unit 402 according to the present embodiment includes an imaged location estimating engine for estimating an imaged site or imaged region that is rendered in an input image which the obtaining unit 401 obtained. According to a technique for estimating an imaged location of the imaged location estimating engine according to the present embodiment, estimation processing is performed using a machine learning algorithm.

In the present embodiment, training data constituted by a pair group composed of input data that is an image and ground truth that is an imaged site label or an imaged region label corresponding to the input data is used for training a machine learning model pertaining to an imaged location estimating technique that uses a machine learning algorithm. Here, the term "input data" refers to an image which has specific imaging conditions assumed for a processing object (input image). An image obtained from an imaging apparatus having the same image quality tendency as the imaging apparatus 10 can be used as the input data, and it is better if the imaging apparatus is the same model of equipment as the imaging apparatus 10 and was set with the same settings as the imaging apparatus 10. The kinds of imaged site labels or imaged region labels serving as the ground truth may be the relevant imaged site or imaged region at least partially included in the input data. The kinds of imaged site labels serving as the ground truth may be, for example, in the case of OCT, "macular area", "optic nerve head", "macular area and optic nerve head" and "other".

By performing learning using such kind of training data, the imaged location estimating engine according to the present embodiment can output information indicating the location of an imaged site or imaged region that is rendered in an input image. Further, for each imaged site label or imaged region label of a required level of detail, the imaged location estimating engine can also output the probability of being the relevant imaged site or imaged region. By using the imaged location estimating engine, based on an input image, the imaging conditions obtaining unit 402 can estimate an imaged site or imaged region of the input image and thereby obtain the imaged site or imaged region as an imaging condition with respect to the input image. Note that, in a case where, for each imaged site label or imaged region label, the imaged location estimating engine outputs the probability of being the relevant imaged site or imaged region, the imaging conditions obtaining unit 402 obtains the imaged site or imaged region with the highest probability as an imaging condition of the input image.

Next, similarly to the second embodiment, a series of image processing operations according to the present embodiment is described referring to a flowchart in FIG. 7. Note that, since the processing in step S710 and step S730 to step S760 according to the present embodiment is the same as the processing in these steps in the second embodiment, a description of the processing is omitted here. Note that, in a case where the image quality of an input image is to be improved unconditionally, after the processing in step S720, the processing in step S730 can be omitted and the processing can shift to step S740.

Upon an input image being obtained in step S710, the processing shifts to step S720. In step S720, the imaging conditions obtaining unit 402 obtains an imaging conditions group of the input image obtained in step S710.

Specifically, an imaging conditions group stored in the data structure constituting the input image is obtained according to the data format of the input image. Further, if information relating to the imaged site or imaged region is not included in the imaging conditions group, the imaging conditions obtaining unit 402 inputs the input image to the imaged location estimating engine to estimate which imaged site was imaged to obtain the input image. Specifically, the imaging conditions obtaining unit 402 inputs the input image to the imaged location estimating engine, evaluates the probabilities that are output for each imaged site label of an imaged site label group, and sets and obtains the imaged site with the highest probability as an imaging condition of the input image.

Note that, in a case where imaging conditions other than the imaged site or imaged region are not stored in the input image, the imaging conditions obtaining unit 402 can obtain an imaging information group including an imaging conditions group from the imaging apparatus 10 or an image management system (not illustrated).

The subsequent processing is the same as in the series of image processing operations according to the second embodiment, and hence a description thereof is omitted here.

As described above, the imaging conditions obtaining unit 402 according to the present embodiment functions as an estimating unit that estimates at least one of an imaged site and an imaged region of an input image. The imaging conditions obtaining unit 402 includes an imaged location estimating engine which performed learning using images to each of which was attached a label of an imaged site or an imaged region as training data, and when an input image is input to the imaged location estimating engine, the imaged location estimating engine estimates the imaged site or imaged region of the input image.

Thus, the image processing apparatus 400 according to the present embodiment can obtain an imaging condition regarding the imaged site or imaged region of an input image, based on the input image.

Note that, in the present embodiment, in a case where information pertaining to an imaged site or imaged region is not included in the imaging conditions group, the imaging conditions obtaining unit 402 performs an estimation regarding the imaged site or imaged region of the input image using the imaged location estimating engine. However, a situation in which an estimation regarding an imaged site or imaged region is performed using the imaged location estimating engine is not limited to this situation. The imaging conditions obtaining unit 402 may also perform an estimation regarding an imaged site or imaged region using the imaged location estimating engine in a case where information regarding the imaged site or imaged region included in the data structure of the input image is insufficient as information of a required level of detail.

Further, irrespective of whether or not information regarding the imaged site or imaged region is included in the data structure of an input image, the imaging conditions obtaining unit 402 may estimate the imaged site or imaged region of the input image using the imaged location estimating engine. In this case, the outputting unit 405 may cause the display unit 20 to display an estimation result output from the imaged location estimating engine and information regarding the imaged site or imaged region included in the data structure of the input image, and the imaging conditions obtaining unit 402 may make determination regarding these imaging conditions in accordance with an instruction of the examiner.

Note that, similarly to the first embodiment, the outputting unit 405 may output a generated high quality image to the imaging apparatus 10 or to another apparatus connected to the image processing apparatus 400. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Fourth Embodiment

Next, an image processing apparatus according to a fourth embodiment is described referring to FIG. 4, FIG. 5, FIG. 8 and FIG. 9. In the present embodiment, an image quality improving unit enlarges or reduces an input image so that the size of the input image becomes an image size that the image quality improving engine is capable of handling. Further, the image quality improving unit generates a high quality image by reducing or enlarging an output image from the image quality improving engine so that the image size of the output image becomes the image size of the input image.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The image quality improving unit 404 according to the present embodiment includes an image quality improving engine that is similar to the image quality improving engine according to the first embodiment. However, in the present embodiment, a pair group of input data and ground truth constituted by an image group in which each image of the input data and each image of the ground truth is enlarged or reduced so as to be a certain image size is used as training data used for learning by the image quality improving engine.

Figure 8:
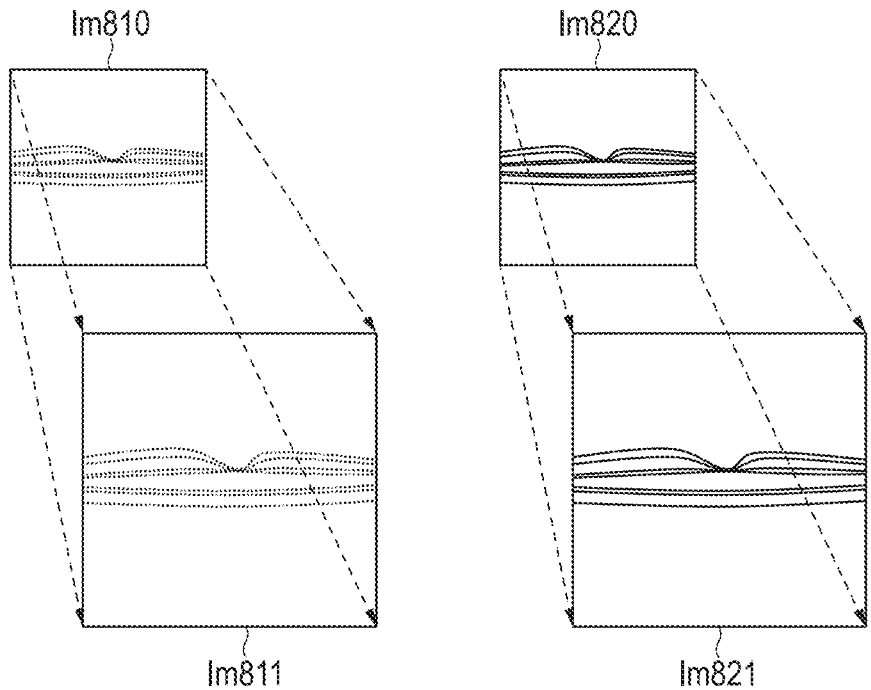
FIG. 8 is a view for describing image processing according to a fourth embodiment.

The training data of the image quality improving engine according to the present embodiment will now be described referring to FIG. 8. As illustrated in FIG. 8, for example, let us consider a case in which there are a low quality image Im810 and a high quality image Im820 which are smaller than a certain image size set with respect to the training data. In this case, the low quality image Im810 and the high quality image Im820 are each enlarged so as to become the certain image size set for the training data. The enlarged low quality image Im811 and the enlarged high quality image Im821 are then taken as a pair, and the relevant pair is used as one piece of training data.

Note that, similarly to the first embodiment, an image having specific imaging conditions assumed as a processing object (input image) is used for the input data of the training data, and the relevant specific imaging conditions are an imaged site, an imaging system and an imaging angle of view determined in advance. In other words, unlike the first embodiment, the image size is not included in the specific imaging conditions according to the present embodiment.

The image quality improving unit 404 according to the present embodiment generates a high quality image by improving the image quality of the input image using the image quality improving engine which performed learning using such training data. At such time, the image quality improving unit 404 generates a modified image by enlarging or reducing the input image so as to become a certain image size set with respect to the training data, and inputs the modified image to the image quality improving engine. Further, the image quality improving unit 404 generates a high quality image by reducing or enlarging an output image from the image quality improving engine so as to become the image size of the input image. Hence, even in the case of an input image having an image size that cannot be handled according to the first embodiment, the image quality improving unit 404 according to the present embodiment can generate a high quality image by improving the image quality of the input image by the image quality improving engine.

Figure 9:
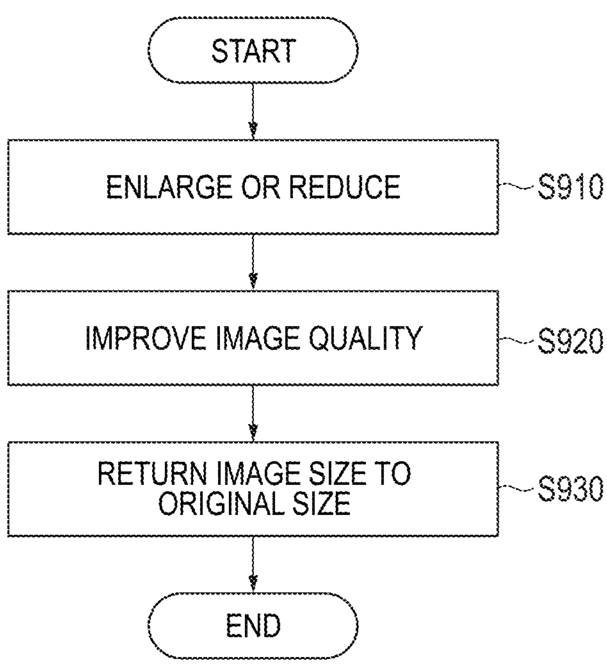
FIG. 9 is a flowchart illustrating an example of a flow of image quality improving processing according to the fourth embodiment.

Next, a series of image processing operations according to the present embodiment is described referring to FIG. 5 and FIG. 9. FIG. 9 is a flowchart illustrating image quality improving processing according to the present embodiment. Note that, the processing in step S510, step S520 and step S550 according to the present embodiment is the same as the processing in these steps in the first embodiment, and hence a description of the processing is omitted here. Note that, in a case where the image quality of an input image is to be improved unconditionally with regard to the imaging conditions other than the image size, after performing the processing in step S520, the processing in step S530 can be omitted and the processing can shift to step S540.

In step S520, similarly to the first embodiment, upon the imaging conditions obtaining unit 402 obtaining the imaging conditions group of the input image, the processing shifts to step S530. In step S530, the image quality improvement possibility determining unit 403 uses the obtained imaging conditions group to determine whether or not the image quality improving engine which the image quality improving unit 404 includes is capable of handling the input image. Specifically, with respect to the imaging conditions of the input image, the image quality improvement possibility determining unit 403 determines whether or not the imaged site, imaging system and imaging angle of view can be handled by the image quality improving engine. Unlike the first embodiment, the image quality improvement possibility determining unit 403 does not make determination regarding the image size.

The image quality improvement possibility determining unit 403 makes determination regarding the imaged site, imaging system and imaging angle of view, and if it is determined that the input image can be handled, the processing shifts to step S540. On the other hand, in a case where, based on these imaging conditions, the image quality improvement possibility determining unit 403 determines that the image quality improving engine is not capable of handling the input image, the processing shifts to step S550. Note that, depending on the settings or implementation form of the image processing apparatus 400, even if it is determined that the input image cannot be processed based on one or more conditions among the imaged site, imaging system and imaging angle of view, the image quality improving processing in step S540 may be performed.

Upon the processing shifting to step S540, image quality improving processing according to the present embodiment illustrated in FIG. 9 is started. In the image quality improving processing according to the present embodiment, first, in step S910, the image quality improving unit 404 enlarges or reduces the input image to a certain image size set with respect to the training data, to thereby generate a modified image.

Next, in step S920, the image quality improving unit 404 inputs the generated modified image to the image quality improving engine to obtain a modified image with high image quality subjected to image quality improving.

Thereafter, in step S930, the image quality improving unit 404 reduces or enlarges the modified image with high image quality to the image size of the input image to generate a high quality image. Upon the image quality improving unit 404 generating the high quality image in step S930, the image quality improving processing according to the present embodiment ends, and the processing shifts to step S550. Since the processing in step S550 is the same as the processing in step S550 of the first embodiment, a description thereof is omitted here.

As described above, the image quality improving unit 404 according to the present embodiment adjusts the image size of an input image to an image size which the image quality improving engine is capable of handling, and inputs the resultant image whose size was adjusted into the image quality improving engine. The image quality improving unit 404 generates a high quality image by adjusting the image size of the output image from the image quality improving engine to the original image size of the input image. Thus, the image processing apparatus 400 of the present embodiment can use the image quality improving engine to also improve the image quality of an input image having an image size that cannot be handled according to the first embodiment, and can thereby generate a high quality image suitable for image diagnosis.

Note that, similarly to the first embodiment, the outputting unit 405 may output a generated high quality image to the imaging apparatus 10 or to another apparatus connected to the image processing apparatus 400. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Fifth Embodiment

Next, an image processing apparatus according to a fifth embodiment is described referring to FIG. 4, FIG. 5, FIG. 10 and FIG. 11. In the present embodiment, the image quality improving unit generates a high quality image by image quality improving processing based on a certain resolution which is performed by an image quality improving engine.

Unless explicitly stated otherwise, the configuration and processing of the image processing apparatus according to the present embodiment are the same as the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The image quality improving unit 404 according to the present embodiment includes an image quality improving engine that is similar to the first embodiment. However, in the present embodiment, the training data used for learning by the image quality improving engine differs from the training data in the first embodiment. Specifically, after an image group composed of a pair group of input data and ground truth of the training data is enlarged or reduced to an image size such that the resolution of the image group becomes a certain resolution, padding is performed so that the image size of each image of the image group becomes a sufficiently large certain image size. Here, the phrase "resolution of the image group" refers to, for example, the spatial resolution of the imaging apparatus or the resolution with respect to an imaged region.

Figure 10:
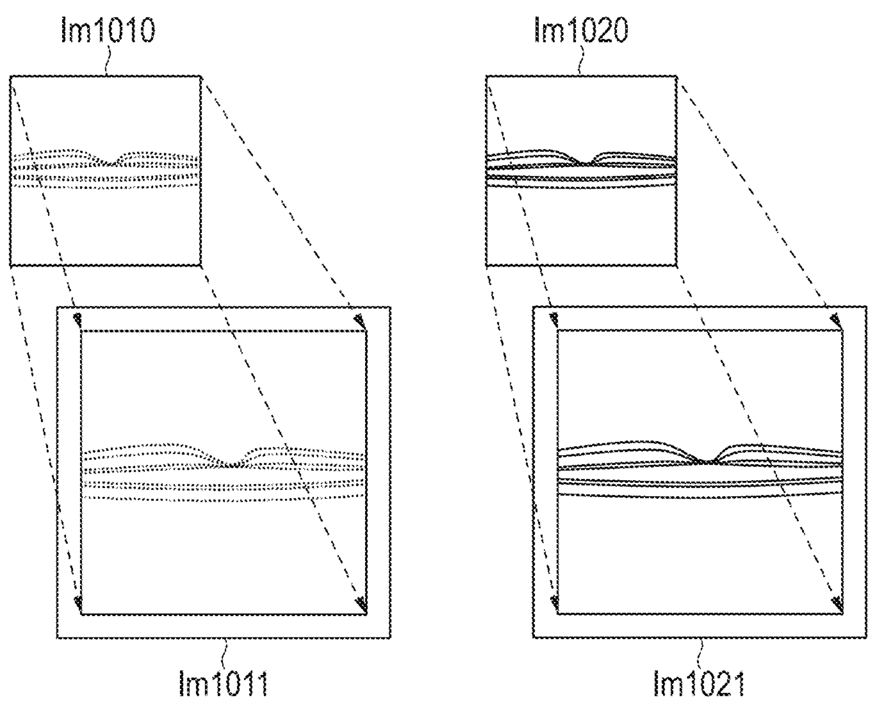
FIG. 10 is a view for describing image processing according to a fifth embodiment.

The training data of the image quality improving engine according to the present embodiment will now be described referring to FIG. 10. As illustrated in FIG. 10, for example, let us consider a case where there are a low quality image Im1010 and a high quality image Im1020 which have a lower resolution than a certain resolution set for the training data. In this case, the low quality image Im1010 and the high quality image Im1020 are each enlarged so that the resolution becomes the certain resolution set for the training data. In addition, the enlarged low quality image Im1010 and high quality image Im1020 are each padded so as to become a certain image size set for the training data. The low quality image Im1011 and high quality image Im1021 subjected to enlargement and padding are then taken as a pair, and the pair is used as one piece of training data.

Note that, the phrase "certain image size set for the training data" refers to the largest image size that an image assumed as a processing object (input image) can become when enlarged or reduced so that the resolution of the image becomes a certain resolution. In a case where the certain image size is not sufficiently large, there is a possibility that when an image input to the image quality improving engine is enlarged, the image will be an image size that the machine learning model is not capable of handling.

Further, a region subjected to padding is filled using a fixed pixel value, is filled using a neighboring pixel value, or is mirror-padded, in accordance with the characteristics of the machine learning model so that image quality improving can be effectively performed. Note that, similarly to the first embodiment, an image having specific imaging conditions assumed as a processing object is used for the input data, and the specific imaging conditions in question are an imaged site, an imaging system and an imaging angle of view determined in advance. In other words, unlike the first embodiment, the image size is not included in the specific imaging conditions according to the present embodiment.

The image quality improving unit 404 according to the present embodiment generates a high quality image by improving the image quality of the input image using the image quality improving engine which performed learning using such training data. At such time, the image quality improving unit 404 generates a modified image by enlarging or reducing the input image so as to become a certain resolution set with respect to the training data. Further, the image quality improving unit 404 performs padding with respect to the modified image so that the modified image becomes a certain image size set for the training data to thereby generate a padded image, and inputs the padded image to the image quality improving engine.

Further, with respect to a padded image with high image quality output from the image quality improving engine, the image quality improving unit 404 trims only a region corresponding to a region at which padding was performed, to thereby generate a modified image with high image quality. Thereafter, the image quality improving unit 404 reduces or enlarges the generated modified image with high image quality so as to be the image size of the input image, thereby generating a high quality image.

Hence, even in the case of an input image having an image size that cannot be handled according to the first embodiment, the image quality improving unit 404 according to the present embodiment can generate a high quality image by improving the image quality of the input image by the image quality improving engine.

Figure 11:
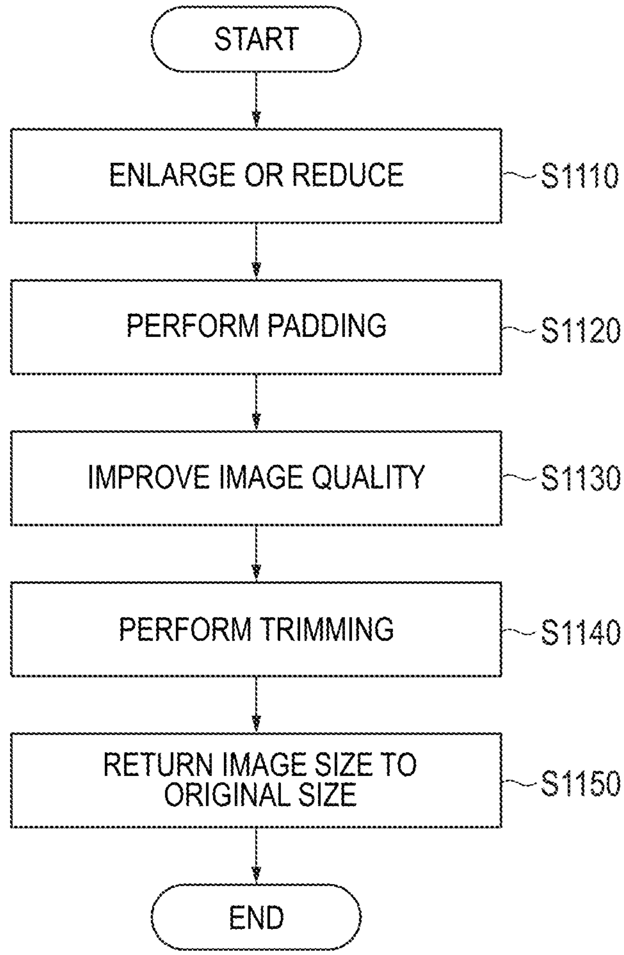
FIG. 11 is a flowchart illustrating an example of a flow of image quality improving processing according to the fifth embodiment.

Next, a series of image processing operations according to the present embodiment is described referring to FIG. 5 and FIG. 11. FIG. 11 is a flowchart illustrating image quality improving processing according to the present embodiment. Note that, the processing in step S510, step S520 and step S550 according to the present embodiment is the same as the processing in these steps in the first embodiment, and hence a description of the processing is omitted here. Note that, in a case where the image quality of an input image is to be improved unconditionally with regard to the imaging conditions other than the image size, after performing the processing in step S520, the processing in step S530 can be omitted and the processing can shift to step S540.

In step S520, similarly to the first embodiment, upon the imaging conditions obtaining unit 402 obtaining the imaging conditions group of the input image, the processing shifts to step S530. In step S530, the image quality improvement possibility determining unit 403 uses the obtained imaging conditions group to determine whether or not the image quality improving engine which the image quality improving unit 404 includes is capable of handling the input image. Specifically, with respect to the imaging conditions of the input image, the image quality improvement possibility determining unit 403 determines whether or not the imaged site, imaging system and imaging angle of view can be handled by the image quality improving engine. Unlike the first embodiment, the image quality improvement possibility determining unit 403 does not make determination regarding the image size.

The image quality improvement possibility determining unit 403 makes determination regarding the imaged site, imaging system and imaging angle of view, and if it is determined that the input image can be handled, the processing shifts to step S540. On the other hand, in a case where, based on these imaging conditions, the image quality improvement possibility determining unit 403 determines that the image quality improving engine is not capable of handling the input image, the processing shifts to step S550. Note that, depending on the settings or implementation form of the image processing apparatus 400, even if it is determined that the input image cannot be processed based on one or more conditions among the imaged site, imaging system and imaging angle of view, the image quality improving processing in step S540 may be performed.

Upon the processing shifting to step S540, image quality improving processing according to the present embodiment illustrated in FIG. 11 is started. In the image quality improving processing according to the present embodiment, first, in step S1110, the image quality improving unit 404 enlarges or reduces the input image so as to become a certain resolution set with respect to the training data, to thereby generate a modified image.

Next, in step S1120, the image quality improving unit 404 performs padding with respect to the generated modified image so that the modified image becomes an image size set for the training data, to thereby generate a padded image. At such time, with regard to a region in which padding is performed, the image quality improving unit 404 performs padding by filling the region using a fixed pixel value or using a neighboring pixel value or by mirror-padding in accordance with the characteristics of the machine learning model so that image quality improving can be effectively performed.

In step S1130, the image quality improving unit 404 inputs the padded image to the image quality improving engine to thereby obtain a padded image with high image quality subjected to image quality improving.

Next, in step S1140, with respect to the padded image with high image quality, the image quality improving unit 404 trims only a region corresponding to a region at which padding was performed in step S1120, to thereby generate a modified image with high image quality.

Thereafter, in step S1150, the image quality improving unit 404 reduces or enlarges the modified image with high image quality to the image size of the input image to generate a high quality image. Upon the image quality improving unit 404 generating the high quality image in step S1130, the image quality improving processing according to the present embodiment ends, and the processing shifts to step S550. Since the processing in step S550 is the same as the processing in step S550 of the first embodiment, a description of the processing is omitted here.

As described above, the image quality improving unit 404 according to the present embodiment adjusts the image size of an input image so that the resolution of the input image becomes a predetermined resolution. Further, with respect to the input image whose image size was adjusted, the image quality improving unit 404 generates a padded image subjected to padding so that the adjusted image size become an image size which the image quality improving engine is capable of handling, and then inputs the padded image to the image quality improving engine. Thereafter, the image quality improving unit 404 subjects an output image from the image quality improving engine to trimming so as to trim only a region corresponding to a region in which padding was performed. The image quality improving unit 404 then adjusts the image size of the image on which trimming was performed to the original image size of the input image, to thereby generate a high quality image.

Thus, even in the case of an input image having an image size that cannot be handled according to the first embodiment, the image quality improving unit 404 of the present embodiment can improve the image quality of the input image by the image quality improving engine to thereby generate a high quality image. Further, by using an image quality improving engine which learned with training data based on the resolution, in some cases the image quality of an input image can be improved more efficiently than in the case of the image quality improving engine according to the fourth embodiment that simply processes images of the same image size.

Note that, similarly to the first embodiment, the outputting unit 405 may output a generated high quality image to the imaging apparatus 10 or to another apparatus connected to the image processing apparatus 400. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Sixth Embodiment

Next, an image processing apparatus according to a sixth embodiment is described referring to FIG. 4, FIG. 5, FIG. 12 and FIG. 13. In the present embodiment, the image quality improving unit generates a high quality image by performing image quality improving processing of each region of a certain image size of an input image.

Unless explicitly stated otherwise, the configuration and processing of the image processing apparatus according to the present embodiment are the same as the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The image quality improving unit 404 according to the present embodiment includes a similar image quality improving engine to the first embodiment. However, in the present embodiment, the training data used for learning by the image quality improving engine differs from the training data in the first embodiment. Specifically, a pair group of input data that is a low quality image and ground truth that is a high quality image constituting the training data is constituted by rectangular region images of a certain image size whose positional relationships correspond in the low quality image and the high quality image. Note that, a rectangular region is one example of a partial region, and the partial region is not required to be rectangular and may be any shape.

Figure 12:
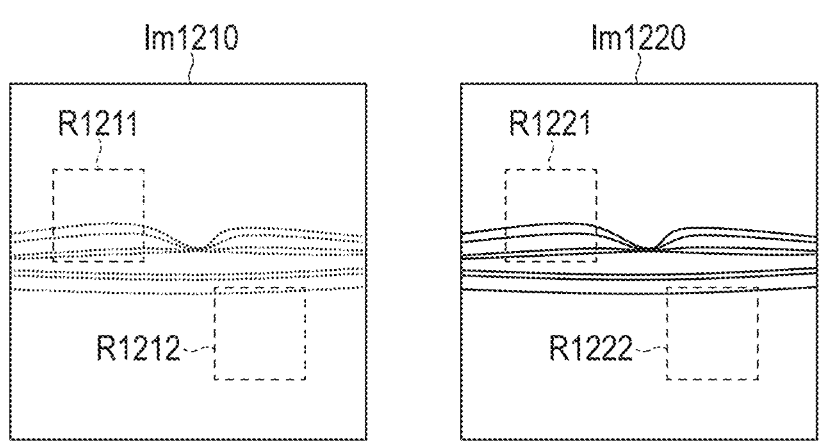
FIG. 12 is a view for describing image processing according to a sixth embodiment.

The training data of the image quality improving engine according to the present embodiment will now be described referring to FIG. 12. As illustrated in FIG. 12, a case will be considered in which, for example, there is a source image Im1210 that is a low quality image and an averaged image Im1220 that is a high quality image in one pair group constituting the training data. In this case, in the first embodiment, the source image Im1210 is adopted as the input data and the averaged image Im1220 is adopted as the ground truth of the training data.

In contrast, in the present embodiment, a rectangular region image R1211 in the source image Im1210 is adopted as the input data, and a rectangular region image R1221 which, in the averaged image Im1220, is the same imaged region as the rectangular region image R1211, is adopted as the ground truth. Further, a pair (hereinafter, referred to as a "first rectangular region image pair") of the training data is constituted by the rectangular region image R1211 that is the input data and the rectangular region image R1221 that is the ground truth. Here, it is assumed that the rectangular region image R1211 and the rectangular region image R1221 are images of a certain image size. Note that, the source image Im1210 and the averaged image Im1220 may be aligned by any method. Further, the positional relationship corresponding to the rectangular region image R1211 and the rectangular region image R1221 may be identified by any method such as template matching. Note that, depending on the design of the image quality improving engine, the respective image sizes and number of dimensions of the input data and the ground truth may differ from each other. For example, in a case where the processing object is an OCT image, when the input data is one part of a B-scan image (two-dimensional image), the ground truth may be one part of an A-scan image (one-dimensional image).

The certain image size relating to the rectangular region images R1211 and R1221 can be determined based on, for example, a common divisor of a group of the numbers of pixels of each dimension which corresponds to an image size group of images assumed as the processing object (input image). In this case, the positional relationships between a group of rectangular region images which the image quality improving engine outputs can be prevented from overlapping. Specifically, let us consider a case where, for example, the image assumed as a processing object is a two-dimensional image, a first image size in an image size group is a width of 500 pixels and a height of 500 pixels, and a second image size in the image size group is a width of 100 pixels and a height of 100 pixels. Here, the certain image size relating to the rectangular region images R1211 and R1221 is selected from the common divisors for each side. In this case, for example, the certain image size is selected from a width of 100 pixels and a height of 100 pixels, a width of 50 pixels and a height of 50 pixels, or a width of 25 pixels and a height of 25 pixels and the like.

In a case where the image assumed as the processing object has three dimensions, the number of pixels relating to the width, height and depth is determined. Note that, it is possible to set a plurality of rectangular regions for one pair of a low quality image corresponding to input data and a high quality image corresponding to ground truth. Therefore, for example, a rectangular region image R1212 in the source image Im1210 is adopted as input data, and a rectangular region image R1222 that, in the averaged image Im1220, is the same imaged region as the rectangular region image R1212 is adopted as ground truth. Further, a pair of the training data is composed of the rectangular region image R1212 as input data and the rectangular region image R1222 as ground truth. By this means, a rectangular region image pair that is different from the first rectangular region image pair can be created.

Note that, the content of a pair group constituting the training data can be enhanced by creating a large number of pairs of rectangular region images while changing the image of the rectangular region to images with different coordinates, and it can be expected that efficient image quality improving will be performed by an image quality improving engine which performed learning using the relevant training pairs. However, a configuration can be adopted so that pairs which do not contribute to image quality improving by the machine learning model are not added to the training data. For example, if the image quality of a rectangular region image created from a high quality image that is ground truth included in a pair is not suitable for diagnosis, there is a possibility that an image output by an image quality improving engine which performed learning using such training data will also have image quality that is not suitable for image diagnosis. Therefore, a pair including such kind of high quality image can be removed from the training data.

Further, for example, in a case where, between two rectangular region images forming a pair, there is a large difference in average intensity or intensity distribution between a rectangular region image created from a low quality image and a rectangular region image created from a high quality image, the pair in question can also be removed from the training data. If learning is performed using such kind of training data, there is a possibility that the image quality improving engine will output an image that is not suitable for image diagnosis that has an intensity distribution which differs greatly from the input image.

In addition, let us consider a case where, for example, between two rectangular region images forming a pair, there is a large difference with respect to the structure or position of the imaging target to be rendered between a rectangular region image created from a low quality image and a rectangular region image created from a high quality image. In this case, there is a possibility that an image quality improving engine which performed learning using such kind of training data will output an image that is not suitable for image diagnosis in which the structure or position of the imaging target differs greatly from the input image. Therefore, such kind of pairs can be removed from the training data.

Note that, similarly to the first embodiment, an image having specific imaging conditions assumed as a processing object is used for the input data of the training data, and the relevant specific imaging conditions are an imaged site, an imaging system and an imaging angle of view which are determined in advance. In other words, unlike the first embodiment, the image size is not included in the specific imaging conditions according to the present embodiment.

The image quality improving unit 404 according to the present embodiment generates a high quality image by improving the image quality of the input image using the image quality improving engine which performed learning using such training data. At such time, the image quality improving unit 404 divides the input image into a group of rectangular region images having a certain image size set for the training data, continuously and without gaps. The image quality improving unit 404 subjects each image in the rectangular region image group into which the input image was divided to image quality improving by the image quality improving engine, to thereby generate a group of rectangular region images with high image quality. Thereafter, the image quality improving unit 404 arranges the generated group of rectangular region images with high image quality in accordance with the positional relationship between the rectangular region images in the input image and combines the rectangular region images to thereby generate a high quality image. Here, when performing learning, if there is a corresponding positional relationship between the input data and the ground truth that form an image pair, a rectangular region of each of the input data and the ground truth may be cut out (extracted) from an arbitrary location in the low quality image and the high quality image. On the other hand, when improving the image quality, the input image may be divided into a rectangular region image group continuously and without gaps. Further, the image size of each pair of images at the time of learning, and the image size of each rectangular region image when performing image quality improving may be set so as to correspond to each other (for example, to be the same size). By this means, it is possible to ensure that, while improving the learning efficiency, a problem does not occur whereby an image is not obtained when insufficient parts or needless calculations arise.

Thus, by improving the image quality of an input image in rectangular region units and joining the images whose image quality was improved, the image quality improving unit 404 of the present embodiment can also generate a high quality image by improving the image quality of an image of an image size that cannot be handled according to the first embodiment.

Figure 13:
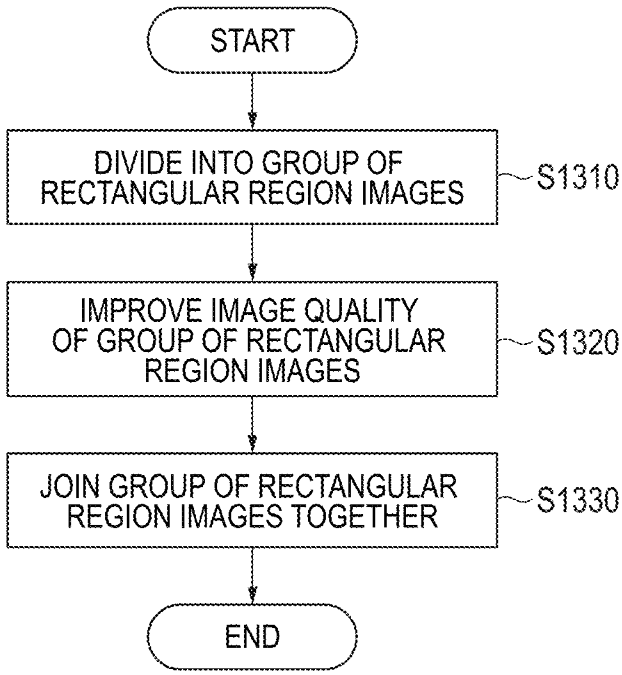
FIG. 13 is a flowchart illustrating an example of a flow of image quality improving processing according to the sixth embodiment.

Next, a series of image processing operations according to the present embodiment is described referring to FIG. 5, FIG. 13 and FIG. 14A to FIG. 14D. FIG. 13 is a flowchart illustrating image quality improving processing according to the present embodiment. Note that, the processing in step S510, step S520 and step S550 according to the present embodiment is the same as the processing in these steps in the first embodiment, and hence a description of the processing is omitted here. Note that, in a case where the image quality of an input image is to be improved unconditionally with regard to the imaging conditions other than the image size, after performing the processing in step S520, the processing in step S530 can be omitted and the processing can shift to step S540.

In step S520, similarly to the first embodiment, upon the imaging conditions obtaining unit 402 obtaining the imaging conditions group of the input image, the processing shifts to step S530. In step S530, the image quality improvement possibility determining unit 403 uses the obtained imaging conditions group to determine whether or not the image quality improving engine which the image quality improving unit 404 includes is capable of handling the input image. Specifically, with respect to the imaging conditions of the input image, the image quality improvement possibility determining unit 403 determines whether or not the imaged site, imaging system and imaging angle of view can be handled by the image quality improving engine. Unlike the first embodiment, the image quality improvement possibility determining unit 403 does not make determination regarding the image size.

The image quality improvement possibility determining unit 403 makes determination regarding the imaged site, imaging system and imaging angle of view, and if it is determined that the input image can be handled, the processing shifts to step S540. On the other hand, in a case where, based on these imaging conditions, the image quality improvement possibility determining unit 403 determines that the image quality improving engine is not capable of handling the input image, the processing shifts to step S550. Note that, depending on the settings or implementation form of the image processing apparatus 400, even if it is determined that the input image cannot be processed based on one or more conditions among the imaged site, imaging system and imaging angle of view, the image quality improving processing in step S540 may be performed.

Figure 14A:
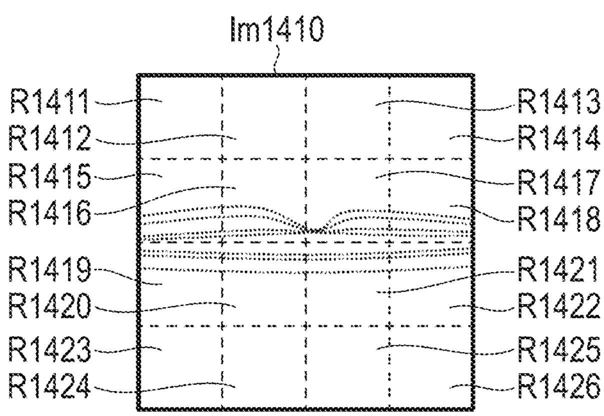
FIG. 14A is a view for describing image processing according to the sixth embodiment.
Figure 14B:
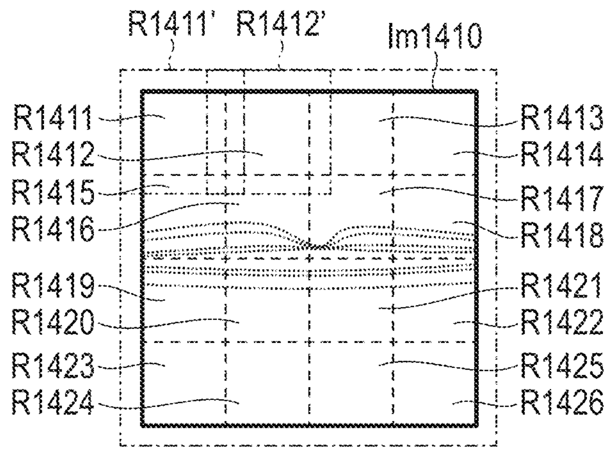
FIG. 14B is a view for describing image processing according to the sixth embodiment.
Figure 14C:
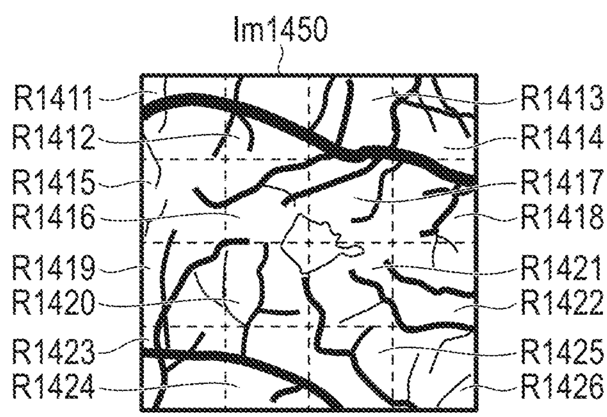
FIG. 14C is a view for describing image processing according to the sixth embodiment.
Figure 14D:
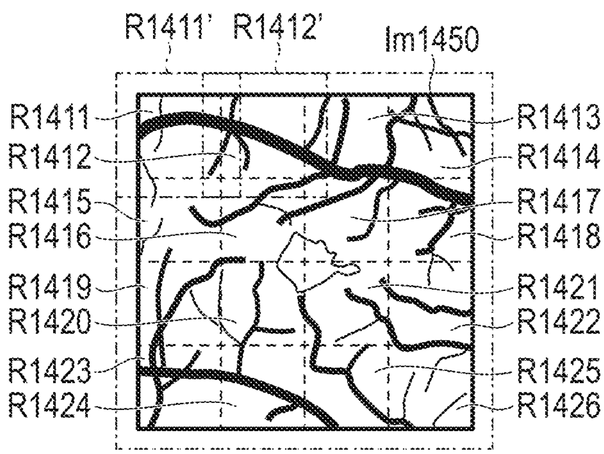
FIG. 14D is a view for describing image processing according to the sixth embodiment.

When the processing shifts to step S540, image quality improving processing according to the present embodiment illustrated in FIG. 13 is started. This processing will now be described using FIG. 14A to FIG. 14D. In the image quality improving processing according to the present embodiment, first, in step S1310, as illustrated in FIG. 14A, the input image is divided continuously and without gaps into a group of rectangular region images of a certain image size set for the training data (size illustrated by R1411). FIG. 14A illustrates one example of an input image Im1410 divided into a group of rectangular region images R1411 to R1426 of a certain image size. Note that, as mentioned above, depending on the design of the image quality improving engine, the image input to the image quality improving engine and the image output from the image quality improving engine may differ from each other with respect to the image size or the number of dimensions. In this case, to ensure there is no loss with respect to the joined high quality image generated in step S1320, the positions at which the input image is divided can be adjusted by causing the positions to overlap or by separating the positions. FIG. 14B illustrates an example in which the positions at which the input image is divided are caused to overlap. In FIG. 14B, reference characters R1411' and R1412' denote overlapping regions. Although not illustrated to avoid complicating the drawing, it is assumed that R1413 to R1426 have similar overlapping regions R1413' to R1426'. Note that, the rectangular region size set with respect to the training data in the case of FIG. 14B is the size shown in R1411'. Because no data exists in the outer periphery of the image (upper, lower, left and right edges) of the input image Im1410, padding is performed by filling with a fixed pixel value, by filling with a neighboring pixel value or by mirror-padding. Further, depending on the image quality improving engine, in some cases the accuracy of image quality improving decreases at the inner periphery of the image (upper, lower, left and right edges) due to filter processing. Therefore, the rectangular region images may be set so that the positions at which the image is divided overlap as in the example illustrated in FIG. 14B, and the rectangular region images may be trimmed at one part and then be combined to obtain the final image. The size of the rectangular region is set in accordance with the characteristics of the image quality improving engine. Note that, although an OCT tomographic image is illustrated as an example in FIG. 14A and FIG. 14B, as illustrated in FIG. 14C and FIG. 14D an input image (Im1450) may be a front image such as an OCTA en-face image, and it is possible to perform similar processing thereon. Note that, setting of the size of the rectangular region image is appropriately performed according to the image that is the processing object and the kind of the image quality improving engine.

Next, in step S1320, the image quality improving unit 404 uses the image quality improving engine to improve the image quality of each of the group of rectangular region images R1411 to R1426, or in a case where overlapping regions are set, the group of rectangular region images R1411' to R1426', and thereby generates a group of rectangular region images with high image quality.

Subsequently, in step S1330, the image quality improving unit 404 generates a high quality image by arranging and combining each of the rectangular region images in the generated group of rectangular region images with high image quality according to the same positional relationship as that of the group of rectangular region images R1411 to R1426 obtained by dividing the input image. In a case where overlapping regions are set, the image quality improving unit 404 generates a high quality image by cutting out and combining the rectangular region images R1411 to R1426 after the images are arranged according to the same positional relationship as the respective rectangular region images R1411' to R1426'. Note that, a configuration may be adopted so as to correct the intensity values of the rectangular region images R1411' to R1426' utilizing the overlapping regions. For example, a rectangular region image to be taken as a reference is arbitrarily set. Then, by measuring the intensity value of the same coordinate points in an adjacent rectangular image having a region overlapping with the reference rectangular image, a difference (ratio) between the intensity values of the adjacent images can be found. Similarly, by determining the difference (ratio) between intensity values at the overlapping regions in all of the images, it is possible to perform correction so as to eliminate unevenness between the intensity values as a whole. Note that, it is not necessary to use the entire overlapping region for intensity value correction, and a part (the number of pixels at the periphery) of the overlapping region need not be used.

As mentioned above, the image quality improving unit 404 according to the present embodiment divides an input image into a plurality of rectangular region images (third images) R1411 to R1426 of a predetermined image size. Thereafter, the image quality improving unit 404 inputs the divided plurality of rectangular region images R1411 to R1426 to the image quality improving engine to generate a plurality of fourth images, and then integrates the plurality of fourth images to generate a high quality image. Note that, in a case where positional relationships among the group of rectangular region overlap during integration, a pixel value group of the rectangular region group can be integrated or overwritten.

Thus, even in the case of an input image having an image size that cannot be handled according to the first embodiment, the image quality improving unit 404 of the present embodiment can improve the image quality of the input image by the image quality improving engine and can thereby generate a high quality image. Further, by creating training data from a plurality of images obtained by dividing a low quality image and a high quality image into a predetermined image size, a large amount of training data can be created from a small number of images. Hence, in this case, the number of low quality images and high quality images used for creating training data can be reduced.

Note that, similarly to the first embodiment, the outputting unit 405 may output a generated high quality image to the imaging apparatus 10 or to another apparatus connected to the image processing apparatus 400. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Seventh Embodiment

Next, an image processing apparatus according to a seventh embodiment will be described referring to FIG. 15 to FIG. 17. In the present embodiment, in accordance with an instruction of the examiner, an image quality evaluating unit selects an image with the highest image quality among a plurality of high quality images output from a plurality of image quality improving engines.

Unless explicitly stated otherwise, the configuration and processing of the image processing apparatus according to the present embodiment are the same as the image processing apparatus 400 according to the first embodiment. Therefore, hereunder, the image processing apparatus according to the present embodiment is described centering on differences from the image processing apparatus according to the first embodiment.

Figure 15:
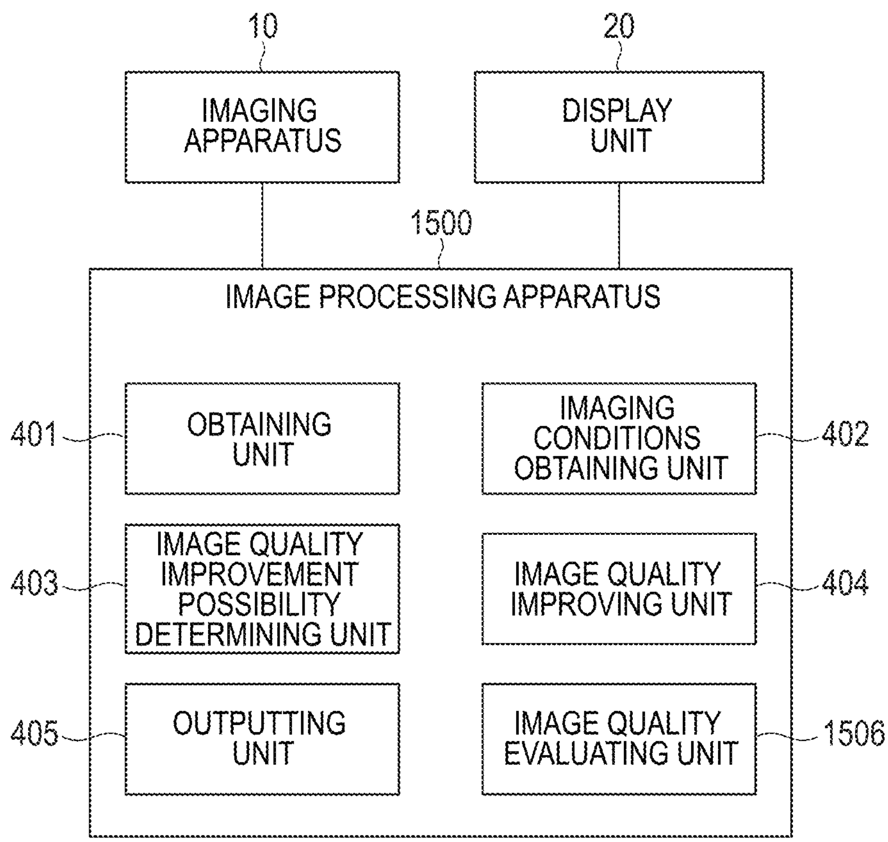
FIG. 15 is a view illustrating an example of a schematic configuration of an image processing apparatus according to a seventh embodiment.

FIG. 15 is a diagram illustrating a schematic configuration of an image processing apparatus 1500 according to the present embodiment. The image processing apparatus 1500 according to the present embodiment is provided with an image quality evaluating unit 1506 in addition to the obtaining unit 401, the imaging conditions obtaining unit 402, the image quality improvement possibility determining unit 403, the image quality improving unit 404 and the outputting unit 405. Note that, the image processing apparatus 1500 may be constituted by a plurality of apparatuses which are each provided with one or more of these components. Here, since the configuration with respect to the obtaining unit 401, the imaging conditions obtaining unit 402, the image quality improvement possibility determining unit 403, the image quality improving unit 404 and the outputting unit 405 is the same as the configuration of the image processing apparatus according to the first embodiment, components illustrated in FIG. 4 are denoted by the same reference numerals as in the first embodiment, and a description of the components is omitted hereunder.

Further, similarly to the image processing apparatus 400 according to the first embodiment, the image processing apparatus 1500 may be connected through any circuit or network to the imaging apparatus 10, the display unit 20 and another apparatus (not illustrated). Further, these apparatuses may be connected through a circuit or network to any other apparatuses, and may be constituted integrally with any other apparatus. Note that, although in the present embodiment these apparatuses are assumed to be separate apparatuses to each other, some or all of these apparatuses may be constituted integrally with each other.

The image quality improving unit 404 according to the present embodiment includes two or more image quality improving engines which performed machine learning using different training data to each other. A method for creating a training data group according to the present embodiment will now be described. Specifically, first, a group of pairs that each include input data that is a low quality image and ground truth that is a high quality image obtained by imaging according to various kinds of imaging conditions are prepared. Next, a training data group is created by grouping pair groups according to combinations of arbitrary imaging conditions. For example, a training data group is created that includes first training data composed of a pair group obtained according to a first combination of imaging conditions, and second training data composed of a pair group obtained according to a second combination of imaging conditions.

Thereafter, the respective image quality improving engines are caused to perform machine learning using the respective sets of training data. For example, an image quality improving engine group is prepared that includes a first image quality improving engine corresponding to a machine learning model trained using the first training data, and a second image quality improving engine corresponding to a machine learning model trained using the second training data.

Because different training data is used for training the respective machine learning models corresponding to each of these image quality improving engines, the degree to which each of these image quality improving engines can improve the image quality of an input image input to the image quality improving engines will differ according to the imaging conditions of the input image. Specifically, in the case of the first image quality improving engine, the degree of image quality improving with respect to an input image obtained by imaging using the first combination of imaging conditions is high, and the degree of image quality improving with respect to an image obtained by imaging using the second combination of imaging conditions is low. Similarly, in the case of the second image quality improving engine, the degree of image quality improving with respect to an input image obtained by imaging using the second combination of imaging conditions is high, and the degree of image quality improving with respect to an image obtained by imaging using the first combination of imaging conditions is low.

Because each set of training data is composed of a pair group grouped according to a combination of imaging conditions, there will be a similar image quality tendency among the images in an image group constituting the relevant pair group. Therefore, if the combination of imaging conditions corresponds to the training data used for training the relevant image quality improving engine, the relevant image quality improving engine can perform image quality improving more effectively than the image quality improving engine according to the first embodiment. Note that, a combination of imaging conditions for grouping pairs of the training data may be any combination of imaging conditions, and for example may be a combination of two or more imaging conditions among the group consisting of the imaged site, the imaging angle of view and the resolution of the image. Further, grouping of the training data may be performed based on a single imaging condition, similarly to the second embodiment.

In response to an instruction of the examiner, the image quality evaluating unit 1506 selects a high quality image with the highest image quality among the plurality of high quality images which the image quality improving unit 404 generated using the plurality of image quality improving engines.

The outputting unit 405 can cause the display unit 20 to display the high quality image that the image quality evaluating unit 1506 selected, or can output the high quality image to another apparatus. Note that, the outputting unit 405 can cause the display unit 20 to display a plurality of high quality images which the image quality improving unit 404 generated, and the image quality evaluating unit 1506 can select a high quality image with the highest image quality in accordance with an instruction from the examiner who checked the images on the display unit 20.

Thus, the image processing apparatus 1500 can output a high quality image with the highest image quality in accordance with an instruction of the examiner from among the plurality of high quality images generated using the plurality of image quality improving engines.

Figure 16:
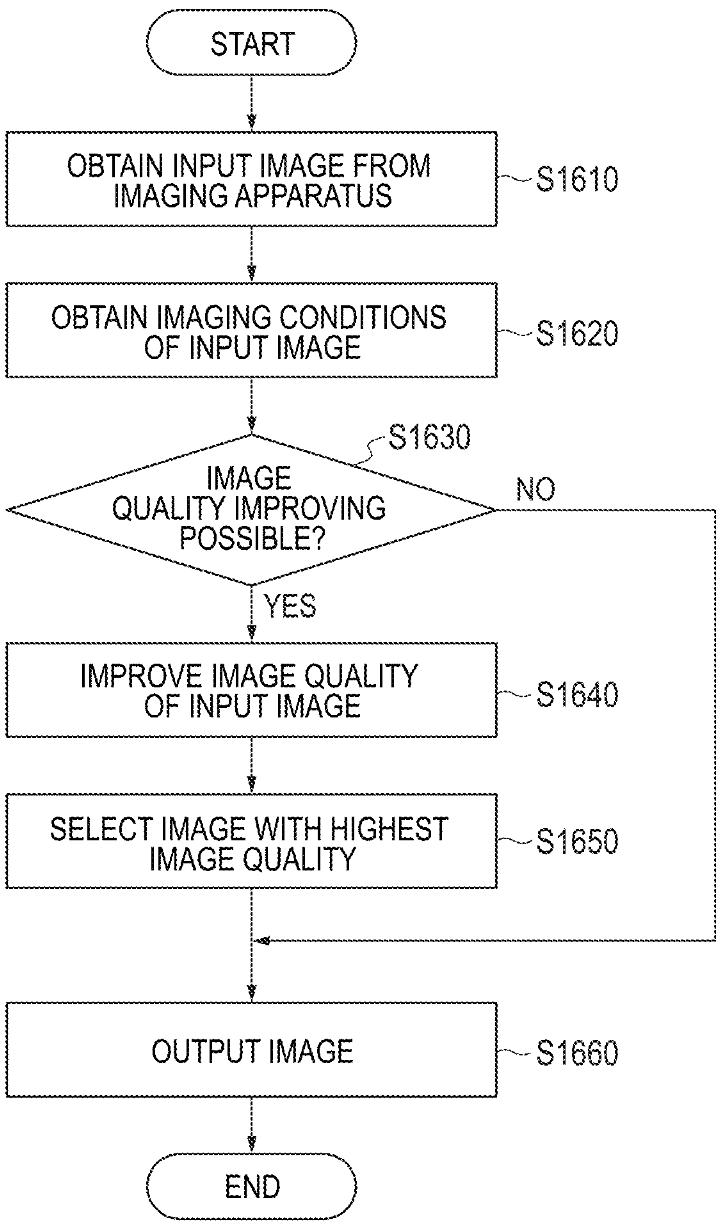
FIG. 16 is a flowchart illustrating an example of a flow of image processing according to the seventh embodiment.
Figure 17:
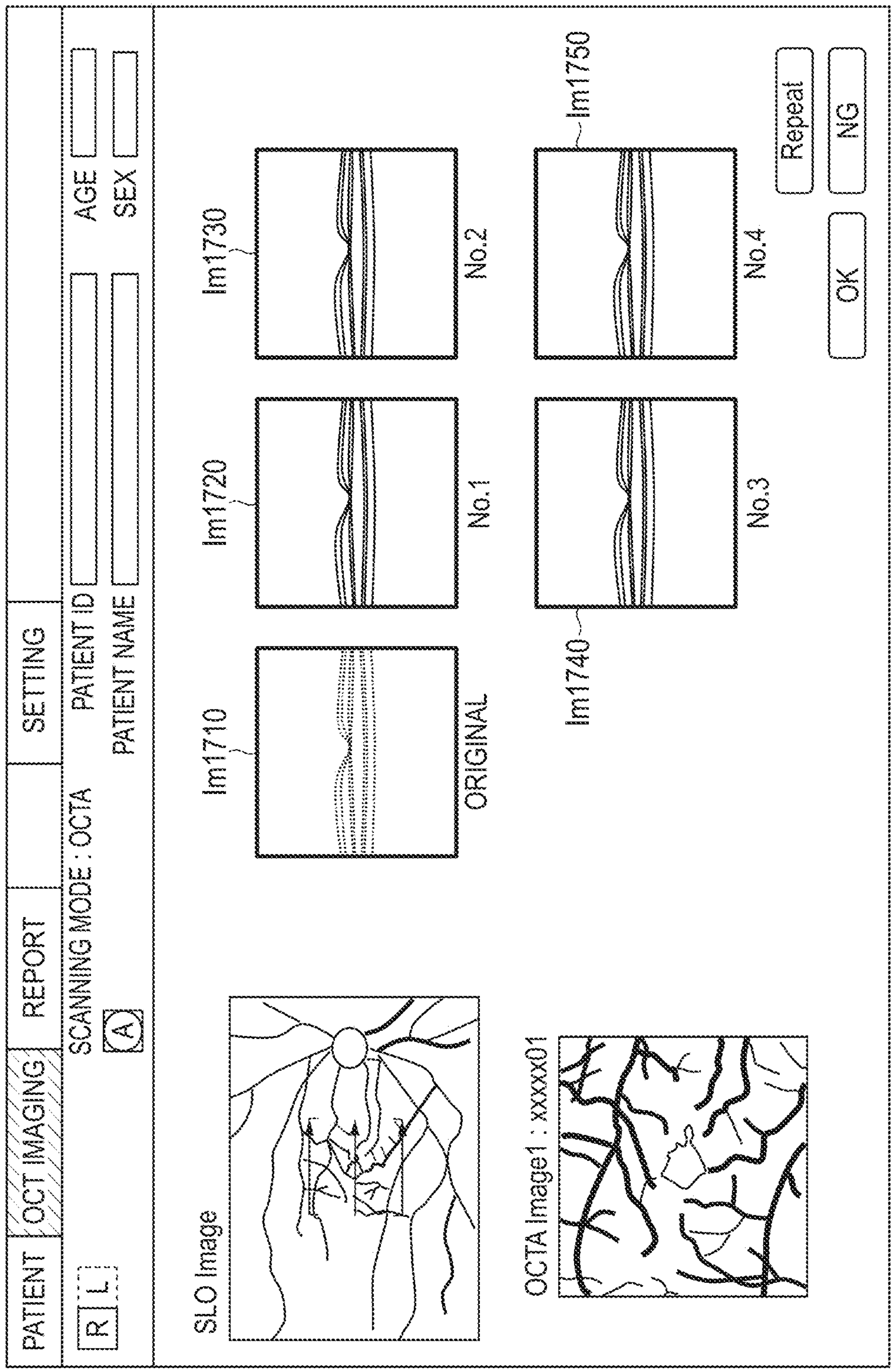
FIG. 17 is a view illustrating an example of a user interface according to the seventh embodiment.

Hereunder, a series of image processing operations according to the present embodiment is described referring to FIG. 16 and FIG. 17. FIG. 16 is a flowchart illustrating the series of image processing operations according to the present embodiment. Note that, the processing in step S1610 and step S1620 according to the present embodiment is the same as the processing in step S510 and step S520 in the first embodiment, and hence a description of the processing is omitted here. Note that, in a case where the image quality of an input image is to be improved unconditionally with regard to the imaging conditions, after performing the processing in step S1620, the processing in step S1630 can be omitted and the processing can shift to step S1640.

In step S1620, similarly to the first embodiment, upon the imaging conditions obtaining unit 402 obtaining the imaging conditions group of the input image, the processing shifts to step S1630. In step S1630, similarly to the second embodiment, the image quality improvement possibility determining unit 403 uses the obtained imaging conditions group to determine whether or not any of the image quality improving engines which the image quality improving unit 404 includes can handle the input image.

If the image quality improvement possibility determining unit 403 determines that none of the group of image quality improving engines is capable of handling the input image, the processing shifts to step S1660. On the other hand, if the image quality improvement possibility determining unit 403 determines that any of the group of image quality improving engines is capable of handling the input image, the processing shifts to step S1640. Note that, depending on the settings or implementation form of the image processing apparatus 1500, similarly to the first embodiment, even if it is determined that some of the imaging conditions cannot be handled by any of the image quality improving engines, the processing in step S1640 may be executed.

In step S1640, the image quality improving unit 404 inputs the input image obtained in step S1610 to each of the group of image quality improving engines, to thereby generate a high quality image group.

In step S1650, the image quality evaluating unit 1506 selects the image with the highest image quality among the high quality image group generated in step S1640. Specifically, first, the outputting unit 405 causes the high quality image group generated in step S1640 to be displayed on a user interface of the display unit 20.

An example of the interface in this case is illustrated in FIG. 17. An input image Im1710, and high quality images Im1720, Im1730, Im1740 and Im1750 output by the respective image quality improving engines of the image quality improving engine group are displayed on the interface. The examiner operates an arbitrary input apparatus (not illustrated) to instruct an image with the highest image quality, that is, the image that is most suitable for image diagnosis among the image group (high quality images Im1720 to Im1750). Note that, since there is also a possibility that the input image which has not been subjected to image quality improving by the image quality improving engines is suitable for image diagnosis, the input image may be added to the image group that is the object of the instruction by the examiner.

Thereafter, the image quality evaluating unit 1506 selects the high quality image instructed by the examiner, as the image with the highest image quality.

In step S1660, the outputting unit 405 causes the image selected in step S1650 to be displayed on the display unit 20 or outputs the image to another apparatus. However, if it was determined in step S1630 that it is not possible to process the input image, the outputting unit 405 outputs the input image as the output image. Note that, in a case where the examiner instructed that the input image be selected or a case where it is not possible to process the input image, the outputting unit 405 may cause the display unit 20 to display information indicating that the output image is the same as the input image.

As described above, the image quality improving unit 404 according to the present embodiment generates a plurality of high quality images from an input image using a plurality of image quality improving engines, and the outputting unit 405 of the image processing apparatus 1500 outputs at least one image among the plurality of high quality images in accordance with an instruction of the examiner. In particular, in the present embodiment, the outputting unit 405 outputs the image with the highest image quality in accordance with an instruction of the examiner. By this means, the image processing apparatus 1500 can output a high quality image which has high image quality in accordance with an instruction of the examiner from among a plurality of high quality images generated using a plurality of image quality improving engines.

Note that, similarly to the first embodiment, the outputting unit 405 may output a generated high quality image to the imaging apparatus 10 or to another apparatus connected to the image processing apparatus 1500. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Eighth Embodiment

Next, an image processing apparatus according to an eighth embodiment will be described referring to FIG. 15 and FIG. 16. In the present embodiment, an image quality evaluating unit uses an image quality evaluating engine to select an image with the highest image quality among a plurality of high quality images output from a plurality of image quality improving engines.

Unless explicitly stated otherwise, the configuration and processing of the image processing apparatus according to the present embodiment are the same as the image processing apparatus 1500 according to the seventh embodiment. Therefore, hereunder, the image processing apparatus according to the present embodiment is described centering on differences from the image processing apparatus according to the seventh embodiment. Note that, since the configuration of the image processing apparatus according to the present embodiment is the same as the configuration of the image processing apparatus according to the seventh embodiment, components of the configuration illustrated in FIG. 15 are denoted by the same reference numerals as in the seventh embodiment, and a description of the components is omitted hereunder.

The image quality evaluating unit 1506 according to the present embodiment includes an image quality evaluating engine for evaluating the image quality of an input image. The image quality evaluating engine outputs an image quality evaluation index with respect to an input image. An image quality evaluation processing technique that calculates an image quality evaluation index in the image quality evaluating engine according to the present embodiment uses a machine learning model built using a machine learning algorithm. The input data of pairs constituting training data for training the machine learning model is an image group composed of a low quality image group and a high quality image group imaged beforehand according to various imaging conditions. Further, the ground truth of the pairs constituting the training data for training the machine learning model is, for example, an image quality evaluation index group which the examiner who performs the image diagnosis set with respect to each image group of the input data.

Next, a series of image processing operations according to the present embodiment is described referring to FIG. 16. Note that, the processing in step S1610, step S1620, step S1630 and step S1660 according to the present embodiment is the same as the processing in these steps in the seventh embodiment, and hence a description of the processing is omitted here. Note that, in a case where the image quality of an input image is to be improved unconditionally with regard to the imaging conditions, after performing the processing in step S1620, the processing in step S1630 can be omitted and the processing can shift to step S1640.

In step S1630, similarly to the seventh embodiment, if the image quality improvement possibility determining unit 403 determines that any of the group of image quality improving engines is capable of handling the input image, the processing shifts to step S1640. Note that, depending on the settings or implementation form of the image processing apparatus 1500, similarly to the first embodiment, even if it is determined that some of the imaging conditions cannot be handled by any of the image quality improving engines, the processing in step S1640 may be executed.

In step S1640, the image quality improving unit 404 inputs the input image obtained in step S1610 to each of the group of image quality improving engines, to thereby generate a high quality image group.

In step S1650, the image quality evaluating unit 1506 selects the image with the highest image quality among the high quality image group generated in step S1640. Specifically, first, the image quality evaluating unit 1506 inputs the high quality image group generated in step S1640 to the image quality evaluating engine. The image quality evaluating engine calculates an image quality evaluation index based on learning, for each input high quality image. The image quality evaluating unit 1506 selects the high quality image for which the highest image quality evaluation index was calculated among the calculated image quality evaluation indexes. Note that, since there is also a possibility that the input image which was not subjected to image quality improving by an image quality improving engine is suitable for image diagnosis, the image quality evaluating unit 1506 may also input the input image to the image quality evaluating engine and add the image quality evaluation index for the input image to the selection. Since step S1660 is the same as step S1660 of the seventh embodiment, a description thereof is omitted here.

As described above, the image processing apparatus 1500 according to the present embodiment further includes the image quality evaluating unit 1506 that evaluates the image quality of a high quality image. The image quality improving unit 404 uses a plurality of image quality improving engines to generate a plurality of high quality images from an input image, and the outputting unit 405 of the image processing apparatus 1500 outputs at least one image among the plurality of high quality images in accordance with the result of evaluation by the image quality evaluating unit 1506. In particular, the image quality evaluating unit 1506 according to the present embodiment includes an image quality evaluating engine that used evaluation values obtained according to a predetermined evaluation technique as training data. The image quality evaluating unit 1506 selects a high quality image for which the result of an evaluation using the image quality evaluating engine by the image quality evaluating unit 1506 is highest among a plurality of high quality images. The outputting unit 405 outputs the high quality image having the highest evaluation value selected by the image quality evaluating unit 1506.

Thus, the image processing apparatus 1500 according to the present embodiment can easily output a high quality image that is most suitable for image diagnosis from among a plurality of high quality images, based on the output of the image quality evaluating engine.

Note that, in the present embodiment, the image quality evaluating unit 1506 selects a high quality image having the highest image quality evaluation index among image quality evaluation indexes output by the image quality evaluating engine, and the outputting unit 405 causes the display unit 20 to display the selected high quality image. However, the configuration of the image quality evaluating unit 1506 is not limited thereto. For example, the image quality evaluating unit 1506 may select several high quality images for which the image quality evaluation indexes are high among the image quality evaluation indexes output by the image quality evaluating engine, and the outputting unit 405 may cause the selected high quality images to be displayed on the display unit 20. Further, the outputting unit 405 may cause the image quality evaluation indexes output by the image quality evaluating engine to be displayed together with the corresponding high quality images on the display unit 20, and the image quality evaluating unit 1506 may select an image with the highest image quality in accordance with an instruction from the examiner.

Note that, similarly to the first embodiment, the outputting unit 405 may output a generated high quality image to the imaging apparatus 10 or to another apparatus connected to the image processing apparatus 1500. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, high-cost processing, and noise reduction processing.

Ninth Embodiment

Figure 18:
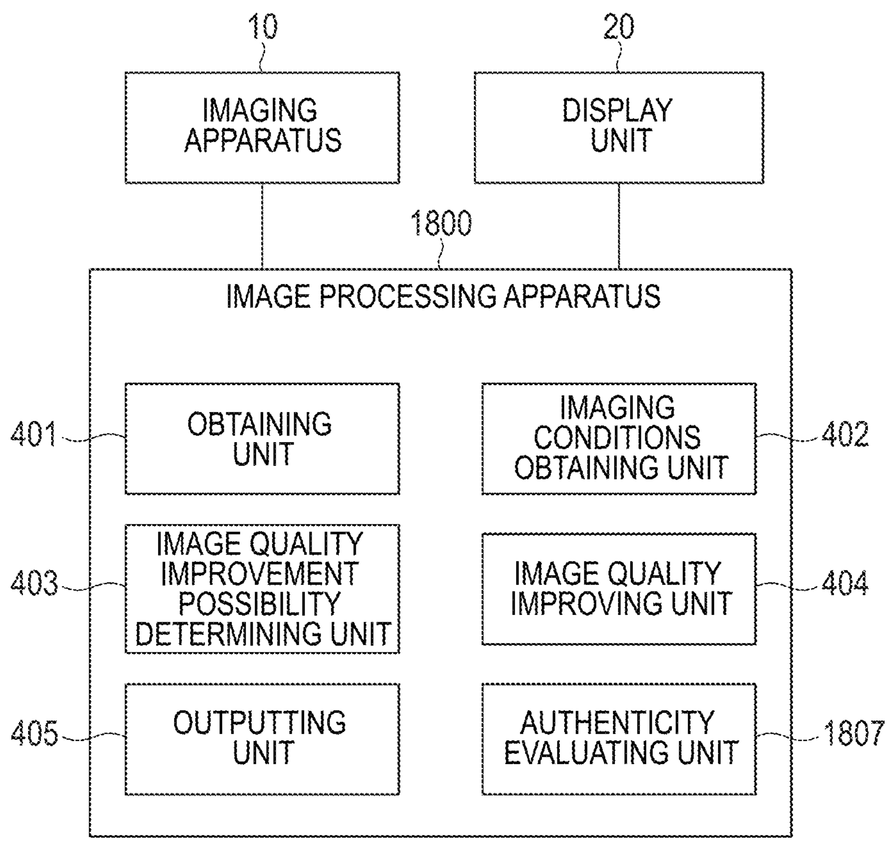
FIG. 18 is a view illustrating an example of the schematic configuration of an image processing apparatus according to a ninth embodiment.
Figure 19:
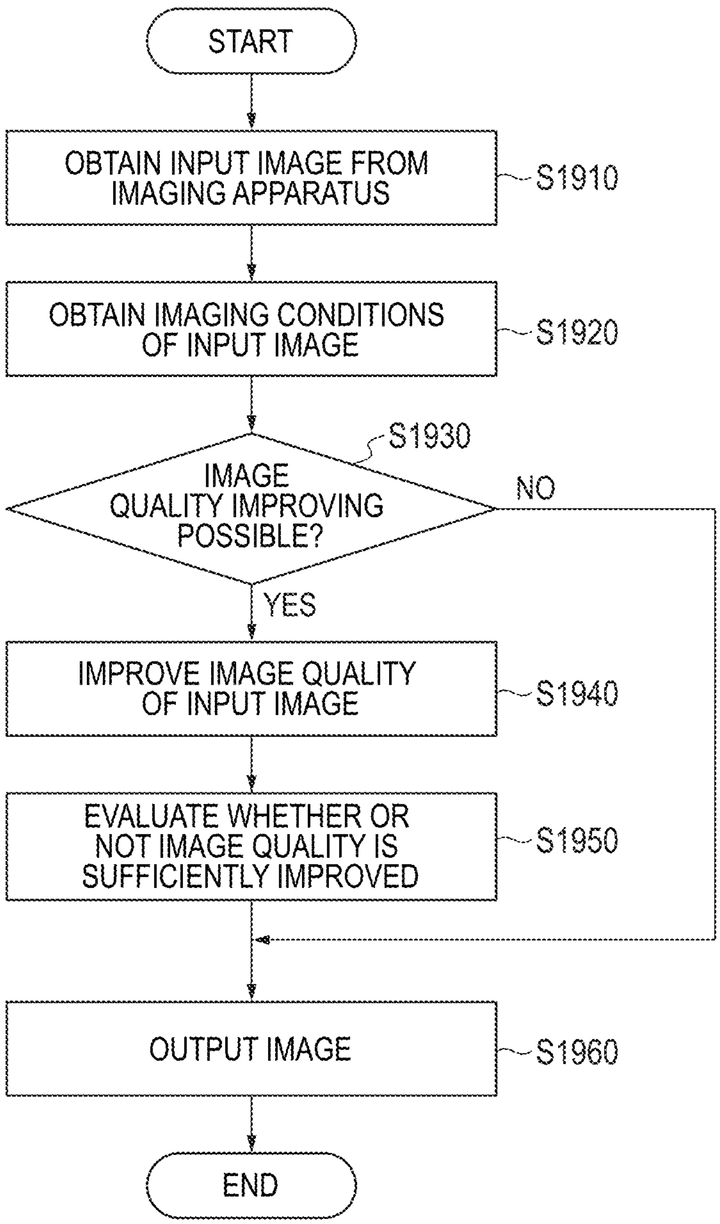
FIG. 19 is a flowchart illustrating an example of a flow of image processing according to the ninth embodiment.

Next, an image processing apparatus according to a ninth embodiment is described referring to FIG. 18 and FIG. 19. In the present embodiment, an authenticity evaluating unit uses an authenticity evaluating engine to evaluate whether or not a high quality image generated by the image quality improving unit 404 was subjected to sufficient image quality improving.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment.

FIG. 18 illustrates a schematic configuration of an image processing apparatus 1800 according to the present embodiment. The image processing apparatus 1800 according to the present embodiment is provided with an authenticity evaluating unit 1807 in addition to the obtaining unit 401, the imaging conditions obtaining unit 402, the image quality improvement possibility determining unit 403, the image quality improving unit 404 and the outputting unit 405. Note that, the image processing apparatus 1800 may be constituted by a plurality of apparatuses which are each provided with one or more of these components. Here, since the configuration with respect to the obtaining unit 401, the imaging conditions obtaining unit 402, the image quality improvement possibility determining unit 403, the image quality improving unit 404 and the outputting unit 405 is the same as the configuration of the image processing apparatus according to the first embodiment, components illustrated in FIG. 4 are denoted by the same reference numerals as in the first embodiment, and a description of the components is omitted hereunder.

Further, similarly to the image processing apparatus 400 according to the first embodiment, the image processing apparatus 1800 may be connected through any circuit or network to the imaging apparatus 10, the display unit 20 and other apparatuses (not illustrated). Further, these apparatuses may be connected through a circuit or network to any other apparatuses, and may be constituted integrally with any other apparatus. Note that, although in the present embodiment these apparatuses are assumed to be separate apparatuses to each other, some or all of these apparatuses may be constituted integrally with each other.

The authenticity evaluating unit 1807 includes an authenticity evaluating engine. The authenticity evaluating unit 1807 uses the authenticity evaluating engine to evaluate whether or not a high quality image that the image quality improving engine generated has been subjected to sufficient image quality improving. An authenticity evaluation processing technique used by the authenticity evaluating engine according to the present embodiment uses a machine learning model built using a machine learning algorithm.

The training data used to train the machine learning model includes a pair group composed of a high quality image group imaged beforehand according to various imaging conditions and a label (hereinafter, referred to as a "real label") indicating that the relevant image was obtained by imaging by the target imaging apparatus. Further, the training data includes a pair group composed of a high quality image group generated by inputting low quality images into an image quality improving engine in which the accuracy of image quality improving is poor and a label (hereinafter, referred to as a "fake label") indicating that the relevant image was not obtained by imaging by the target imaging apparatus.

While it is not the case that the authenticity evaluating engine that performed learning using such training data can evaluate whether or not an input image was definitely obtained by imaging by imaging apparatus, the authenticity evaluating engine can evaluate whether or not the image seems like an image obtained by imaging by an imaging apparatus. Utilizing this characteristic, by inputting a high quality image that the image quality improving unit 404 generated into the authenticity evaluating engine, the authenticity evaluating unit 1807 can evaluate whether or not a high quality image which the image quality improving unit 404 generated was subjected to sufficient image quality improving.

If it is determined by the authenticity evaluating unit 1807 that a high quality image which the image quality improving unit 404 generated was subjected to sufficient image quality improving, the outputting unit 405 causes the display unit 20 to display the high quality image. On the other hand, if it is determined by the authenticity evaluating unit 1807 that a high quality image which the image quality improving unit 404 generated was not subjected to sufficient image quality improving, the outputting unit 405 causes the display unit 20 to display the input image. Note that, when causing the input image to be displayed, the outputting unit 405 can cause the display unit 20 to display information indicating that a high quality image generated by the image quality improving unit 404 was not subjected to sufficient image quality improving or that the image being displayed is the input image.

Hereunder, a series of image processing operations according to the present embodiment is described referring to FIG. 19. FIG. 19 is a flowchart illustrating the series of image processing operations according to the present embodiment. Note that, the processing in step S1910 to step S1940 according to the present embodiment is the same as the processing in step S510 to step S540 in the first embodiment, and hence a description of the processing is omitted here. Note that, in a case where the image quality of an input image is to be improved unconditionally with regard to the imaging conditions, after performing the processing in step S1920, the processing in step S1930 can be omitted and the processing can shift to step S1940.

In step S1940, upon the image quality improving unit 404 generating a high quality image group, the processing shifts to step S1950. In step S1950, the authenticity evaluating unit 1807 inputs a high quality image generated in step S1940 into the authenticity evaluating engine, and performs an authenticity evaluation based on the output of the authenticity evaluating engine. Specifically, in a case where the real label (True) was output from the authenticity evaluating engine, the authenticity evaluating unit 1807 makes an evaluation that the generated high quality image was subjected to sufficient image quality improving. On the other hand, in a case where the fake label (False) was output from the authenticity evaluating engine, the authenticity evaluating unit 1807 makes an evaluation that the generated high quality image was not subjected to sufficient image quality improving.

In step S1960, if the authenticity evaluating unit 1807 determined that the high quality image which the image quality improving unit 404 generated was subjected to sufficient image quality improving, the outputting unit 405 causes the display unit 20 to display the relevant high quality image. On the other hand, if it is determined by the authenticity evaluating unit 1807 that the high quality image which the image quality improving unit 404 generated was not subjected to sufficient image quality improving, the outputting unit 405 causes the display unit 20 to display the input image.

As described above, the image processing apparatus 1800 according to the present embodiment further includes the authenticity evaluating unit 1807 that evaluates the image quality of a high quality image, and the authenticity evaluating unit 1807 includes an authenticity evaluating engine that evaluates the authenticity of an image. The authenticity evaluating engine includes a machine learning engine for which images generated by an image quality improving engine in which the accuracy of the image quality improving processing is lower (poorer) than in the image quality improving engine of the image quality improving unit 404 were used as training data. In a case where the output from the authenticity evaluating engine of the authenticity evaluating unit indicates that the relevant high quality image is authentic, the outputting unit 405 of the image processing apparatus 1800 outputs the high quality image.

By this means, according to the image processing apparatus 1800 of the present embodiment, the examiner can efficiently confirm that a high quality image was subjected to sufficient image quality improving.

Further, the efficiency and accuracy of both the image quality improving engine and the authenticity evaluating engine may be improved by coordinately training the machine learning model of the image quality improving engine and the machine learning model of the authenticity evaluating engine.

Note that, although in the present embodiment a configuration is adopted in which the image quality improving unit 404 generates a single high quality image, and the authenticity evaluating unit 1807 performs an evaluation regarding the generated single high quality image, an evaluation performed by the authenticity evaluating unit 1807 is not limited thereto. For example, in a case where the image quality improving unit 404 generates a plurality of high quality images using a plurality of image quality improving engines as in the second embodiment, the authenticity evaluating unit 1807 may be configured to perform an evaluation regarding at least one of the plurality of the generated high quality images. In this case, for example, the authenticity evaluating unit 1807 may perform an evaluation regarding all of the plurality of the generated high quality images, or may perform an evaluation regarding only an image instructed by the examiner among the plurality of high quality images.

In addition, the outputting unit 405 may cause the display unit 20 to display a result of determination by the authenticity evaluating unit 1807 as to whether or not a high quality image was subjected to sufficient image quality improving, and may output the high quality image in accordance with an instruction of the examiner.

Note that, similarly to the first embodiment, the outputting unit 405 may output a generated high quality image to the imaging apparatus 10 or to another apparatus connected to the image processing apparatus 1800. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Tenth Embodiment

Next, an image processing apparatus according to a tenth embodiment is described referring to FIG. 4 and FIG. 5. In the present embodiment, an image quality improving unit divides an input three-dimensional image into a plurality of two-dimensional images and inputs the plurality of two-dimensional images into an image quality improving engine, and then combines output images from the image quality improving engine to generate a three-dimensional high quality image.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, the components illustrated in FIG. 4 are denoted by the same reference numerals as in the first embodiment, and a description of the components is omitted hereunder.

The obtaining unit 401 according to the present embodiment obtains a three-dimensional image composed of a group of two-dimensional images which are structurally continuous. Specifically, the three-dimensional image is, for example, a three-dimensional OCT volume image composed of a group of OCT B-scan images (tomographic images). Further, the three-dimensional image is, for example, a three-dimensional CT volume image composed of a group of axial tomographic images.

Similarly to the first embodiment, the image quality improving unit 404 includes an image quality improving engine. Note that, a pair group of input data and ground truth as training data of the image quality improving engine is composed by an image group of two-dimensional images. The image quality improving unit 404 divides the obtained three-dimensional image into a plurality of two-dimensional images, and inputs each two-dimensional image into the image quality improving engine. By this means, the image quality improving unit 404 can generate a plurality of two-dimensional high quality images.

The outputting unit 405 combines the plurality of two-dimensional high quality images generated with respect to the respective two-dimensional images of the three-dimensional image by the image quality improving unit 404, to thereby output a three-dimensional high quality image.

Next, a series of image processing operations according to the present embodiment is described referring to FIG. 5. Note that, the processing in step S510 to step S530 and step S550 according to the present embodiment is similar to the processing in these steps in the first embodiment, and hence a description of the processing is omitted here. However, in step S510, the obtaining unit 401 obtains a three-dimensional image. Note that, in a case where the image quality of an input image is to be improved unconditionally with regard to the imaging conditions, after performing the processing in step S520, the processing in step S530 can be omitted and the processing can shift to step S540.

In step S530, if the image quality improvement possibility determining unit 403 determines that the input image can be handled by the image quality improving engine, the processing shifts to step S540. Note that, the image quality improvement possibility determining unit 403 may make the determination in question based on imaging conditions of the three-dimensional image, or may make the determination based on imaging conditions relating to a plurality of two-dimensional images constituting the three-dimensional image. In step S540, the image quality improving unit 404 divides the obtained three-dimensional image into a plurality of two-dimensional images. The image quality improving unit 404 inputs each of the divided plurality of two-dimensional images to the image quality improving engine, to thereby generate a plurality of two-dimensional high quality images. The image quality improving unit 404 combines the generated plurality of two-dimensional high quality images based on the obtained three-dimensional image, to thereby generate a three-dimensional high quality image.

In step S550, the outputting unit 405 causes the display unit 20 to display the generated three-dimensional high quality image. Note that, the three-dimensional high quality image may be displayed in any display form.

As described above, the image quality improving unit 404 according to the present embodiment divides an input three-dimensional image into a plurality of two-dimensional images, and inputs the plurality of two-dimensional images into the image quality improving engine. The image quality improving unit 404 combines a plurality of two-dimensional high quality images that were output from the image quality improving engine, to thereby generate a three-dimensional high quality image.

Thus, the image quality improving unit 404 according to the present embodiment can improve the image quality of a three-dimensional image by using an image quality improving engine which performed learning using training data composed of two-dimensional images.

Note that, similarly to the first embodiment, the outputting unit 405 may output a generated high quality image to the imaging apparatus 10 or to another apparatus connected to the image processing apparatus 400. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Eleventh Embodiment

Next, an image processing apparatus according to an eleventh embodiment is described referring to FIG. 4 and FIG. 5. In the present embodiment, an image quality improving unit divides an input three-dimensional image into a plurality of two-dimensional images, subjects the plurality of two-dimensional images to image quality improving in parallel by a plurality of image quality improving engines, and combines output images from the image quality improving engines to generate a three-dimensional high quality image.

Unless explicitly stated otherwise, the configuration and processing of the image processing apparatus according to the present embodiment are the same as the configuration and processing of the image processing apparatus 400 according to the tenth embodiment. Therefore, hereunder, the image processing apparatus according to the present embodiment is described centering on differences from the image processing apparatus according to the tenth embodiment. Note that, since the configuration of the image processing apparatus according to the present embodiment is similar to the configuration of the image processing apparatus according to the first and tenth embodiments, components illustrated in FIG. 4 are denoted by the same reference numerals as in the first and tenth embodiments, and a description of the components is omitted hereunder.

The image quality improving unit 404 according to the present embodiment includes a plurality of the same image quality improving engine as is provided in the tenth embodiment. Note that, a group of a plurality of image quality improving engines provided in the image quality improving unit 404 may be implemented in a manner that enables distributed processing in a group of two or more apparatuses through a circuit or a network, or may be implemented in a single apparatus.

Similarly to the tenth embodiment, the image quality improving unit 404 divides an obtained three-dimensional image into a plurality of two-dimensional images. The image quality improving unit 404 performs image quality improving on the plurality of two-dimensional images using the plurality of image quality improving engines by sharing the processing therebetween (parallelly), to thereby generate a plurality of two-dimensional high quality images. Based on the three-dimensional image that is the processing object, the image quality improving unit 404 combines the plurality of two-dimensional high quality images output from the plurality of image quality improving engines, to thereby generate a three-dimensional high quality image.

Next, a series of image processing operations according to the present embodiment is described referring to FIG. 5. Note that, the processing in step S510 to step S530 and step S550 according to the present embodiment is the same as the processing in these steps in the tenth embodiment, and hence a description of the processing is omitted here. Note that, in a case where the image quality of an input image is to be improved unconditionally with regard to the imaging conditions, after performing the processing in step S520, the processing in step S530 can be omitted and the processing can shift to step S540.

In step S530, if the image quality improvement possibility determining unit 403 determines that the input image can be handled by the image quality improving engine, the processing shifts to step S540. Note that, the image quality improvement possibility determining unit 403 may make the determination in question based on imaging conditions of the three-dimensional image, or may make the determination based on imaging conditions relating to a plurality of two-dimensional images constituting the three-dimensional image.

In step S540, the image quality improving unit 404 divides the obtained three-dimensional image into a plurality of two-dimensional images. The image quality improving unit 404 inputs each of the divided plurality of two-dimensional images to the plurality of image quality improving engines to perform image quality improving processing of the two-dimensional images in parallel and generate a plurality of two-dimensional high quality images. The image quality improving unit 404 combines the generated plurality of two-dimensional high quality images based on the obtained three-dimensional image, to thereby generate a three-dimensional high quality image.

In step S550, the outputting unit 405 causes the display unit 20 to display the generated three-dimensional high quality image. Note that, the three-dimensional high quality image may be displayed in any display form.

As described above, the image quality improving unit 404 according to the present embodiment includes a plurality of image quality improving engines. The image quality improving unit 404 divides a input three-dimensional image into a plurality of two-dimensional images, and generates a plurality of two-dimensional high quality images by using the plurality of image quality improving engines in parallel. The image quality improving unit 404 integrates the plurality of two-dimensional high quality images to generate a three-dimensional high quality image.

Thus, the image quality improving unit 404 according to the present embodiment can improve the image quality of a three-dimensional image by using image quality improving engines which performed learning using training data composed of two-dimensional images. Further, the image quality of a three-dimensional image can be improved more efficiently in comparison to the tenth embodiment.

Note that, the training data of the plurality of image quality improving engines may be training data that differs according to a processing object with respect to which processing is performed by the respective image quality improving engines. For example, a first image quality improving engine may perform learning using training data for a first imaged region, and a second image quality improving engine may perform learning using training data for a second imaged region. In this case, the respective image quality improving engines can perform image quality improving with respect to a two-dimensional image more accurately.

Further, similarly to the first embodiment, the outputting unit 405 may output a generated high quality image to the imaging apparatus 10 or to another apparatus connected to the image processing apparatus 400. Further, similarly to the first embodiment, the ground truth of training data for an image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Twelfth Embodiment

Figure 20:
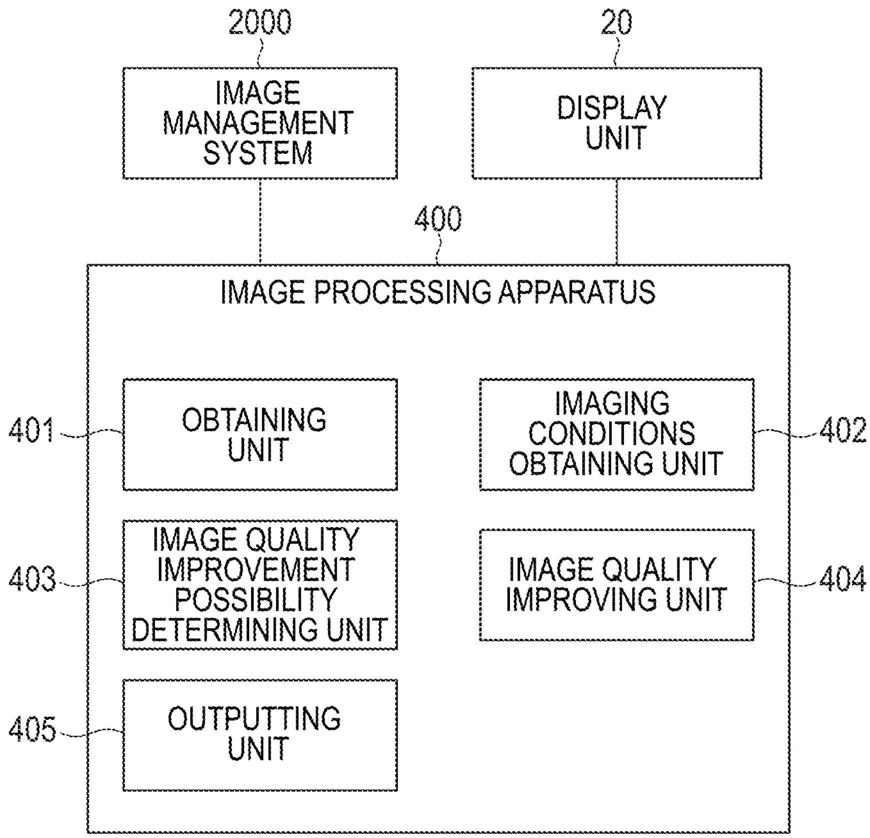
FIG. 20 is a view illustrating an example of a schematic configuration of an image processing apparatus according to a twelfth embodiment.

Next, an image processing apparatus according to a twelfth embodiment is described referring to FIG. 5 and FIG. 20. In the present embodiment, the obtaining unit 401 obtains an input image from an image management system 2000, and not an imaging apparatus.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus 400 according to the first embodiment, components illustrated in FIG. 4 are denoted by the same reference numerals as in the first embodiment, and a description of the components is omitted hereunder.

FIG. 20 is a view illustrating a schematic configuration of the image processing apparatus 400 according to the present embodiment. The image processing apparatus 400 according to the present embodiment is connected to the image management system 2000 and the display unit 20 through any circuit or network. The image management system 2000 is an apparatus and system configured to receive and store images imaged by any imaging apparatus or images subjected to image processing. Further, the image management system 2000 can transmit an image in response to a request from a connected apparatus, perform image processing on a stored image, and request another apparatus to carry out a request for image processing. A picture archiving and communication system (PACS) can be included as an example of the image management system.

The obtaining unit 401 according to the present embodiment can obtain an input image from the image management system 2000 connected to the image processing apparatus 400. Further, the outputting unit 405 can output a high quality image generated by the image quality improving unit 404 to the image management system 2000.

Next, a series of image processing operations according to the present embodiment is described referring to FIG. 5. Note that, the processing in step S520 to step S540 according to the present embodiment is the same as the processing in these steps in the first embodiment, and hence a description of the processing is omitted here. Note that, in a case where the image quality of an input image is to be improved unconditionally with regard to the imaging conditions, after performing the processing in step S520, the processing in step S530 can be omitted and the processing can shift to step S540.

In step S510, an image stored in the image management system 2000 is obtained as an input image by the obtaining unit 401 from the image management system 2000 that is connected to the image processing apparatus 400 through a circuit or network. Note that, the obtaining unit 401 may obtain the input image in response to a request from the image management system 2000. Such a request may be issued, for example, when the image management system 2000 stores an image, or before transmitting a stored image to another apparatus, or when displaying a stored image on the display unit 20. Further, the relevant request may be issued, for example, when a user operates the image management system 2000 to make a request for image quality improving processing, or when an image analysis function that the image management system 2000 includes utilizes a high quality image.

The processing from step S520 to step S540 is the same as the processing in the first embodiment. Upon the image quality improving unit 404 generating a high quality image in step S540, the processing shifts to step S550. In step S550, if a high quality image was generated in step S540, the outputting unit 405 outputs the high quality image as an output image to the image management system 2000. If a high quality image was not generated in step S540, the outputting unit 405 outputs the aforementioned input image to the image management system 2000 as an output image. Note that, depending on the settings or implementation of the image processing apparatus 400, the outputting unit 405 may process the output image or convert the data format of the output image so that the image management system 2000 can utilize the output image.

As described above, the obtaining unit 401 according to the present embodiment obtains an input image from the image management system 2000. Therefore, based on an image that the image management system 2000 stores, the image processing apparatus 400 of the present embodiment can output a high quality image that is suitable for image diagnosis without increasing the invasiveness with respect to the subject or the labor of the person performing the imaging. Further, an output high quality image can be stored in the image management system 2000, or can be displayed on a user interface which the image management system 2000 includes. Further, an output high quality image can be utilized by an image analysis function that the image management system 2000 includes, or can be transmitted through the image management system 2000 to another apparatus connected to the image management system 2000.

Note that, the image processing apparatus 400, the image management system 2000 and the display unit 20 may be connected through a circuit or network to other apparatuses (not illustrated). Further, although in the present embodiment these apparatuses are assumed to be separate apparatuses to each other, some or all of these apparatuses may be constituted integrally with each other.

Further, similarly to the first embodiment, the outputting unit 405 may output a generated high quality image to the image management system 2000 or another apparatus connected to the image processing apparatus 400.

Thirteenth Embodiment

Next, an image processing apparatus according to a thirteenth embodiment is described referring to FIG. 4, FIG. 5, FIG. 21A and FIG. 21B. In the present embodiment, an image quality improving unit adopts a plurality of images as input images to generate a single high quality image.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The obtaining unit 401 according to the present embodiment obtains a plurality of images as input data that is the processing object from the imaging apparatus 10 or another apparatus.

An image quality improving engine that is the same as in the first embodiment is provided in the image quality improving unit 404 according to the present embodiment. The training data may also be the same as in the first embodiment. The image quality improving unit 404 inputs each of the plurality of images obtained by the obtaining unit 401 to the image quality improving engine, and performs averaging processing on an output plurality of high quality images, to thereby generate a final high quality image. Note that, before performing averaging processing of the plurality of high quality images, the image quality improving unit 404 may align the plurality of high quality images by any method.

The outputting unit 405 causes the display unit 20 to display the final high quality image that the image quality improving unit 404 generated. Note that, the outputting unit 405 may cause the plurality of input images to be displayed on the display unit 20 together with the final high quality image. Further, the outputting unit 405 may display the generated plurality of high quality images on the display unit 20 together with the final high quality image or the input images.

Figure 21A:
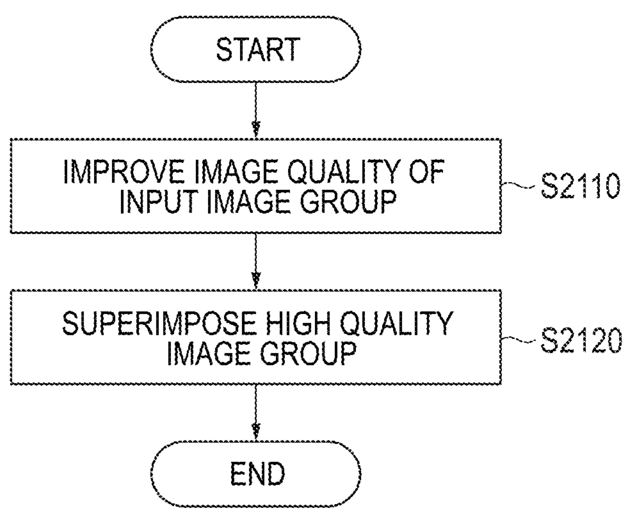
FIG. 21A is a flowchart illustrating an example of a flow of image quality improving processing according to a thirteenth embodiment.
Figure 21B:
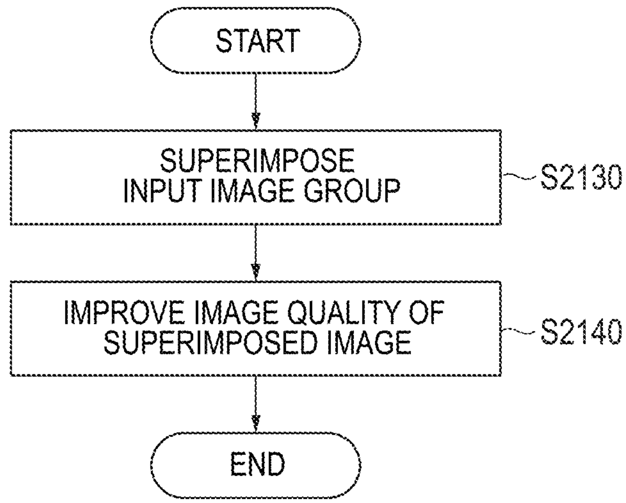
FIG. 21B is a flowchart illustrating a different example of the flow of image quality improving processing according to the thirteenth embodiment.

Next, a series of image processing operations according to the present embodiment is described referring to FIG. 5 and FIG. 21A. FIG. 21A is a flowchart of image quality improving processing according to the present embodiment. Note that, the processing in step S510 to step S530 according to the present embodiment is similar to the processing in these steps in the first embodiment, and hence a description of the processing is omitted here.

However, in step S510, the obtaining unit 401 obtains a plurality of images, and in step S520 and S530, the imaging conditions are obtained for each of the plurality of images and it is determined whether or not the respective images can be handled by the image quality improving engine. Note that, in a case where the image quality of each input image is to be improved unconditionally with regard to the imaging conditions, after performing the processing in step S520, the processing in step S530 can be omitted and the processing can shift to step S540. Further, in a case where it is determined that one or more images among the plurality of images cannot be handled by the image quality improving engine, the relevant image can be excluded from the subsequent processing.

If the image quality improvement possibility determining unit 403 determines in step S530 that the plurality of input images can be handled by the image quality improving engine, the processing shifts to step S540. When the processing shifts to step S540, image quality improving processing according to the present embodiment illustrated in FIG. 21A is started. In the image quality improving processing according to the present embodiment, first, in step S2110 the image quality improving unit 404 inputs each of the plurality of input images to the image quality improving engine to generate a high quality image group.

Next, in step S2120, the image quality improving unit 404 subjects the generated group of high quality images to averaging processing to generate a final single high quality image. Note that, the averaging processing may be performed by the image quality improving processing such as the averaging processing or by any other existing processing. When performing the averaging, the image quality improving unit 404 may align the plurality of high quality images by any method and thereafter perform the averaging. Upon the image quality improving unit 404 generating the final high quality image, the processing shifts to step S550.

In step S550, the outputting unit 405 displays the generated final high quality image on the display unit 20.

As described above, the image quality improving unit 404 according to the present embodiment generates a single final high quality image from a plurality of input images. Because image quality improving performed by the image quality improving engine is based on the input images, for example, in a case where a lesion portion or the like is not suitably displayed in a certain input image, the lesion portion or the like will be a portion with low pixel values in a high quality image generated by subjecting the relevant input image to image quality improving. On the other hand, in some cases the lesion portion or the like is suitably displayed in another input image imaged at the same location, and the lesion portion or the like will be a portion with high pixel values in a high quality image generated by subjecting the relevant other input image to image quality improving. Therefore, by averaging these high quality images, the relevant location with low or high pixel values can be suitably displayed, and a high quality image with high contrast can be generated. Note that, by setting the number of input images to a smaller number than the number of images necessary for conventional averaging, a cost such as prolonging the imaging time that occurs in the conventional technique can be lessened.

Note that, the aforementioned effect is noticeable, for example, in the case of using input images for which motion contrast data such as OCTA data is used.

Because motion contrast data is obtained by detecting temporal changes at an imaging target during a time interval in which the same location of the imaging target was repeatedly imaged, for example, there are cases where only slight motion can be detected with respect to the motion of the imaging target during a certain time interval. On the other hand, there are also cases where, when imaging is performed during a different time interval, motion of the imaging target can be detected as a large motion. Therefore, by averaging images generated by subjecting the motion contrast images obtained in each of these cases to image quality improving, motion contrast which did not occur at a specific timing or which was only slightly detected can be interpolated. Therefore, according to such processing, a motion contrast image for which contrast enhancement was performed with respect to a greater amount of motion of the imaging target can be generated, and the examiner can ascertain a more exact state of the imaging target.

Accordingly, in a case where images which visualize locations that change over time such as OCTA images are used as input images, a predetermined site of the subject can be imaged in greater detail by averaging high quality images obtained at different times.

Note that, although in the present embodiment high quality images are generated from a plurality of input images, respectively, and the high quality images are averaged to generate a final single high quality image, a method for generating a single high quality image from a plurality of input images is not limited to this method. For example, in a different example of the image quality improving processing of the present embodiment illustrated in FIG. 21B, upon the image quality improving processing being started in step S540, in step S2130 the image quality improving unit 404 averages the group of input images to generate a single averaged input image.

Thereafter, in step S2140, the image quality improving unit 404 inputs the single averaged input image to the image quality improving engine to generate a single high quality image. Even when image quality improving processing is performed in this manner, similarly to the aforementioned image quality improving processing, locations with low or high pixel values with respect to the plurality of input images can be appropriately displayed, and a high-contrast high quality image can be generated. This processing can also achieve a noticeable effect in a case where the aforementioned motion contrast images such as the OCTA images are used as input images.

Note that, in the case of perform the high image quality processing in question, an averaged image of the same number of input images as the plurality of input images assumed as the processing object is used as the input data of the training data of the image quality improving engine. Thus, appropriate image quality improving processing can be performed by the image quality improving engine.

Further, with regard to the image quality improving processing according to the present embodiment and the aforementioned different image quality improving processing, processing for combining a high quality image group or an input image is not limited to averaging processing. For example, a single image may be generated by applying MAP estimation processing to each of these image groups. Further, a single image may be generated by combining the high quality image group or the input image group.

Examples of a case where a single image is generated by combining a high quality image group or an input image group include a case where an image having a wide gradation with respect to a high intensity region and an image having a wide gradation with respect to a low intensity region are used as input images. In this case, for example, an image generated by subjecting an image having a wide gradation with respect to a high intensity region to image quality improving, and an image generated by subjecting an image having a wide gradation with respect to a low intensity region to image quality improving are combined. By this means, an image that can express a wider brightness range (dynamic range) can be generated. Note that, in this case, an image having a wide gradation with respect to a high intensity region and a low quality image having a wide gradation with respect to a low intensity region that are assumed as processing objects can be adopted as input data of the training data of the image quality improving engine. Further, high quality images corresponding to the input data can be adopted as ground truth of the training data of the image quality improving engine.

Further, an image having a wide gradation with respect to a high intensity region and an image having a wide gradation with respect to a low intensity region may be combined, and the combined image may be subjected to image quality improving by the image quality improving engine. In this case also, an image that can express a wider brightness range can be generated. Note that, in this case, an image generated by combining a low quality image having a wide gradation with respect to a high intensity region and a low quality image having a wide gradation with respect to a low intensity region which is assumed as a processing object can be adopted as input data of the training data of the image quality improving engine. Further, a high quality image corresponding to the input data can be adopted as the ground truth of the training data of the image quality improving engine.

In these cases, an image that can express a wider brightness range can be subjected to image quality improving using an image quality improving engine, and processing with a smaller number of images than in the conventional technique can be performed, and an image that is suitable for image analysis can be provided with less of a cost.

Note that, any method such as a method that shortens or lengthens the exposure time of the imaging apparatus may be employed as a method for imaging an image having a wide gradation with respect to a high intensity region and an image having a wide gradation with respect to a low intensity region. Further, the manner in which the gradation width is divided is not limited to a low intensity region and a high intensity region, and the gradation width may be divided in any manner.

Further, in the image quality improving processing according to the present embodiment, a plurality of input images may be processed in parallel using a plurality of image quality improving engines. Note that, similarly to the first embodiment, the outputting unit 405 may output a generated high quality image to the imaging apparatus 10 or to another apparatus connected to the image processing apparatus 400. Further, similarly to the first embodiment, the ground truth of training data for the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Fourteenth Embodiment

Next, an image processing apparatus according to a fourteenth embodiment is described referring to FIG. 4 and FIG. 5. In the present embodiment, an image quality improving unit adopts a medium quality image generated from a plurality of low quality images as an input image, and generates a high quality image.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, the components illustrated in FIG. 4 are denoted by the same reference numerals as in the first embodiment, and a description of the components is omitted hereunder.

The obtaining unit 401 according to the present embodiment obtains a medium quality image generated by subjecting a plurality of low quality images to averaging processing, as input data that is the processing object, from the imaging apparatus 10 or another apparatus. Note that, when averaging the low quality images, any alignment processing may be performed.

The image quality improving unit 404 according to the present embodiment includes a similar image quality improving engine to the first embodiment. However, the image quality improving engine of the present embodiment is designed to output a high quality image when a medium quality image which is an image with a medium level of image quality is input thereto. The medium quality image is an averaged image generated by averaging a plurality of low quality image groups. Further, the high quality image is an image with higher image quality than the medium quality image. In addition, with regard to a pair group constituting training data used for training by the image quality improving engine, the input data constituting each pair is a medium quality image generated in a similar manner to the aforementioned medium quality image, and the ground truth is a high quality image.

The outputting unit 405 causes the display unit 20 to display a high quality image which the image quality improving unit 404 generated. Note that, the outputting unit 405 may cause the display unit 20 to display an input image together with the high quality image, and in such a case the outputting unit 405 may cause the display unit 20 to display information indicating that the input image is an image generated from a plurality of low quality images.

Next, a series of image processing operations according to the present embodiment is described referring to FIG. 5. Note that, the processing in step S520 to step S550 according to the present embodiment is the same as the processing in these steps in the first embodiment, and hence a description of the processing is omitted here.

In step S510, the obtaining unit 401 obtains a medium quality image as an input image from the imaging apparatus 10 or another apparatus. Note that, as an input image, the obtaining unit 401 may obtain a medium quality image that the imaging apparatus 10 generated, in response to a request from the imaging apparatus 10. Such a request may be issued, for example, when the imaging apparatus 10 generated an image, or when displaying an image which the imaging apparatus 10 generated on the display unit 20 before storing the image in a storage apparatus which the imaging apparatus 10 includes or displaying the stored image on the display unit 20 after storing the image in the storage apparatus, or when utilizing a high quality image for image analysis processing.

The processing thereafter is the same as the processing in the first embodiment, and hence a description of the processing is omitted here.

As described above, the obtaining unit 401 according to the present embodiment obtains a medium quality image that is an image generated using a plurality of images of a predetermined site of a subject as an input image. In this case, because the input image is a clearer image, the image quality improving engine can generate a high quality image with greater accuracy. Note that, the number of low quality images used for generating a medium quality image may be less than the number of images used for generating a conventional averaged image.

Note that, the medium quality image is not limited to an image generated by averaging a plurality of low quality images, and for example may be an image generated by applying MAP estimation processing to a plurality of low quality images, or an image generated by combining a plurality of low quality images. In the case of combining a plurality of low quality images, images in which the gradations of the respective images are different to each other may be combined.

Further, similarly to the first embodiment, the outputting unit 405 may output a generated high quality image to the imaging apparatus 10 or to another apparatus connected to the image processing apparatus 400. Further, similarly to the first embodiment, the ground truth of training data for an image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Fifteenth Embodiment

Next, an image processing apparatus according to a fifteenth embodiment is described referring to FIG. 4 and FIG. 5. In the present embodiment, an image quality improving unit performs image size increasing (size increasing) with respect to an input image together with the processing for image quality improving according to the first embodiment and the like.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The obtaining unit 401 according to the present embodiment obtains an image with a small size (small size image) as an input image. Note that, the term "small size image" refers to an image in which the number of pixels constituting the image is less than in an image with a large size (large size image) output by an image quality improving engine to be described later. Specifically, for example, in a case where the size of the large size image is a width of 1024 pixels, a height of 1024 pixels and a depth of 1024 pixels, the size of the small size image is a width of 512 pixels, a height of 512 pixels and a depth of 512 pixels or the like. In this regard, in the present description the term "image size increasing" refers to processing that increases the number of pixels per image to enlarge the image size.

The image quality improving unit 404 according to the present embodiment includes an image quality improving engine, similarly to the first embodiment. However, the image quality improving engine of the present embodiment is configured to perform image size increasing with respect to the image size of an input image, together with reducing the noise and enhancing the contrast of the input image. Therefore, the image quality improving engine of the present embodiment is configured to accept input of a small size image and output a large size image.

In this connection, with regard to a pair group constituting training data used by the image quality improving engine, the input data constituting each pair is a small size image, and the ground truth is a large size image. Note that, the large size image used for the ground truth can be obtained from an apparatus with higher performance than the imaging apparatus which obtained the small size image, or by changing the settings of the imaging apparatus. Further, in a case where there is already a group of large size images, the size of each image in the group of large size images can be reduced to the image size of an image assumed to be obtained from the imaging apparatus 10, to thereby obtain a group of small size images to be used as input data. In addition, with respect to the large size image, an image may be used that is obtained by averaging small size images in a similar manner to the first embodiment and the like.

Note that, with regard to enlargement of the image size of an input image by the image quality improving unit 404 according to the present embodiment, since, as training data, an image is obtained from an apparatus with higher performance than the imaging apparatus 10 or is obtained by changing the settings of the imaging apparatus 10, the enlargement in this case is different from simple enlargement of an image. Specifically, processing for enlarging the image size of an input image by the image quality improving unit 404 according to the present embodiment can reduce degradation of the resolution compared to a case where the image is simply enlarged.

According to this configuration, the image quality improving unit 404 according to the present embodiment can generate a high quality image generated by reducing the noise and enhancing the contrast of an input image and also increasing the image size.

Next, a series of image processing operations according to the present embodiment is described referring to FIG. 5. Note that, the processing in step S520, step S530 and step S550 according to the present embodiment is the same as the processing in these steps in the first embodiment, and hence a description of the processing is omitted here. Note that, in a case where the image quality of an input image is to be improved unconditionally with regard to the imaging conditions, after performing the processing in step S520, the processing in step S530 can be omitted and the processing can shift to step S540.

In step S510, the obtaining unit 401 obtains a small size image as input data that is the processing object from the imaging apparatus 10 or another apparatus. Note that, as an input image, the obtaining unit 401 may obtain a small size image that the imaging apparatus 10 generated, in response to a request from the imaging apparatus 10. Such a request may be issued, for example, when the imaging apparatus 10 generated an image, or when displaying an image which the imaging apparatus 10 generated on the display unit 20 before storing the image in a storage apparatus which the imaging apparatus 10 includes or displaying the stored image on the display unit 20 after storing the image in the storage apparatus, or when utilizing a high quality image for image analysis processing.

Since the processing in step S520 and step S530 is the same as the processing in the first embodiment, a description of the processing is omitted here. In step S540, the image quality improving unit 404 inputs the input image to the image quality improving engine to thereby generate, as a high quality image, an image subjected to image size increasing as well as noise reduction and contrast enhancement. The processing thereafter is the same as in the first embodiment, and hence a description of the processing is omitted here.

As described above, the image quality improving unit 404 according to the present embodiment generates a high quality image for which, in comparison to the input image, enlargement of the image size was performed and which underwent at least one of noise reduction and contrast enhancement. By this means, the image processing apparatus 400 according to the present embodiment can output a high quality image that is suitable for image diagnosis without increasing the invasiveness with respect to the subject or the labor of the person performing the imaging.

Note that, although in the present embodiment a high quality image is generated on which image quality improving processing according to the first embodiment or the like and processing for increasing the image size were performed by a single image quality improving engine, a configuration for performing such processing is not limited to this configuration. For example, the image quality improving unit may include an image quality improving engine that performs image quality improving processing according to the first embodiment or the like and a separate image quality improving engine that performs image size increasing processing.

In this case, the image quality improving engine that performs image quality improving processing according to the first embodiment or the like can use a machine learning model that performed learning similarly to the image quality improving engine according to the first embodiment or the like. Further, a high quality image generated by the image quality improving engine according to the first embodiment or the like is used as the input data of the training data for the image quality improving engine that performs image size increasing processing. In addition, a high quality image generated by the image quality improving engine according to the first embodiment or the like with respect to an image obtained by a high-performance imaging apparatus is used as the ground truth of the training data for the relevant image quality improving engine. By this means, the image quality improving engine that performs image size increasing processing can generate a final high quality image that is an image generated by increasing the image size of a high quality image generated by performing image quality improving processing according to the first embodiment or the like.

Further, the image size increasing processing by the relevant image quality improving engine may be performed before the image quality improving processing by the image quality improving engine according to the first embodiment or the like. In this case, training data for the image quality improving engine that performs the image size increasing processing is constituted by a pair group composed of input data that is a small size image and ground truth that is a large size image obtained by an imaging apparatus. Further, the training data for the image quality improving engine that performs the image quality improving processing according to the first embodiment or the like is constituted by a pair group composed of input data that is a large size image and ground truth that is an image generated by averaging large size images.

By this configuration also, as a high quality image, the image processing apparatus 400 can generate an image for which, in comparison to the input image, enlargement of the image size was performed and at least one of noise reduction and contrast enhancement was performed.

Note that, although in the present embodiment a configuration is described in which, with regard to the image quality improving processing according to the first embodiment or the like, an averaged image is used as ground truth of the training data, the ground truth is not limited thereto, similarly to the first embodiment. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Note that, similarly to the first embodiment, the outputting unit 405 may output a generated high quality image to the imaging apparatus 10 or to another apparatus connected to the image processing apparatus 400.

Sixteenth Embodiment

Next, an image processing apparatus according to a sixteenth embodiment is described referring to FIG. 4 and FIG. 5. In the present embodiment, an image quality improving unit performs spatial resolution increasing as well as the image quality improving according to the first embodiment or the like.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The obtaining unit 401 according to the present embodiment obtains a low spatial resolution image as an input image. Note that, the term "low spatial resolution image" refers to an image in which the spatial resolution is lower than the spatial resolution of a high spatial resolution image which the image quality improving unit 404 outputs.

The image quality improving unit 404 includes an image quality improving engine, similarly to the first embodiment. However, the image quality improving engine of the present embodiment is configured to perform spatial resolution increasing with respect to the spatial resolution of an input image, together with reducing the noise and enhancing the contrast of the input image. Therefore, the image quality improving engine of the present embodiment is configured to accept input of a low spatial resolution image and output a high spatial resolution image.

In this connection, with regard to a pair group constituting training data used by the image quality improving engine also, the input data constituting each pair is a low spatial resolution image, and the ground truth is a high spatial resolution image. Note that, the high spatial resolution image can be obtained from an apparatus with higher performance than the imaging apparatus which obtained the low spatial resolution image, or by changing the settings of the imaging apparatus. Further, with respect to the high spatial resolution image, an image may be used obtained by averaging low spatial resolution images in a similar manner to the first embodiment and the like.

According to this configuration, the image quality improving unit 404 according to the present embodiment can generate a high quality image generated by reducing the noise and enhancing the contrast of an input image and also increasing the spatial resolution.

Next, a series of image processing operations according to the present embodiment is described referring to FIG. 5. Note that, the processing in step S520, step S530 and step S550 according to the present embodiment is the same as the processing in these steps in the first embodiment, and hence a description of the processing is omitted here. Note that, in a case where the image quality of an input image is to be improved unconditionally with regard to the imaging conditions, after performing the processing in step S520, the processing in step S530 can be omitted and the processing can shift to step S540.

In step S510, the obtaining unit 401 obtains a low spatial resolution image as input data that is the processing object from the imaging apparatus 10 or another apparatus. Note that, the obtaining unit 401 may obtain a low spatial resolution image that the imaging apparatus 10 generated, as an input image in response to a request from the imaging apparatus 10. Such a request may be issued, for example, when the imaging apparatus 10 generated an image, or when displaying an image which the imaging apparatus 10 generated on the display unit 20 before storing the image in a storage apparatus which the imaging apparatus 10 includes or displaying the stored image on the display unit 20 after storing the image in the storage apparatus, or when utilizing a high quality image for image analysis processing.

Since the processing in step S520 and step S530 is the same as the processing in the first embodiment, a description of the processing is omitted here. In step S540, the image quality improving unit 404 inputs the input image to the image quality improving engine to thereby generate, as a high quality image, an image subjected to spatial resolution increasing as well as noise reduction and contrast enhancement. The processing thereafter is the same as in the first embodiment, and hence a description of the processing is omitted here.

As described above, the image quality improving unit 404 according to the present embodiment generates, as a high quality image, an image for which, in comparison to the input image, the spatial resolution was increased and which underwent at least one of noise reduction and contrast enhancement. By this means, the image processing apparatus 400 according to the present embodiment can output a high quality image that is suitable for image diagnosis without increasing the invasiveness with respect to the subject or the labor of the person performing the imaging.

Note that, although in the present embodiment a high quality image is generated on which image quality improving processing according to the first embodiment or the like and processing for increasing the spatial resolution was performed by a single image quality improving engine, a configuration for performing such processing is not limited to the foregoing configuration. For example, the image quality improving unit may include an image quality improving engine that performs image quality improving processing according to the first embodiment or the like and a separate image quality improving engine that performs spatial resolution increasing processing.

In this case, the image quality improving engine that performs image quality improving processing according to the first embodiment or the like can use a machine learning model that performed learning similarly to the image quality improving engine according to the first embodiment or the like. Further, a high quality image generated by the image quality improving engine according to the first embodiment or the like is used as the input data of the training data for the image quality improving engine that performs spatial resolution increasing processing. In addition, a high quality image generated by the image quality improving engine according to the first embodiment or the like with respect to an image obtained by a high-performance imaging apparatus is used as the ground truth of the training data for the relevant image quality improving engine. By this means, the image quality improving engine that performs spatial resolution increasing processing can generate a final high quality image that is an image generated by increasing the spatial resolution of a high quality image generated by performing image quality improving processing according to the first embodiment or the like.

Further, the spatial resolution increasing processing by the relevant image quality improving engine may be performed before the image quality improving processing by the image quality improving engine according to the first embodiment or the like. In this case, training data for the image quality improving engine that performs the spatial resolution increasing processing is constituted by a pair group composed of input data that is a low spatial resolution image and ground truth that is a high spatial resolution image obtained by an imaging apparatus. Further, the training data for the image quality improving engine that performs the image quality improving processing according to the first embodiment or the like is constituted by a pair group composed of input data that is a high spatial resolution image and ground truth that is an image generated by averaging high spatial resolution images.

By this configuration also, as a high quality image, the image processing apparatus 400 can generate an image for which, in comparison to the input image, the spatial resolution was increased and at least one of noise reduction and contrast enhancement was performed.

Note that, although in the present embodiment a configuration is described in which, with regard to the image quality improving processing according to the first embodiment or the like, an averaged image is used as ground truth of the training data, the ground truth is not limited thereto, similarly to the first embodiment. In other words, a high quality image may be used that was obtained by performing at least one imaging method or processing among the imaging method and processing group including averaging processing, MAP estimation processing, smoothing filter processing, gradation conversion processing, imaging using a high-performance imaging apparatus, high-cost processing, and noise reduction processing.

Further, the image quality improving unit 404 may perform the image quality improving processing according to the fifteenth embodiment in addition to the spatial resolution increasing processing, using an image quality improving engine. In this case, an image that, compared to the input image, was subjected to image size increasing and spatial resolution increasing and which also underwent at least one of noise reduction and contrast enhancement compared to the input image can be generated as a high quality image. By this means, the image processing apparatus 400 according to the present embodiment can output a high quality image that is suitable for image diagnosis without increasing the invasiveness with respect to the subject or the labor of the person performing the imaging.

Note that, similarly to the first embodiment, the outputting unit 405 may output a generated high quality image to the imaging apparatus 10 or to another apparatus connected to the image processing apparatus 400.

Seventeenth Embodiment

Figure 22:
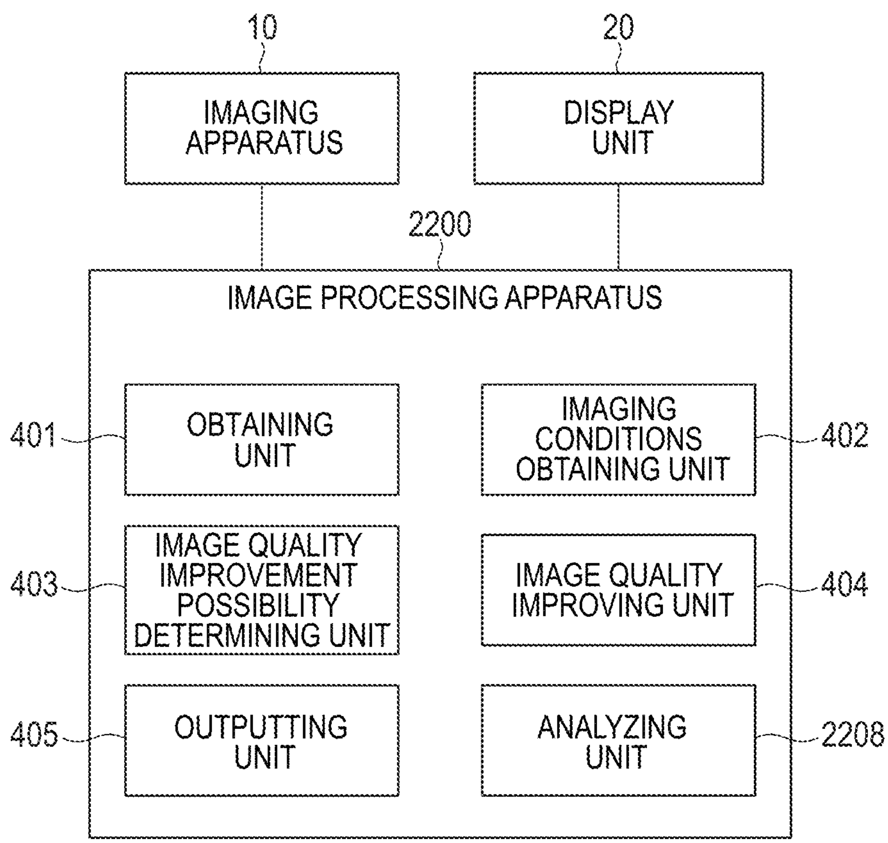
FIG. 22 is a view illustrating an example of a schematic configuration of an image processing apparatus according to a seventeenth embodiment.
Figure 23:
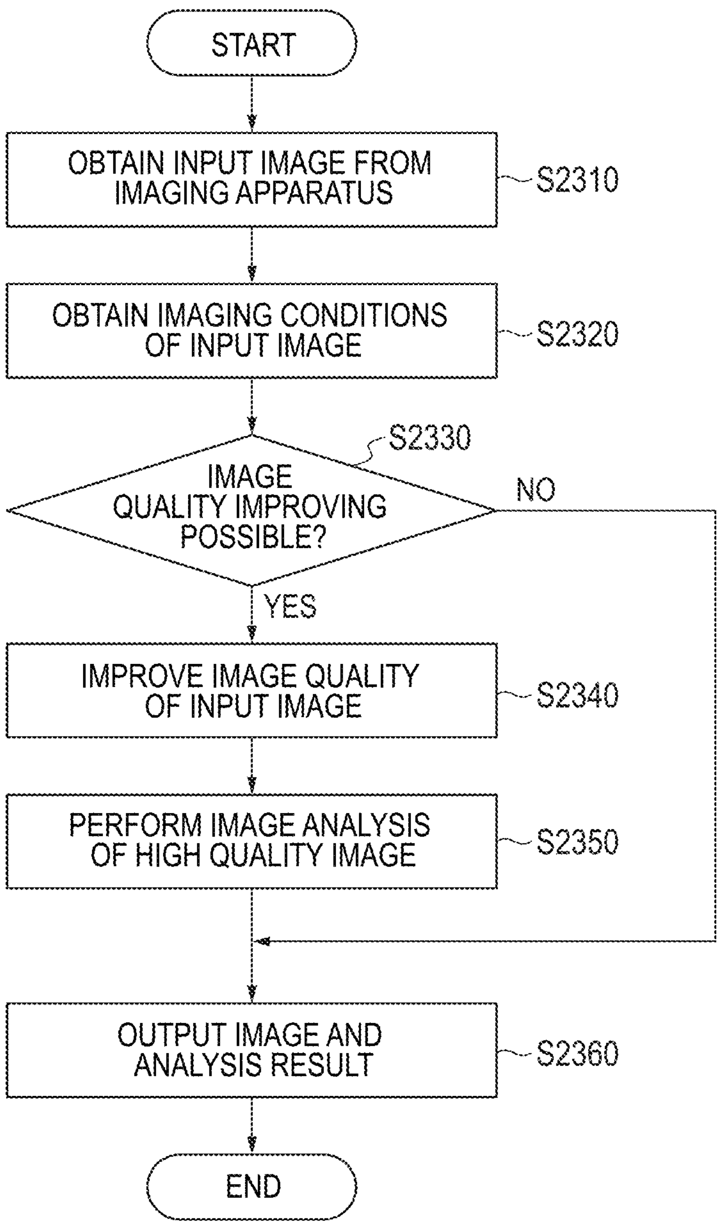
FIG. 23 is a flowchart illustrating an example of a flow of image processing according to the seventeenth embodiment.

Next, an image processing apparatus according to a seventeenth embodiment is described referring to FIG. 22 and FIG. 23. In the present embodiment, an analyzing unit performs image analysis of a high quality image generated by an image quality improving unit.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment.

FIG. 22 is a view illustrating a schematic configuration of an image processing apparatus 2200 according to the present embodiment. The image processing apparatus 2200 according to the present embodiment is provided with an analyzing unit 2208 in addition to the obtaining unit 401, the imaging conditions obtaining unit 402, the image quality improvement possibility determining unit 403, the image quality improving unit 404 and the outputting unit 405. Note that, the image processing apparatus 2200 may be constituted by a plurality of apparatuses which are each provided with one or more of these components. Here, since the configuration with respect to the obtaining unit 401, the imaging conditions obtaining unit 402, the image quality improvement possibility determining unit 403, the image quality improving unit 404 and the outputting unit 405 is the same as the configuration of the image processing apparatus according to the first embodiment, components illustrated in FIG. 4 are denoted by the same reference numerals as in the first embodiment, and a description of the components is omitted hereunder.

The analyzing unit 2208 subjects a high quality image that the image quality improving unit 404 generated to predetermined image analysis processing. For example, in the field of ophthalmology, examples of the image analysis processing include, for an image obtained by OCT, any existing image analysis processing such as segmentation of retinal layers, layer thickness measurement, three-dimensional shape analysis of the papilla, lamina cribrosa analysis, blood vessel density measurement of an OCTA image, and corneal shape analysis. Further, the image analysis processing is not limited to analytical processing in the field of ophthalmology, and for example, also includes any existing analytical processing in the field of radiation such as diffusion tensor analysis or VBL (voxel-based morphometry) analysis.

The outputting unit 405 can cause an analysis result obtained by image analysis processing by the analyzing unit 2208 to be displayed on the display unit 20 together with the display of a high quality image generated by the image quality improving unit 404. Note that, the outputting unit 405 may cause the display unit 20 to display only an image analysis result obtained by the analyzing unit 2208, or may output the image analysis result to the imaging apparatus 10 or the image management system or to another apparatus or the like. Note that, the form in which an analysis result is displayed may be any form that is in accordance with the image analysis processing performed by the analyzing unit 2208, and for example an analysis result may be displayed as an image, a numerical value or a character. Further, the form in which an analysis result is displayed may be a form in which an analysis result obtained by subjecting a high quality image to analytical processing is displayed in a superimposed manner on the high quality image with any degree of transparency. In other words, an analysis result may be displayed in the form of an image (for example, a two-dimensional map) obtained by subjecting a high quality image and an analysis result obtained by performing analytical processing of the high quality image to blending processing with any degree of transparency.

Hereunder, a series of image processing operations according to the present embodiment is described referring to FIG. 23, taking an OCTA en-face image as an example. FIG. 23 is a flowchart illustrating the series of image processing operations according to the present embodiment. Note that, the processing in step S2310 to step S2340 according to the present embodiment is the same as the processing in step S510 to step S540 in the first embodiment, and hence a description of the processing is omitted here. Note that, in a case where the image quality of an input image is to be improved unconditionally with regard to the imaging conditions, after performing the processing in step S2320, the processing in step S2330 can be omitted and the processing can shift to step S2340.

In step S2340, the image quality improving unit 404 performs image quality improving of the OCTA en-face image, and the processing then shifts to step S2350. In step S2350, the analyzing unit 2208 performs image analysis of the high quality image generated in step S2340. As the image analysis of the OCTA en-face image on which the image quality improving was performed, a place (vascular zone) that corresponds to a blood vessel can be detected from the image by applying any binarization processing. The area density can be analyzed by determining the proportion of the image occupied by the detected place that corresponds to a blood vessel. Further, by thinning the place that corresponds to a blood vessel subjected to binarization processing, images having a line width of 1 pixel can be obtained, and a proportion occupied by a blood vessel that does not depend on the thickness (also referred to as "skeleton density") can be determined. A configuration may be adopted so as to analyze the area and shape (circularity or the like) of an avascular zone (FAZ) using these images. As the method of analysis, the aforementioned numerical values may be calculated from the entire image, or a numerical value may be calculated with respect to a specified region of interest (ROI) based on an instruction of the examiner (user) input using a user interface (not illustrated). The ROI settings need not necessarily be specified by only the examiner, and the ROI may be a predetermined region that is automatically specified. The various parameters described above are examples of analysis results relating to blood vessels, and any parameter may be used as long as it is a parameter relating to a blood vessel. Note that, the analyzing unit 2208 may perform multiple kinds of image analysis processes. In other words, while an example of analysis relating to an OCTA en-face image has been described here, the kind of analysis that may be performed is not limited thereto, and analysis such as segmentation of retinal layers, layer thickness measurement, three-dimensional shape analysis of the papilla, and lamina cribrosa analysis may be performed with respect to an image obtained by OCT at the same time. In this regard, the analyzing unit 2208 may perform some or all of a plurality of kinds of image analysis processes in response to an instruction from the examiner input through any input apparatus.

In step S2360, the outputting unit 405 causes the display unit 20 to display the high quality image generated by the image quality improving unit 404 and the analysis result obtained by the analyzing unit 2208. Note that, the outputting unit 405 may output the high quality image and the analysis result to separate display units or apparatuses. Further, the outputting unit 405 may cause the display unit 20 to display only the analysis result. In addition, in a case where the analyzing unit 2208 outputs a plurality of analysis results, the outputting unit 405 may output some or all of the plurality of analysis results to the display unit 20 or another apparatus. For example, the outputting unit 405 may cause the display unit 20 to display an analysis result relating to a blood vessel in an OCTA en-face image as a two-dimensional map. Further, the outputting unit 405 may superimpose a value indicating an analysis result relating to a blood vessel in an OCTA en-face image onto the OCTA en-face image and cause the display unit 20 to display the resultant image.

As described above, the image processing apparatus 2200 according to the present embodiment further includes the analyzing unit 2208 that performs image analysis of a high quality image, and the outputting unit 405 causes an analysis result obtained by the analyzing unit 2208 to be displayed on the display unit 20. Thus, since a high quality image is used for image analysis by the image processing apparatus 2200 according to the present embodiment, the accuracy of the analysis can be improved.

Further, similarly to the first embodiment, the outputting unit 405 may output a generated high quality image to the imaging apparatus 10 or to another apparatus connected to the image processing apparatus 2200. Further, similarly to the first embodiment, the ground truth of the training data of the image quality improving engine is not limited to a high quality image obtained by performing averaging processing. In other words, a high quality image may be used that was obtained by performing at least one imaging method or processing among the imaging method and processing group including averaging processing, MAP estimation processing, smoothing filter processing, high-cost processing, and noise reduction processing.

Eighteenth Embodiment

Next, an image processing apparatus according to the eighteenth embodiment is described referring to FIG. 4. In the present embodiment, an example is described in which an image quality improving unit generates a high quality image by adding noise to images and learning noise components when performing learning.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

Figure 24:
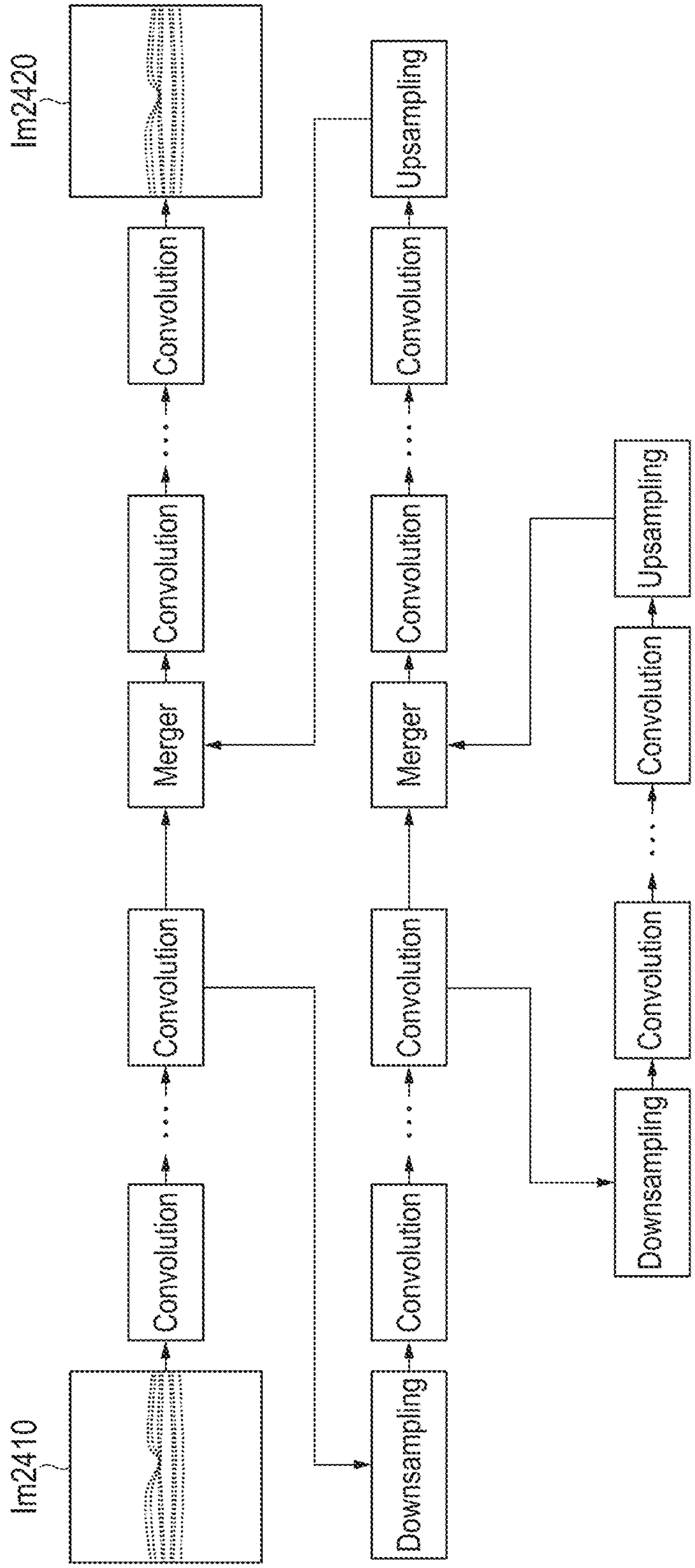
FIG. 24 is a view illustrating an example of a configuration of a neural network relating to image quality improving processing.

The obtaining unit 401 according to the present embodiment obtains an image as input data that is a processing object from the imaging apparatus 10 or another apparatus. A configuration example of a CNN in an image quality improving unit according to the present embodiment will be described using FIG. 24. FIG. 24 is a view illustrating one example of a configuration of a machine learning model in the image quality improving unit 404. The configuration illustrated in FIG. 24 is constituted by a plurality of layer groups that are responsible for processing to process an input value group for output. Note that, as illustrated in FIG. 24, the types of layers included in the configuration are a convolutional layer, a downsampling layer, an upsampling layer, and a merging layer. The convolutional layer is a layer that performs convolutional processing with respect to an input value group according to parameters such as the kernel size of the filters, the number of filters, the value of a stride, and the dilation value which are set. Note that, the number of dimensions of the kernel size of the filter may be changed according to the number of dimensions of an input image. The downsampling layer performs processing for making the number of output value groups less than the number of input value groups by thinning out or combining the input value groups. Specifically, for example, the processing is max pooling processing. The upsampling layer performs processing for making the number of output value groups greater than the number of input value groups by duplicating an input value group or adding a value interpolated from an input value group. Specifically, for example, the processing is linear interpolation processing. The merging layer is a layer that performs processing that inputs, from a plurality of sources, value groups such as an output value group of a certain layer or a pixel value group constituting an image, and merges the value groups by concatenating or adding the value groups. According to this configuration, a value group output upon a pixel value group constituting an input image Im2410 undergoing processing by the convolutional processing block, and the pixel value group constituting the input image Im2410 are merged by the merging layer. Thereafter, the merged pixel value group is formed into a high quality image Im2420 by the final convolutional layer. Note that, although not illustrated in the drawings, as a modification of the configuration of the CNN, for example, a batch normalization layer or an activation layer that uses a rectifier linear unit may be incorporated after the convolutional layer or the like.

The image quality improving engine of the present embodiment trains by receiving input of a low quality image generated by adding a first noise component to an image obtained from the imaging apparatus 10 or another apparatus, and as the ground truth, an image generated by adding a second noise component to an image obtained from the imaging apparatus 10 or another apparatus is adopted as a high quality image. In other words, as training images during learning according to the present embodiment, a common image is used as a low quality image and a high quality image, and the respective noise components of each of the images differ from each other. Because the same image is used as a low quality image and a high quality image, alignment when forming an image pair is unnecessary.

With respect to the noise components, Gaussian noise or noise modeled on characteristic noise of the target image or the like is added as noise. However, the first noise and second noise are different noise from each other. The term "different noise" means that the spatial location (pixel position) where the noise is added is different, or the value of the noise is different or the like. As characteristic noise of the target image, for example, in the case of OCT, noise can estimated based on data obtained by imaging in a state without a model eye or an eye to be examined, and can be used as a noise model. In the case of OCTA, noise based on noise which appears in the range of an avascular zone (FAZ), or noise that appears in an image obtained by imaging a model eye that schematically reproduces the flow of blood can be used as a noise model.

In the case of Gaussian noise, a standard deviation or a variance value is defined as the size of the noise, and noise is applied at random to the images based on those numerical values. A configuration may be adopted so that the average value as a whole is not changed as a result of applying random noise. In other words, a configuration is adopted so that the average value of noise added to each pixel of one image is zero. In this case, it is not required to adopt a configuration so that the average value becomes 0, and it suffices that noise with different patterns to each other can be added to the input data and the ground truth. Further, it is not necessary to add noise to both the input data and the ground truth, and noise may be added to either one of the input data and the ground truth. In a case where noise is not added, for example, although a false image of a blood vessel may appear in the image after image quality improving, it can also be considered that this occurs in a case where a difference between the images before and after image quality improving is comparatively large. Therefore, a configuration may be adopted so that a difference between the images before and after image quality improving is decreased. At such time, when performing learning, two images obtained by adding noise with different patterns to each other to a low quality image and a high quality image may be adopted as an image pair, or two images obtained by adding noise with different patterns to each other to a high quality image may be adopted as an image pair.

The outputting unit 405 causes the display unit 20 to display a high quality image which the image quality improving unit 404 generated. Note that, the outputting unit 405 may cause the display unit 20 to display the input image together with the high quality image.

The processing thereafter is the same as the processing in the first embodiment, and hence a description of the processing is omitted here.

Note that, although in the present embodiment a high quality image is generated using images generated by obtaining a low quality image from the imaging apparatus 10 or another apparatus, and adding a first noise component and a second noise component that is different from the first noise component to the low quality image, respectively, a configuration for performing these processing operations is not limited to the foregoing configuration. For example, with respect to the image to which the noise is added, a configuration may be adopted so that a first and a second noise component are added to a high quality image that underwent averaging processing as described in the first embodiment. In other words, a configuration may be adopted in which learning is performed that adopts an image obtained by adding a first noise component to an image generated by averaging processing as a low quality image, and adopts an image obtained by adding a second noise component to an image generated by averaging processing as a high quality image.

In addition, although an example of learning that uses first and second noise components is described in the present embodiment, the learning method is not limited thereto. For example, a configuration may be adopted for performing learning by adding a first noise component only to an image to be adopted as a low quality image and not adding a noise component to an image to be adopted as a high quality image. An image used at such time may be an image obtained from the imaging apparatus 10 or another apparatus, or an image generated by subjecting the aforementioned image to averaging processing as a processing object.

In addition, the size of the noise component may be dynamically changed for each kind of input image or for each rectangular region image to be learned. Specifically, adding noise which has a large value increases the effect of removing noise, and adding noise which has a small value decreases the effect of removing noise. Therefore, for example, a configuration may be adopted so as to perform learning by adjusting the noise that is added according to the conditions or type of the overall image or a rectangular region image, such as by reducing the value of a noise component to be added in the case of a dark image and increasing the value of a noise component to be added in the case of a bright image.

Note that, while imaging conditions of an image are not explicitly specified in the present embodiment, learning is performed using images of various imaging ranges and obtained with different numbers of scans, and front images of different imaged sites and different depths and the like.

In the above description, an image obtained from the imaging apparatus 10 or another apparatus, a noise image generated by adding noise to the aforementioned image, an image generated by averaging processing, and an image generated by adding noise to an image generated by averaging processing have been described. However, combinations of these images are not limited to the combinations described above, and any combination of a low quality image and a high quality image may be used.

Nineteenth Embodiment

Figure 25:
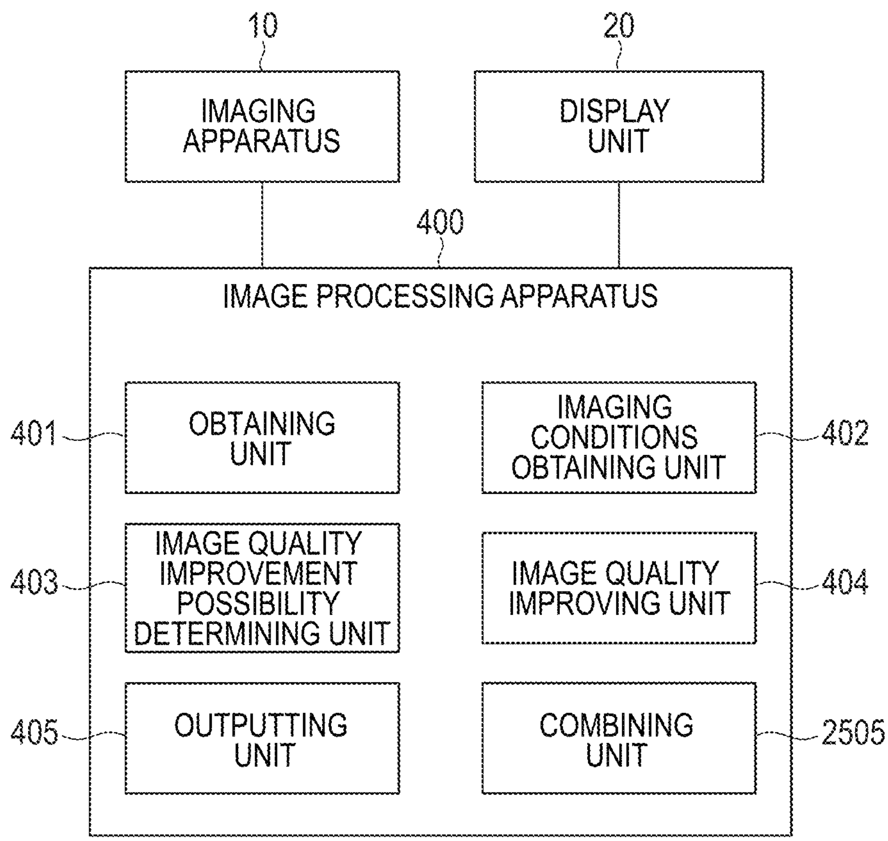
FIG. 25 is a view illustrating an example of a schematic configuration of an image processing apparatus according to a nineteenth embodiment.
Figure 26:
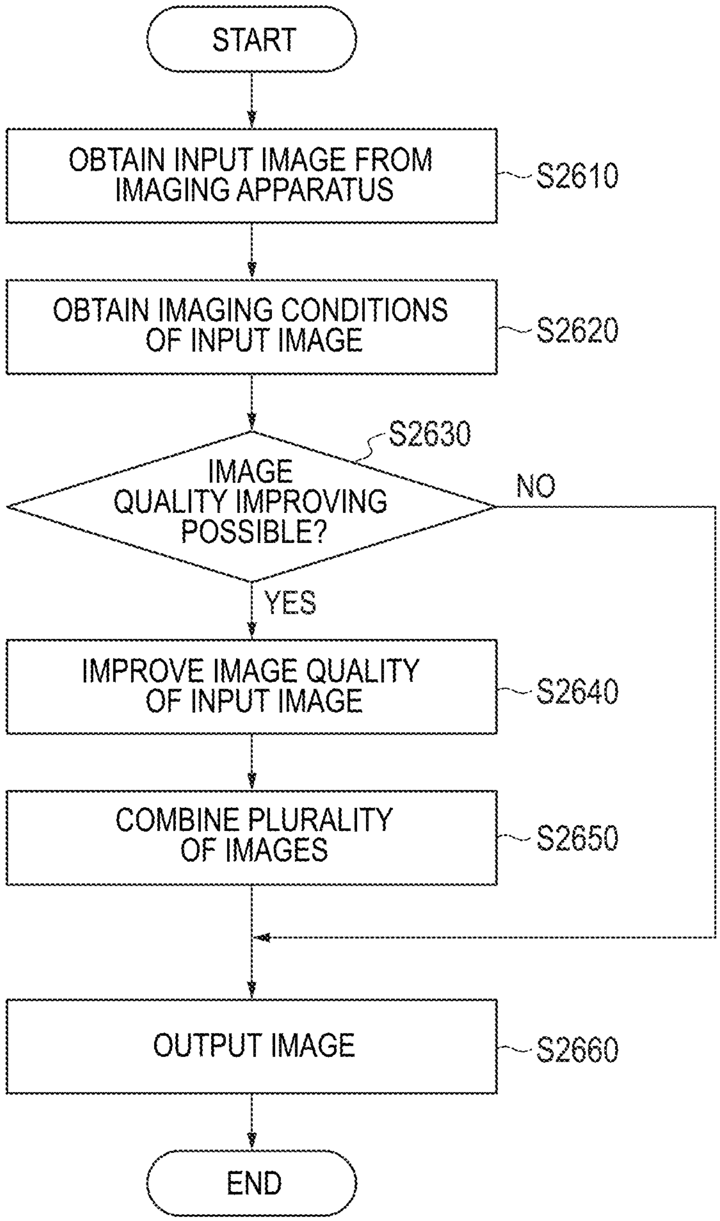
FIG. 26 is a flowchart illustrating an example of a flow of image processing according to the nineteenth embodiment.

Next, an image processing apparatus according to a nineteenth embodiment is described referring to FIG. 25 and FIG. 26. In the present embodiment, an image quality improving unit includes a plurality of image quality improving engines, and generates a plurality of high quality images with respect to an input image. Further, an example is described in which a combining unit 2505 combines a plurality of high quality images output from the plurality of image quality improving engines.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The obtaining unit 401 according to the present embodiment obtains an image as input data that is a processing object from the imaging apparatus 10 or another apparatus.

The image quality improving unit 404 according to the present embodiment includes a plurality of image quality improving engines, similarly to the second embodiment. Each of the plurality of image quality improving engines performed learning using different training data to each other with regard to at least one imaging condition among the imaged site, the imaging angle of view, a front image at different depths, a noise component, and the image resolution. The image quality improving unit 404 generates a high quality image using a plurality of image quality improving engines according to at least one imaging condition among the imaged site, the imaging angle of view, a front image at different depths, a noise component and the image resolution of the input image.

FIG. 26 is a flowchart illustrating a series of image processing operations according to the present embodiment. Note that, the processing in step S2610 and step S2620 according to the present embodiment is the same as the processing in step S510 and step S520 in the first embodiment, and hence a description of the processing is omitted here. Note that, in a case where the image quality of an input image is to be improved unconditionally with regard to the imaging conditions, after performing the processing in step S2620, the processing in step S2630 can be omitted and the processing can shift to step S2640.

In step S2620, similarly to the first embodiment, upon the imaging conditions obtaining unit 402 obtaining the imaging conditions group of the input image, the processing shifts to step S2630. In step S2630, similarly to the second embodiment, the image quality improvement possibility determining unit 403 uses the obtained imaging conditions group to determine whether or not any of the image quality improving engines which the image quality improving unit 404 includes can handle the input image.

If the image quality improvement possibility determining unit 403 determines that none of the group of image quality improving engines is capable of handling the input image, the processing shifts to step S2660. On the other hand, if the image quality improvement possibility determining unit 403 determines that any of the group of image quality improving engines is capable of handling the input image, the processing shifts to step S2640. Note that, depending on the settings or implementation form of the image processing apparatus 400, similarly to the first embodiment, even if it is determined that some of the imaging conditions cannot be handled by any of the image quality improving engines, the processing in step S2640 may be executed.

In step S2640, the image quality improving unit 404 inputs the input image obtained in step S2610 to each of the group of image quality improving engines, to thereby generate a high quality image group.

In step S2650, the combining unit 2505 combines several high quality images among the high quality image group generated in step S2640. Specifically, for example, results of two high quality images are combined which are a high quality image generated as a result of processing by a first image quality improving engine that learned using an image pair composed of a low quality image obtained from the imaging apparatus 10 and a high quality image obtained by performing the image quality improving processing such as the averaging processing with respect to an image group obtained by imaging a low quality image a plurality of times as described in the first embodiment, and a high quality image generated as a result of processing by a second image quality improving engine that learned using an image pair obtained by adding noise to images as described in the eighteenth embodiment. As the combining method, a method can be adopted in which combining is performed using averaging or weighted averaging or the like.

In step S2660, the outputting unit 405 causes the image generated by combining the images in step S2650 to be displayed on the display unit 20 or outputs the image to another apparatus. However, if it was determined in step S2630 that it is not possible to process the input image, the outputting unit 405 outputs the input image as the output image. Note that, in a case where the examiner instructs to display the input image or a case where it is not possible to process the input image, the outputting unit 405 may cause the display unit 20 to display information indicating that the output image is the same as the input image.

Twentieth Embodiment

Next, an image processing apparatus according to a twentieth embodiment is described referring to FIG. 4. In the present embodiment, an example is described of an image quality improving unit in which a second image quality improving engine generates a high quality image using an output result of a first image quality improving engine.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

The obtaining unit 401 according to the present embodiment obtains an image as input data that is a processing object from the imaging apparatus 10 or another apparatus.

The image quality improving unit 404 according to the present embodiment includes a plurality of image quality improving engines which are same as the image quality improving engine provided in the first embodiment. The image quality improving unit of the present embodiment includes a first image quality improving engine that learned using a low quality image obtained as input data from the imaging apparatus 10 or another apparatus, and a medium quality image generated from a plurality of low quality images as ground truth. In addition, the image quality improving unit includes a second image quality improving engine that learned using an image output from the first image quality improving engine, and an image with higher image quality than the medium quality image as ground truth. Note that, since the medium quality image is the same as in the fourteenth embodiment, a description of the medium quality image is omitted here.

The outputting unit 405 causes the display unit 20 to display a high quality image which the image quality improving unit 404 generated. Note that, the outputting unit 405 may cause the display unit 20 to display an input image together with the high quality image, and in such a case the outputting unit 405 may cause the display unit 20 to display information indicating that the input image is an image generated from a plurality of low quality images.

Next, a series of image processing operations according to the present embodiment is described referring to FIG. 5. Note that, the processing in step S510 to step S530 according to the present embodiment is the same as the processing in these steps in the first embodiment, and hence a description of the processing is omitted here.

In step S540, the image quality improving unit 404 improves the image quality of the input image using the image quality improving engine, to thereby generate a high quality image that is more suitable for image diagnosis than the input image. Specifically, the image quality improving unit 404 inputs the input image to the first image quality improving engine to cause the first image quality improving engine to generate a first high quality image subjected to image quality improving. In addition, the image quality improving unit 404 inputs the first high quality image to the second image quality improving engine to obtain a second high quality image. Each image quality improving engine generates a high quality image obtained by performing averaging processing using the input image based on a machine learning model which performed machine learning using training data. Thus, each image quality improving engine can generate a high quality image in which noise is reduced or contrast is enhanced compared to the input image.

The processing thereafter is the same as the processing in the first embodiment, and hence a description of the processing is omitted here.

Note that, although in the present embodiment a high quality image is generated using the first image quality improving engine that learned using a pair composed of a low quality image obtained from the imaging apparatus 10 or another apparatus and a medium quality image, and the second image quality improving engine that learned using a pair composed of a first high quality image and a high quality image, a configuration for performing such processing is not limited to the foregoing configuration. For example, a configuration may be adopted in which a pair of images used for learning by the first image quality improving engine are images with which the engine learns noise as described in the eighteenth embodiment, and the second image quality improving engine learns using a pair composed of a first high quality image and a high quality image. As the opposite configuration, a configuration may be adopted that includes a first image quality improving engine that learned using a pair composed of a low quality image and a medium quality image, and the second image quality improving engine that learned using images obtained by adding noise to the first high quality image.

In addition, the first image quality improving engine and the second image quality improving engine may each be configured as an engine that learns using noise as described in the eighteenth embodiment. In this case, for example, the first image quality improving engine learns using a pair composed of images obtained by adding a first noise and a second noise to a high quality image generated using an image generated by averaging processing, and the second image quality improving engine learns using a pair composed of images obtained by adding a first noise and a second noise to a first high quality image generated by the first image quality improving engine. Note that, although in the present embodiment a configuration that includes two image quality improving engines is described, the present invention is not limited thereto, and a configuration may be adopted in which a third engine and a fourth engine are further connected to perform processing. By cleaning the images to be used for learning, a network that can easily generate smoother and sharper images is constructed.

Twenty-First Embodiment

Figure 27:
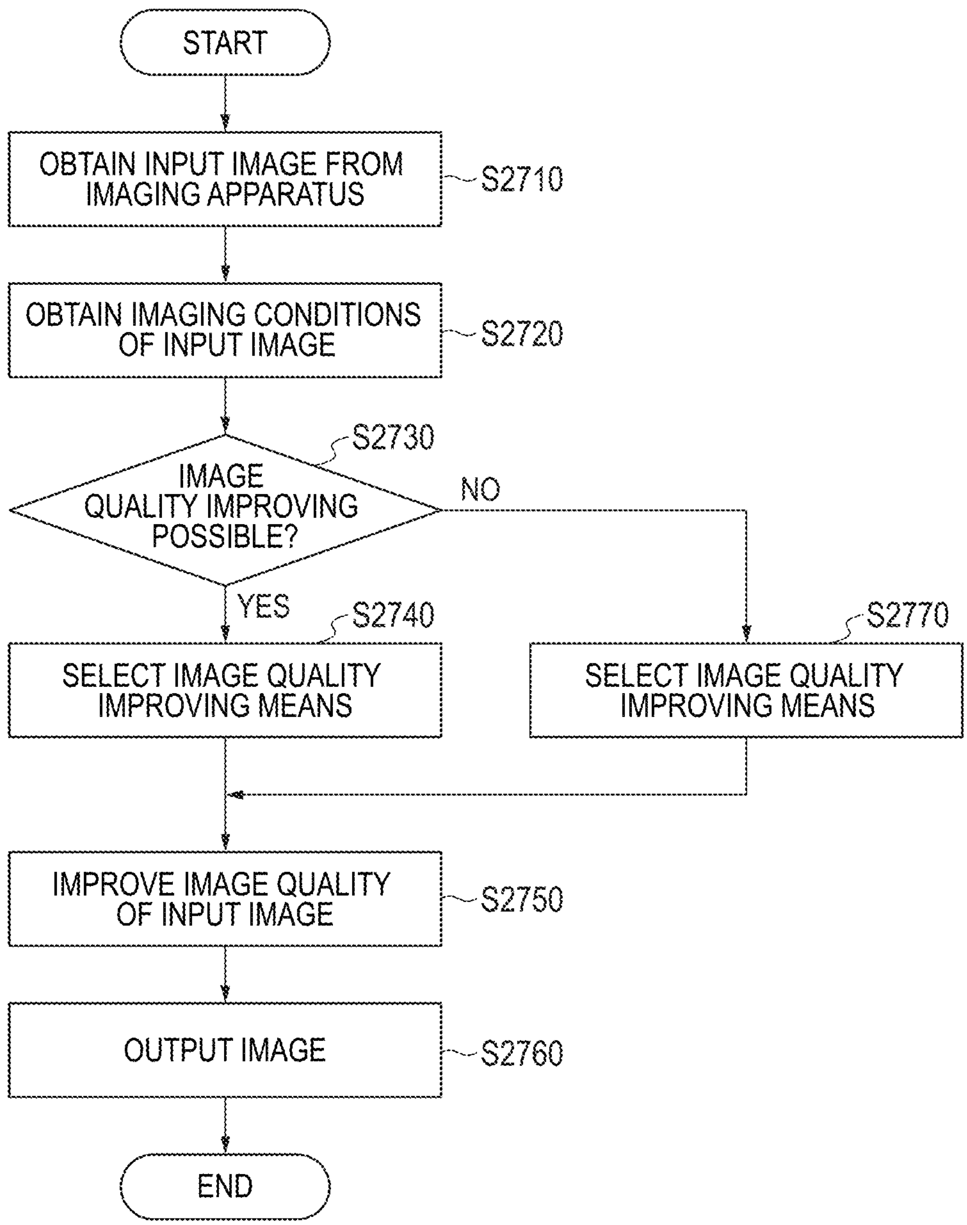
FIG. 27 is a flowchart illustrating an example of a flow of image processing according to a twenty-first embodiment.

Next, an image processing apparatus according to a twenty-first embodiment is described referring to FIG. 4 and FIG. 27. In the first embodiment, the image quality improving unit 404 includes one image quality improving engine. In contrast, in the present embodiment, an image quality improving unit includes a plurality of image quality improving engines which performed machine learning using different training data to each other, and generates a plurality of high quality images with respect to an input image.

Unless explicitly stated otherwise, the configuration and processing of the image processing apparatus according to the present embodiment are the same as the image processing apparatus 400 according to the second embodiment. Therefore, hereunder, the image processing apparatus according to the present embodiment is described centering on differences from the image processing apparatus according to the first and second embodiments. Note that, since the configuration of the image processing apparatus according to the present embodiment is the same as the configuration of the image processing apparatus according to the first and second embodiments, components illustrated in FIG. 4 are denoted by the same reference numerals as in the first and second embodiments, and a description of the components is omitted hereunder.

The image quality improving unit 404 according to the present embodiment includes two or more image quality improving engines which performed machine learning using different training data to each other. The method for creating a training data group according to the present embodiment will now be described. First, a pair group composed of a source image as input data and an averaged image as ground truth is prepared by performing imaging to obtain images of various imaging ranges and with different numbers of scans. Taking the case of OCT or OCTA as an example, for example, pairs of a first image group obtained by imaging 300 A-scans and 300 B-scans in a 3×3 mm range, and pairs of a second image group obtained by imaging 500 A-scans and 500 B-scans in a 10×10 mm range are created. At this time, there is a twofold difference in the scanning density between the pairs of the first image group and the pairs of the second image group. Therefore, these image groups are grouped as separate groups. Further, in a case where there is an image group obtained by imaging 600 A-scans and 600 B-scans in a 6×6 mm range, this image group is grouped in the same group as the first image group. In other words, in this case, image groups for which the scanning density is the same or almost the same (a tolerance of about 10%) are grouped in the same group.

Next, pair groups are grouped for each scanning density to create a training data group. For example, a training data group is created by creating first training data composed of pair groups obtained by imaging with a first scanning density, and creating second training data composed of pair groups obtained by imaging with a second scanning density.

Thereafter, the respective image quality improving engines are caused to perform machine learning using the respective sets of training data. For example, an image quality improving engine group is prepared that includes a first image quality improving engine corresponding to a machine learning model trained using the first training data, and a second image quality improving engine corresponding to a machine learning model trained using the second training data.

Because different training data is used for training the respective machine learning models corresponding to each of these image quality improving engines, the degree to which each of these image quality improving engines can improve the image quality of an input image input to the image quality improving engines will differ according to the imaging conditions of the input image. Specifically, in the case of the first image quality improving engine, the degree of image quality improving with respect to an input image obtained by imaging with the first scanning density is high, and the degree of image quality improving with respect to an image obtained by imaging with the second scanning density is low. Similarly, in the case of the second image quality improving engine, the degree of image quality improving with respect to an input image obtained by imaging with the second scanning density is high, and the degree of image quality improving with respect to an image obtained by imaging with the first scanning density is low.

On the other hand, in some cases a sufficient number of images of various imaging ranges and different scanning densities cannot be gathered as training data when performing learning. In this case, as described in the eighteenth embodiment, image quality improving engines that learned noise components are prepared with respect to those image groups.

Since an image quality improving engine that learned noise components is not easily influenced by the scanning density at the time of imaging, the image quality improving engine in question is applied when an image with an unlearned scanning density is input.

Since each set of training data is composed of pair groups grouped according to the scanning density, the image quality tendencies of image groups constituting the relevant pair groups are similar to each other. Therefore, if the scanning density corresponds to the training data used for training the image quality improving engine in question, the image quality improving engine can perform image quality improving more effectively than the image quality improving engine according to the first embodiment. Note that, an imaging condition for grouping pairs of the training data is not limited to the scanning density, and may be the imaged site, images at different depths with respect to a front image, or a combination of two or more of these conditions.

Hereunder, a series of image processing operations according to the present embodiment is described referring to FIG. 27. FIG. 27 is a flowchart illustrating the series of image processing operations according to the present embodiment. Note that, since the processing of step S2710 and step S2720 is the same as in step S510 and step S520 according to the first embodiment, a description of the processing is omitted here.

Upon the imaging conditions of the input image being obtained in step S2720, the processing shifts to step S2730. In step S2730, the image quality improvement possibility determining unit 403 uses the imaging conditions group obtained in step S2720 to determine whether or not any of the group of image quality improving engines which the image quality improving unit 404 includes can handle the input image.

If the image quality improvement possibility determining unit 403 determines that the imaging conditions are outside the range of imaging conditions which can be handled, the processing shifts to step S2770. On the other hand, if the image quality improvement possibility determining unit 403 determines that the imaging conditions are within the range of imaging conditions which can be handled, the processing shifts to step S2740.

In step S2740, the image quality improving unit 404 selects the image quality improving engine to perform image quality improving processing from the image quality improving engine group, based on the imaging conditions of the input image obtained in step S2720 and information pertaining to the training data of the image quality improving engine group. Specifically, for example, the image quality improving unit 404 selects an image quality improving engine which, with respect to the scanning density in the imaging conditions group obtained in step S2720, has information of training data relating to the scanning density and for which the degree of image quality improving is high. In the aforementioned example, if the scanning density is the first scanning density, the image quality improving unit 404 selects the first image quality improving engine.

On the other hand, in step S2770 the image quality improving unit 404 selects an image quality improving engine that learned noise components.

In step S2750, the image quality improving unit 404 generates a high quality image by subjecting the input image to image quality improving using the image quality improving engine selected in step S2740 or step S2770. Thereafter, in step S2760, the outputting unit 405 outputs the high quality image generated in step S2750 and causes the display unit 20 to display the high quality image. Note that, when causing the display unit 20 to display the high quality image, the outputting unit 405 may also cause the display unit 20 to display information indicating that the high quality image was generated using an image quality improving engine selected by the image quality improving unit 404.

As described above, the image quality improving unit 404 according to the present embodiment includes a plurality of image quality improving engines which performed learning using different training data to each other. Here, each of the plurality of image quality improving engines performed learning using different training data to each other with regard to at least one imaging condition among the imaged site, the imaging angle of view, a front image at different depths, and the image resolution. In addition, with respect to data for which correct answer data (ground truth) could not be sufficiently collected, the image quality improving engine is an engine that performed learning using noise components. The image quality improving unit 404 generates a high quality image using an image quality improving engine corresponding to at least one of these imaging conditions.

By this configuration, the image processing apparatus 400 according to the present embodiment can generate a more effective high quality image.

Twenty-Second Embodiment

Next, an image processing apparatus according to a twenty-second embodiment is described referring to FIG. 30 to FIG. 32C. In the present embodiment, a wide-angle image generating unit generates a wide-angle image (panorama image) using a plurality of high quality images generated by an image quality improving unit.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

Figure 31A:
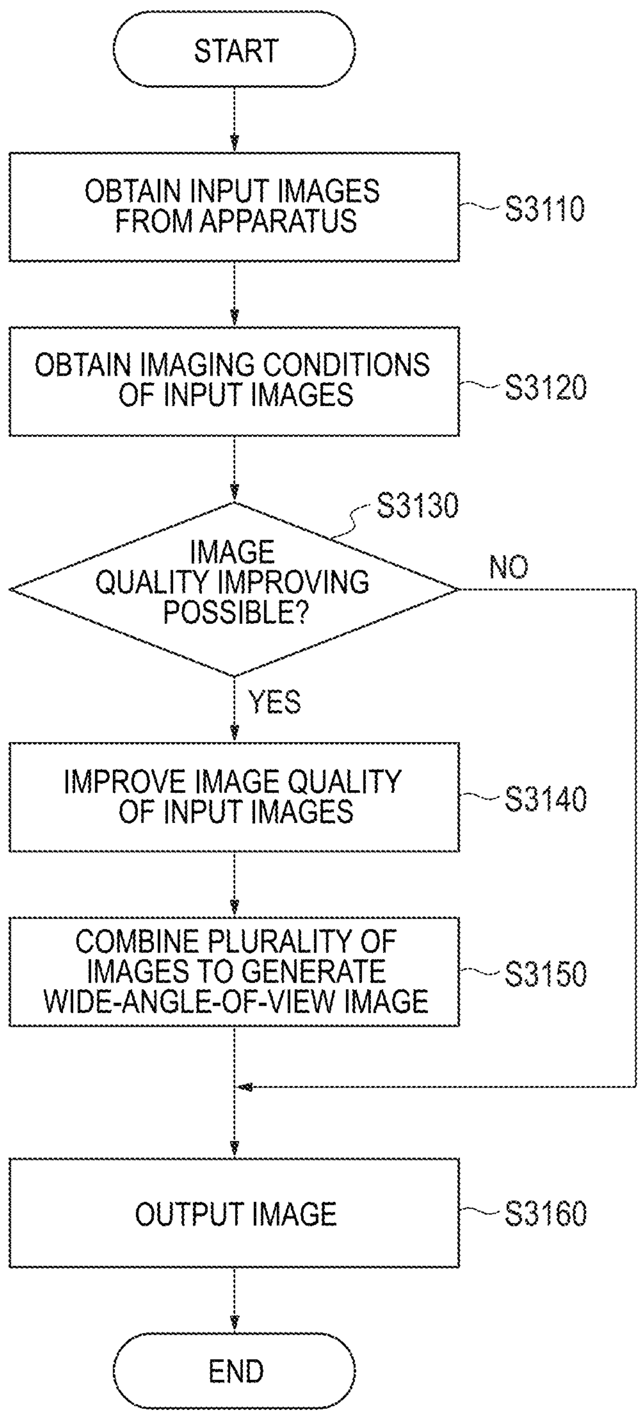
FIG. 31A is a flowchart illustrating an example of a flow of image processing according to the twenty-second embodiment.
Figure 32A:
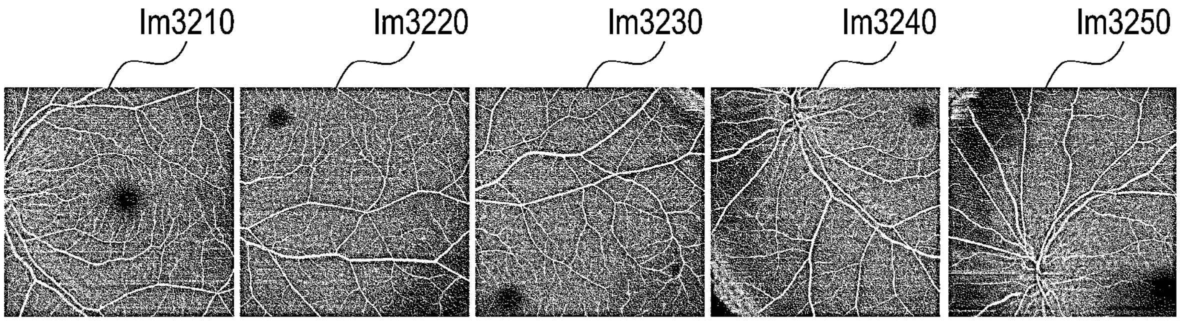
FIG. 32A is a multi-view drawing for describing a wide-angle image according to the twenty-second embodiment.

FIG. 31A is a flowchart illustrating a series of image processing operations according to the present embodiment. In step S3110, the obtaining unit 401 obtains a plurality of images (at least two images) as input data from the imaging apparatus 10 or another apparatus. The plurality of images are images obtained by imaging different positions of the same subject (eye to be examined or the like), and are images obtained by imaging a place where one part of the images overlaps, without completely overlapping with respect to the subject. A case where an eye to be examined is imaged will be described as an example. In this case, during imaging, the position of a fixation lamp is changed and the eye to be examined gazes steadily at the fixation lamp, and as a result images can be obtained in which different places of the same eye to be examined have been imaged. Note that, when performing imaging to obtain the images, it is desirable to perform the imaging while changing the position of the fixation lamp so that at least a proportion of about 20% of overlapping regions of adjacent images are images of the same place. In FIG. 32A, an example of OCTA en-face images imaged by changing the position of the fixation lamp so that, in adjacent images, a part of each image overlaps with each other is illustrated. In FIG. 32A, an example of in which the position of the fixation lamp was changed so that different places were imaged a total of five times is illustrated. Note that, although five images are illustrated as an example in FIG. 32A, the number of images is not limited to five and it suffices that the number of images is two or more.

Note that, the processing in step S3120 according to the present embodiment is the same as the processing in step S520 in the first embodiment, and hence a description of the processing is omitted here. Note that, in a case where the image quality of an input image is to be improved unconditionally with regard to the imaging conditions, after performing the processing in step S3120, the processing in step S3130 can be omitted and the processing can shift to step S3140.

In step S3120, similarly to the first embodiment, upon the imaging conditions obtaining unit 402 obtaining the imaging conditions group of each input image, the processing shifts to step S3130. In step S3130, similarly to the first embodiment, the image quality improvement possibility determining unit 403 uses each of the obtained imaging conditions groups to determine whether or not the image quality improving engine which the image quality improving unit 404 includes can handle the respective input images.

If the image quality improvement possibility determining unit 403 determines that the image quality improving engine is not capable of handling the plurality of input images, the processing shifts to step S3160. On the other hand, if the image quality improvement possibility determining unit 403 determines that the image quality improving engine is capable of handling the plurality of input images, the processing shifts to step S3140. Note that, depending on the settings or implementation form of the image processing apparatus 400, similarly to the first embodiment, even if it is determined that some of the imaging conditions cannot be handled by the image quality improving engine, the processing in step S3140 may be executed.

In step S3140, the image quality improving unit 404 executes processing with respect to the plurality of input images obtained in step S3110 to thereby generate a plurality of high quality images.

Figure 32B:
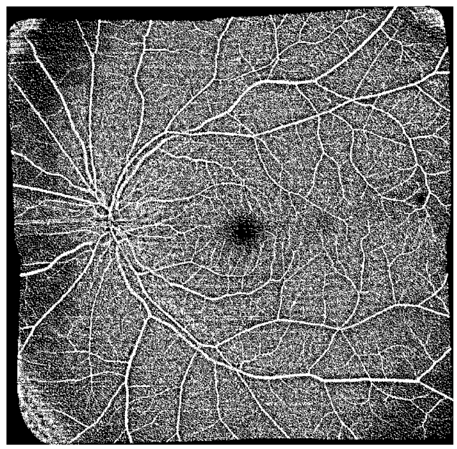
FIG. 32B is a view for describing the wide-angle image according to the twenty-second embodiment.
Figure 32C:
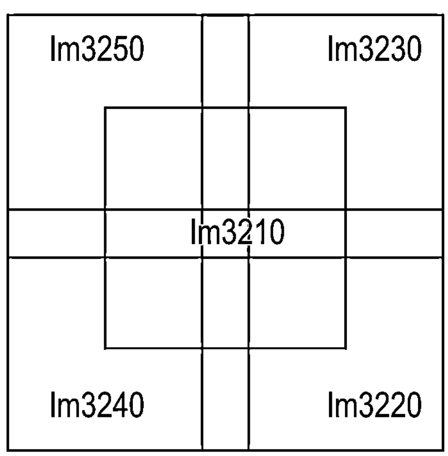
FIG. 32C is a view for describing the wide-angle image according to the twenty-second embodiment.

In step S3150, a wide-angle image generating unit 3005 combines a number of the high quality images among the high quality image group generated in step S3140. Specifically, an example will be described in which OCTA en-face images are taken as an example. The OCTA en-face images are imaged so that although the plurality of images do not completely overlap, partial regions of adjacent images overlap with each other. Therefore, the wide-angle image generating unit 3005 detects overlapping regions from the plurality of OCTA en-face images, and performs alignment using the overlapping regions. By modifying the OCTA en-face images based on an alignment parameter and combining the images, an OCTA en-face image of a wider range than a single OCTA en-face image can be generated. At this time, because the input plurality of OCTA en-face images were subjected to image quality improving in step S3140, the OCTA en-face image with a wide field of view output in step S3150 has already undergone image quality improving. An example of an OCTA en-face image with a wide field of view generated by the wide-angle image generating unit 3005 is illustrated in FIG. 32B. FIG. 32B illustrates an example generated by aligning the five images illustrated in FIG. 32A. The correlation between the positions of the images in FIG. 32A and FIG. 32B is illustrated in FIG. 32C. As illustrated in FIG. 32C, an image Im3210 is arranged at the center and images Im3220 to 3250 are arranged around the image Im3210. Note that, with regard to the OCTA en-face images, a plurality of OCTA en-face images can be generated by setting different depth ranges based on three-dimensional motion contrast data. Therefore, although an example of a surface layer image with a wide field of view is illustrated in FIG. 32B, the present invention is not limited thereto. For example, a configuration may be adopted in which alignment is performed using an OCTA en-face image (Im2910) of a surface layer illustrated in FIG. 29A, and OCTA en-face images of other depth ranges are modified using the parameters obtained with the OCTA en-face image Im2910. Alternatively, a color image is used as the input image for alignment, and a composite color image is generated in which RG components of the RGB components are adopted for the OCTA en-face image of the surface layer, and the B component is adopted for the OCTA en-face image that is the object of alignment. The alignment of a composite color OCTA en-face image obtained by combining a plurality of layers in the depth range into one image may then be performed. Thus, if only the B component is extracted from the aligned color OCTA en-face image, an OCTA en-face image with a wide field of view in which a target OCTA en-face image was aligned can be obtained. Note that, an object to be subjected to image quality improving is not limited to a two-dimensional OCTA en-face image, and may be a three-dimensional OCT image or three-dimensional motion contrast data itself. In such a case, alignment may be performed with the three-dimensional data to generate three-dimensional data of a wide range. A high-quality wide-angle image can be generated by cutting out an arbitrary cross section (any plane of XYZ is possible) or an arbitrary depth range (range in the Z-direction) from the three-dimensional data of a wide range.

In step S3160, the outputting unit 405 causes the image generated by combining a plurality of images in step S3150 to be displayed on the display unit 20 or outputs the image to another apparatus. However, if it was determined in step S3130 that it is not possible to process the input image, the outputting unit 405 outputs the input image as the output image. Note that, in a case where the examiner instructs to display the input image or a case where it is not possible to process the input image, the outputting unit 405 may cause the display unit 20 to display information indicating that the output image is the same as the input image.

Note that, although in the present embodiment high quality images are generated from a plurality of input images, respectively, and the high quality images are aligned to generate a final, single high-quality wide-angle image, a method for generating a single high quality image from a plurality of input images is not limited to this method. For example, in a different example of the image quality improving processing of the present embodiment illustrated in FIG. 31B, a configuration may be adopted so that one wide-angle image is first generated, and the wide-angle image is then subjected to image quality improving processing to finally generate a single high-quality wide-angle image.

Figure 31B:
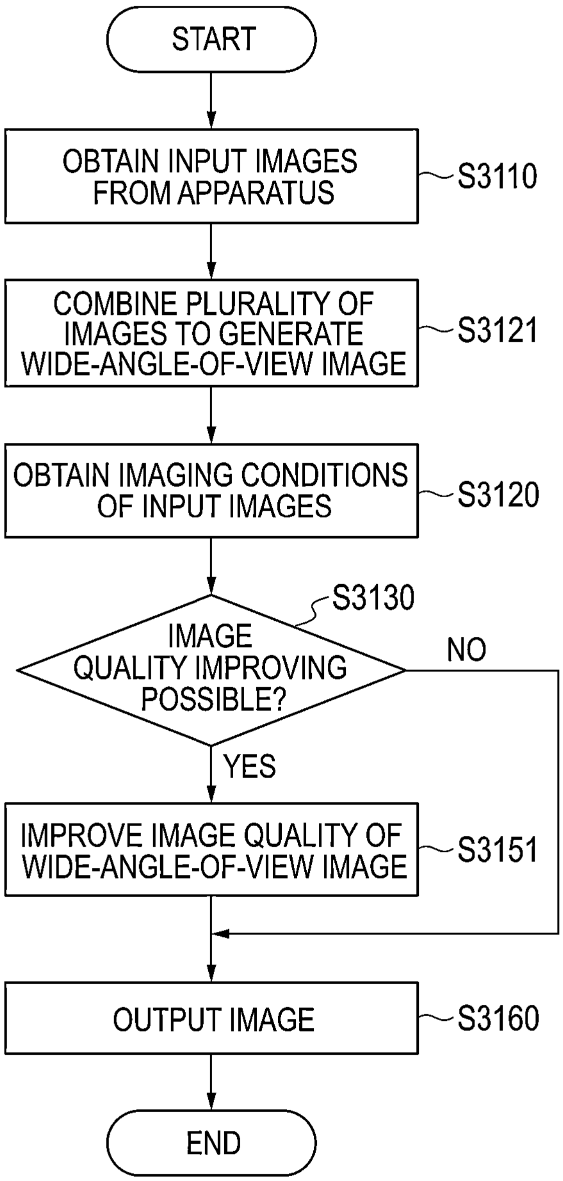
FIG. 31B is a flowchart illustrating an example of the flow of image processing according to the twenty-second embodiment.

This processing will now be described using FIG. 31B. In the following description, a description of a portion of the processing that is the same as in FIG. 31A is omitted.

In step S3121, the wide-angle image generating unit 3005 combines the plurality of images obtained in step S3110. When generating a wide-angle image, similarly to the description of the processing in step S3150, the input images are images obtained from the imaging apparatus 10 or another apparatus, although a difference from the processing in step S3150 is that the images are in a state prior to undergoing image quality improving.

In step S3151, the image quality improving unit 404 executes processing on the high quality image that the wide-angle image generating unit 3005 generated to thereby generate a single high-quality wide-angle image.

By this configuration, the image processing apparatus 400 according to the present embodiment can generate a wide-angle high quality image.

With regard to the aforementioned first to twenty-second embodiments, display of a high quality image on the display unit 20 by the outputting unit 405 is basically performed automatically in response to generation of a high quality image by the image quality improving unit 404 or the output of an analysis result by the analyzing unit 2208. However, display of a high quality image may be performed in response to an instruction from the examiner. For example, the outputting unit 405 may cause the display unit 20 to display an image selected according to an instruction from the examiner from among a high quality image generated by the image quality improving unit 404 and an input image. Further, in response to an instruction from the examiner, the outputting unit 405 may switch the image displayed on the display unit 20 from an imaged image (input image) to a high quality image. In other words, the outputting unit 405 may change the display of a low quality image to the display of a high quality image in response to an instruction from the examiner. Further, the outputting unit 405 may change the display of a high quality image to the display of a low quality image in response to an instruction from the examiner. In addition, the image quality improving unit 404 may start (input an image to the image quality improving engine) image quality improving processing by the image quality improving engine in response to an instruction from the examiner, and the outputting unit 405 may cause the display unit 20 to display a high quality image generated by the image quality improving unit 404. In contrast, when an input image is imaged by the imaging apparatus 10, the image quality improving engine may automatically generate a high quality image based on the input image, and the outputting unit 405 may cause the display unit 20 to display the high quality image in response to an instruction from the examiner. Note that, these processing operations can be similarly performed with respect to the output of an analysis result also. In other words, the outputting unit 405 may change the display of an analysis result for a low quality image to the display of an analysis result for a high quality image in response to an instruction from the examiner. Further, the outputting unit 405 may change the display of an analysis result for a high quality image to the display of an analysis result for a low quality image in response to an instruction from the examiner. Naturally, the outputting unit 405 may change the display of an analysis result for a low quality image to the display of a low quality image in response to an instruction from the examiner. Further, the outputting unit 405 may change the display of a low quality image to the display of an analysis result for a low quality image in response to an instruction from the examiner. Furthermore, the outputting unit 405 may change the display of an analysis result for a high quality image to the display of a high quality image in response to an instruction from the examiner. Further, the outputting unit 405 may change the display of a high quality image to the display of an analysis result for a high quality image in response to an instruction from the examiner. In addition, the outputting unit 405 may change the display of an analysis result for a low quality image to the display of a different kind of analysis result for a low quality image in response to an instruction from the examiner. Further, the outputting unit 405 may change the display of an analysis result for a high quality image to the display of a different kind of analysis result for a high quality image in response to an instruction from the examiner. In this case, the display of an analysis result for a high quality image may be performed such that the analysis result for the high quality image is displayed in a superimposed manner on the high quality image with any degree of transparency. Further, the display of an analysis result for a low quality image may be performed such that the analysis result for the low quality image is displayed in a superimposed manner on the low quality image with any degree of transparency. At this time, changing to the display of an analysis result may be, for example, a change to a state in which the analysis result is superimposed with any degree of transparency on the image that is being displayed. Further, changing to the display of an analysis result may be, for example, a change to the display of an image (for example, a two-dimensional map) obtained by subjecting an analysis result and an image to blending processing with any degree of transparency. In addition, the image processing apparatus may be configured to start processing by an imaged location estimating engine, an image quality evaluating engine, an authenticity evaluating engine or an evaluating unit in response to an instruction from the examiner. Note that, with regard to the first to twenty-second embodiments described above, the form in which the outputting unit 405 causes the display unit 20 to display a high quality image may be any form. For example, the outputting unit 405 may cause an input image and a high quality image to be displayed side by side, or may switch the display between an input image and a high quality image. Further, the outputting unit 405 may cause an input image and a high quality image to be displayed in sequential order in accordance with the imaged site, the imaging date and time, or the facility where imaging was performed or the like. Similarly, the outputting unit 405 may cause image analysis results obtained using a high quality image or the like to be displayed in sequential order in accordance with any imaging condition of the high quality image or of an input image corresponding to the high quality image. In addition, the outputting unit 405 may cause image analysis results obtained using a high quality image to be displayed in sequential order for each analysis item.

Twenty-Third Embodiment

Next, an image processing apparatus according to a twenty-third embodiment is described referring to FIG. 4, FIG. 29A, and FIG. 33A to FIG. 33C. In the present embodiment, learning is performed using training data composed of a pair group including ground truth that is a high quality image which corresponds to input data. At such time, a single image quality improving engine is generated using a plurality of items of ground truth of high image quality generated by a plurality of image quality improving engines.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment. Note that, since the configuration of the image processing apparatus according to the present embodiment is the same as the configuration of the image processing apparatus according to the first embodiment, components illustrated in FIG. 4 are denoted by the same reference numerals as in the first embodiment, and a description of the components is omitted hereunder.

Figure 33A:
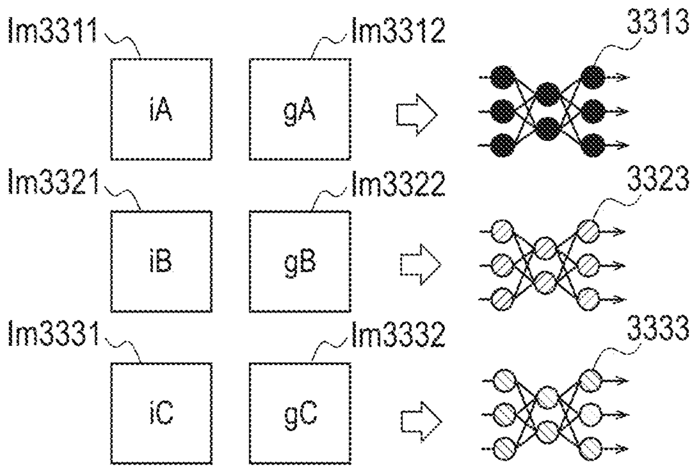
FIG. 33A is a view for describing image quality improving processing according to a twenty-third embodiment.

The obtaining unit 401 according to the present embodiment obtains an image, as input data, that is a processing object from the imaging apparatus 10 or another apparatus. The manner in which an image quality improving engine is generated in the image quality improving unit 404 according to the present embodiment will be described using FIG. 29A and FIG. 33A to FIG. 33C. Firstly, a first learning in the present embodiment will be described using FIG. 33A. FIG. 33A is a view illustrating an example of a plurality of pair groups of input data and ground truth, and a plurality of image quality improving engines. Reference characters Im3311 and Im3312 denote a pair group composed of input data and ground truth. For example, it is assumed that the pairs are a pair group with respect to a surface layer (Im2910) illustrated in FIG. 29A. Further, reference numeral 3313 denotes an image quality improving engine which performed learning using the pair group composed of Im3311 and Im3312. Note that, a method adopted for the learning illustrated in FIG. 33A may be a method that uses a high quality image generated by averaging processing as described in the first embodiment, or may be a method that learns noise components as described in the eighteenth embodiment. Alternatively, a combination of these methods may be adopted. Reference characters Im3321 and Im3322 denote a pair group composed of input data and ground truth, and for example are assumed to be a pair group with respect to a deep layer (Im2920) illustrated in FIG. 29A. Reference numeral 3323 denotes an image quality improving engine that performed learning using the pair group composed of Im3321 and Im3322. Similarly, reference characters Im3331 and Im3332 denote a pair group composed of input data and ground truth, and for example are assumed to be a pair group with respect to an outer layer (Im2930) illustrated in FIG. 29A. Further, reference numeral 3333 denotes an image quality improving engine that performed learning using the pair group composed of Im3331 and Im3332. In other words, in FIG. 33A learning is performed for each of the images. Therefore, for example, in the case of the noise components described in the eighteenth embodiment, learning can be performed using a noise parameter that is suitable for the respective images. At such time, the image quality improving engine can include a machine learning engine obtained using training data in which noise corresponding to the state of at least a partial region of a medical image is added to the at least partial region in question. Here, the aforementioned “noise corresponding to the state” may be, for example, noise of a size corresponding to a pixel value of the at least partial region. Further, for example, in a case where a feature in the at least partial region is small (for example, a pixel value is small or the contrast is low), the aforementioned "noise corresponding to the state" may be noise of a small size. Further, for example, in a case where a feature in the at least partial region is large (for example, a pixel value is large or the contrast is high), the aforementioned "noise corresponding to the state" may be noise of a large size. In addition, the image quality improving engine can include a machine learning engine obtained using training data including a plurality of front images to which noise of different sizes was added with respect to each of at least two depth ranges among a plurality of depth ranges. At this time, for example, a front image to which noise of a small size was added with respect to a depth range corresponding to a front image in which a feature is small (for example, a pixel value is small) may be adopted as training data. Further, for example, a front image to which noise of a large size was added with respect to a depth range corresponding to a front image in which a feature is large (for example, a pixel value is large) may be adopted as training data. Note that, a front image to which noise of a medium size is added with respect to a depth range corresponding to a front image in which a feature is of medium size may also be adopted as training data. Here, the plurality of depth ranges may be depth ranges in which one part of each of two depth ranges that are adjacent in the depth direction overlap with each other.

Figure 33B:
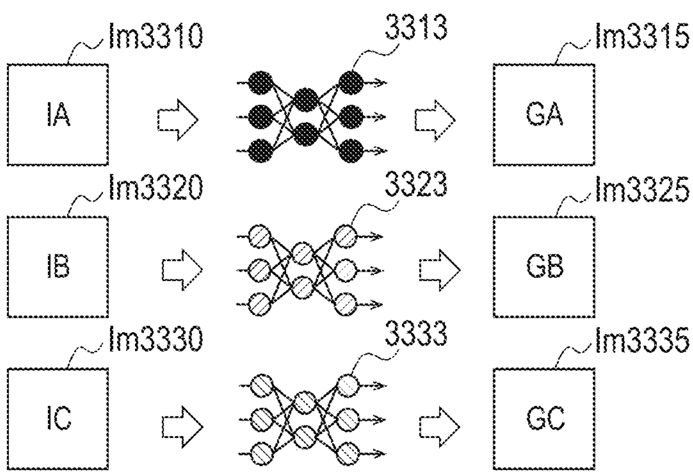
FIG. 33B is a view for describing the wide-angle image according to the twenty-third embodiment.

Next, inference of an image in the present embodiment will be described using FIG. 33B. In an example illustrated in FIG. 33B, an image is generated using the image quality improving engines 3313 to 3333 which learned as described above using FIG. 33A. For example, when a low-quality surface layer image Im3310 is input to the image quality improving engine 3313 that performed learning using a plurality of surface layer images, the image quality improving engine 3313 outputs a high-quality surface layer image Im3315. Further, when a low-quality deep layer image Im3320 is input to the image quality improving engine 3323 that performed learning using a plurality of deep layer images, the image quality improving engine 3323 outputs a high-quality deep layer image Im3325. Similarly, when a low-quality outer layer image Im3330 is input to the image quality improving engine 3333 that performed learning using a plurality of outer layer images, the image quality improving engine 3333 outputs a high-quality outer layer image Im3335.

Figure 33C:
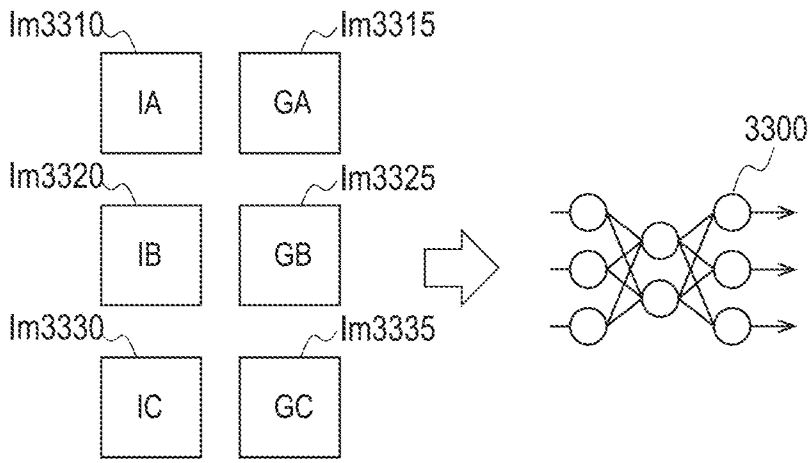
FIG. 33C is a view for describing the wide-angle image according to the twenty-third embodiment.

Next, a second learning according to the present embodiment will be described using FIG. 33C. FIG. 33C illustrates the manner in which one image quality improving engine 3300 learns using a plurality of image pair groups of different kinds. In FIG. 33C, reference characters Im3310 denote a low-quality surface layer image and reference characters Im3315 denote a high-quality surface layer image as a pair group, reference characters Im3320 denote a low-quality deep layer image and reference characters Im3325 denote a high-quality deep layer image as a pair group, and reference characters Im3330 denote a low-quality outer layer image and reference characters Im3335 denote high-quality outer layer image as a pair group. In other words, the image quality improving engine 3300 is generated using training data including pair groups composed of output data that is a high quality image generated using an image quality improving engine that learned by the first learning, and input data that is of low image quality. Thus, the image quality improving engine 3300 can generate a high quality image suitable for image diagnosis in which noise is reduced or which has high contrast from various kinds of input images.

The outputting unit 405 causes the display unit 20 to display a high quality image which the image quality improving unit 404 generated. Note that, the outputting unit 405 may cause the display unit 20 to display the input image together with the high quality image.

The processing thereafter is the same as the processing in the first embodiment, and hence a description of the processing is omitted here.

Note that, although in the present embodiment an OCTA en-face image has been described using three layers of different depths, the kinds of image are not limited thereto, and the kinds may be increased by generating OCTA en-face images for which different depth ranges are set by changing the layer that serves as a reference and an offset value. The differences between the kinds of images are not limited to differences in the depth direction, and may be differences for each site. For example, the differences may be differences between the locations that are imaged, such as the anterior ocular segment and the posterior ocular segment. In addition, the images are not limited to OCTA en-face images, and may be intensity en-face images generated from OCT data. Further, learning with respect to OCTA en-face images and intensity en-face images may be performed separately in the first learning, and learning with respect to the OCTA en-face images and intensity en-face images may be collectively performed in the second learning. In addition, the kinds of images need not be only en-face images, and may be images obtained with different kinds of imaging apparatuses, such as tomographic images, SLO images, fundus images and fluorescence fundus images.

Note that, although an example in which one image quality improving engine is generated by the second learning has been described, the number of generated image quality improving engines need not necessarily be one. It suffices that the configuration is the configuration of an image quality improving engine that performs learning using a pair group of output data of an image quality improving engine generated by the first learning, and input data of low image quality. In addition, with respect to the second learning, although an example in which learning is performed simultaneously using a plurality of image pair groups of different kinds is illustrated in FIG. 33C, the method of learning is not limited thereto, and may be transfer learning. For example, a configuration may be adopted in which, after learning with the pair group of the surface layer images Im3310 and Im3315, learning is performed with a pair group of the deep layer images Im3320 and Im3325 using that network, to thereby finally generate the image quality improving engine 3300.

By this configuration, the image quality improving unit 404 according to the present embodiment can generate a more effective high quality image with respect to various kinds of images.

Twenty-Fourth Embodiment

Figure 34A:
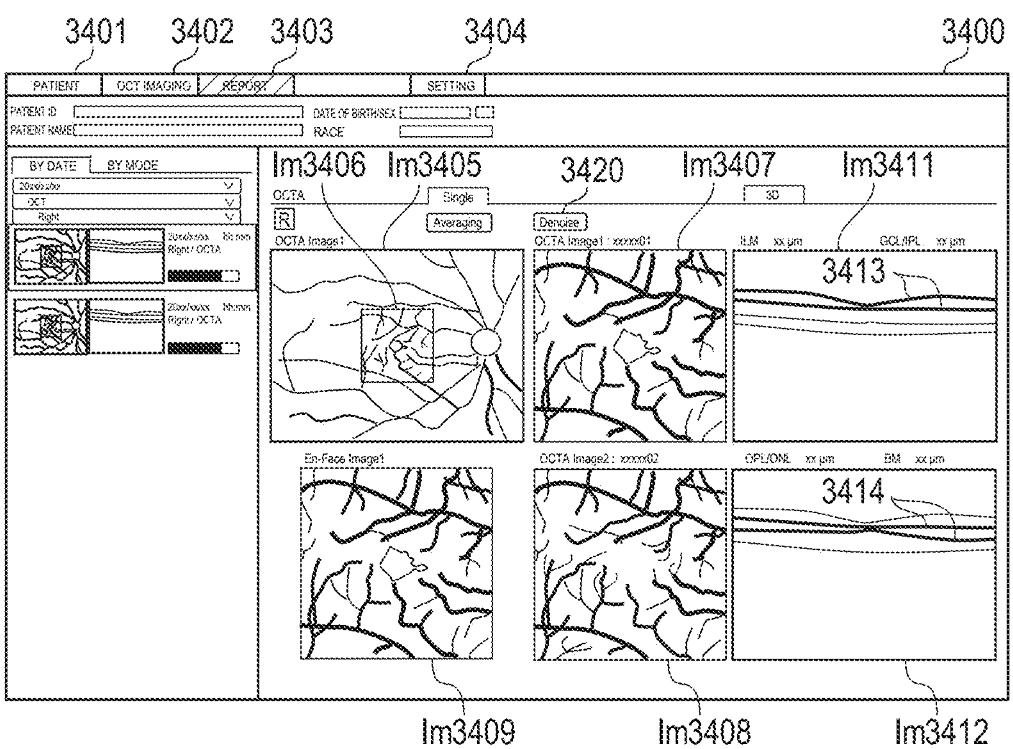
FIG. 34A is a view illustrating an example of a user interface according to a twenty-fourth embodiment.
Figure 34B:
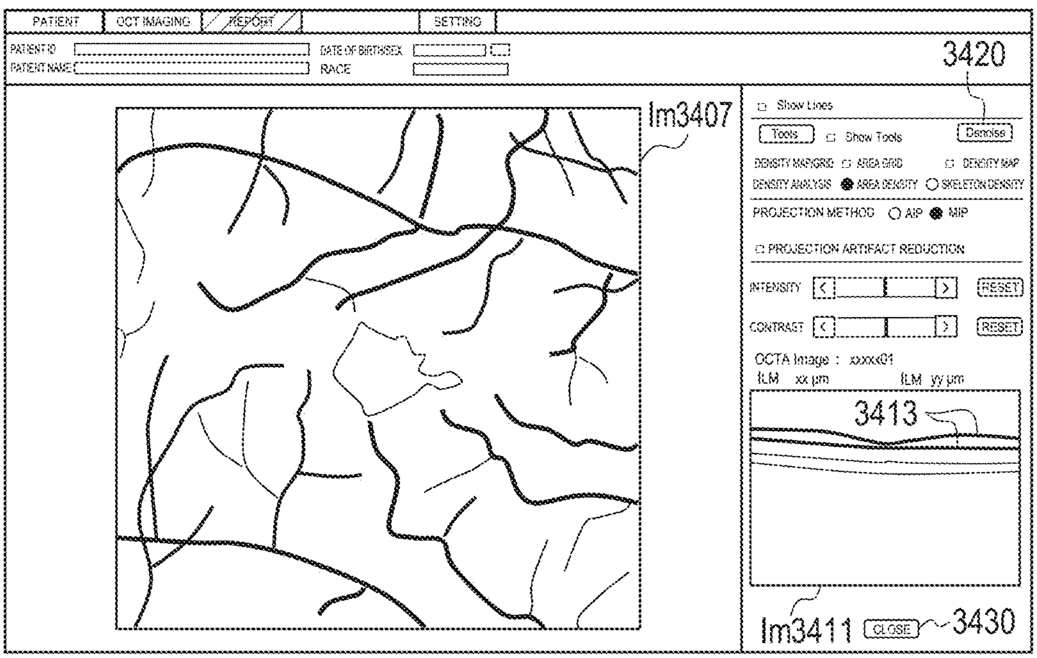
FIG. 34B is a view illustrating an example of a user interface according to the twenty-fourth embodiment.

Next, an image processing apparatus according to a twenty-fourth embodiment is described referring to FIG. 34A and FIG. 34B. In the present embodiment, an example is described in which the outputting unit 405 displays the result of processing by the image quality improving unit 404 on the display unit 20. Note that, although the present embodiment is described using FIG. 34A and FIG. 34B, the display screens are not limited to the examples illustrated in FIG. 34A and FIG. 34B. Image quality improving processing can also be similarly applied to a display screen that displays a plurality of images side-by-side obtained at different dates and times, as when performing a follow-up observation. Further, image quality improving processing can also be similarly applied to a display screen on which the examiner confirms whether or not the imaging is successful immediately after imaging, as in the case of an imaging confirmation screen.

Unless explicitly stated otherwise, the configuration and processing of the image processing apparatus according to the present embodiment are the same as the configuration and processing of the image processing apparatus 400 according to the first embodiment. Therefore, hereunder, the image processing apparatus according to the present embodiment is described centering on differences from the image processing apparatus according to the first embodiment.

The outputting unit 405 can cause the display unit 20 to display a plurality of high quality images which the image quality improving unit 404 generated or a low quality image on which image quality improving was not performed. Thus, the outputting unit 405 can output a low quality image and a high quality image, respectively, in accordance with an instruction of the examiner.

Hereunder, one example of an interface 3400 in question is described referring to FIG. 34A and FIG. 34B. Reference numeral 3400 denotes an entire screen, reference numeral 3401 denotes a "Patient" tab, reference numeral 3402 denotes an "Imaging" tab, reference numeral 3403 denotes a "Report" tab, and reference numeral 3404 denotes a "Setting" tab. Diagonal lines in the "Report" tab 3403 indicate an active state of a report screen. In the present embodiment an example of displaying the report screen will be described. Reference characters Im3405 denote an SLO image, and reference characters Im3406 denote an image in which an OCTA en-face image denoted by reference characters Im3407 is displayed in a superimposed manner on the SLO image Im3405. Here, the term "SLO image" refers to a front image of the fundus obtained by an SLO (Scanning Laser Ophthalmoscope) optical system (not illustrated). Reference characters Im3407 and Im3408 each denote an OCTA en-face image, reference characters Im3409 denote an intensity en-face image, and reference characters Im3411 and Im3412 each denote a tomographic image. Reference numerals 3413 and 3414 denote boundary lines of the upper and lower ranges of the OCTA en-face images denoted by Im3407 and Im3408, respectively, which are displayed in a superimposed manner on the corresponding tomographic images. A button 3420 is a button used for designating execution of image quality improving processing. Naturally, as described later, the button 3420 may be a button for inputting an instruction to display a high quality image.

In the present embodiment, execution of image quality improving processing is performed when the button 3420 is specified, or whether or not to execute image quality improving processing is determined based on information stored (saved) in a database. First, an example of switching between display of a high quality image and display of a low quality image by the button 3420 being specified in accordance with an instruction from the examiner will be described. Note that, an OCTA en-face image will be described as the target image of the image quality improving processing. When the examiner performs an operation to specify the "Report" tab 3403 to thereby transition to the report screen, the low-quality OCTA en-face images Im3407 and Im3408 are displayed. Thereafter, when the examiner performs an operation to specify the button 3420, the image quality improving unit 404 executes image quality improving processing on the images Im3407 and Im3408 displayed on the screen. After the image quality improving processing is completed, the outputting unit 405 displays a high quality image which the image quality improving unit 404 generated on the report screen. Note that, since the image denoted by reference characters Im3406 is an image obtained by displaying the image Im3407 in a superimposed manner on the SLO image Im3405, the image Im3406 is also an image that has been subjected to image quality improving processing. The display of the button 3420 is then changed to an active state to provide a display from which it can be understood that image quality improving processing was executed. In this case, execution of processing by the image quality improving unit 404 need not be limited to the timing at which the examiner performs an operation to specify the button 3420. Since the kind of the OCTA en-face images Im3407 and Im3408 to be displayed when the report screen is opened is known in advance, image quality improving processing may be executed when transitioning to the report screen. Subsequently, at the timing at which the button 3420 is pressed, the outputting unit 405 may display a high quality image on the report screen. In addition, it is not necessary that the number of kinds of image on which image quality improving processing is performed in response to an instruction from the examiner or when transitioning to the report screen is two. A configuration may be adopted so as to perform processing on images for which there is a high possibility of being displayed, for example, processing may be performed on a plurality of OCTA en-face images such as the surface layer (Im2910), the deep layer (Im2920), the outer layer (Im2930) and the choroidal vascular network (Im2940) illustrated in FIG. 29A. In this case, an image obtained by performing image quality improving processing may be temporarily stored in a memory or may be stored in a database.

Next, a case where image quality improving processing is executed based on information stored (saved) in a database is described. In a case where a state whereby execution of image quality improving processing is to be performed is stored in a database, upon the display transitioning to the report screen, a high quality image obtained by executing image quality improving processing is displayed by default. Further, a configuration can be adopted so that the button 3420 is displayed in an active state by default so that the examiner can thereby know that a high quality image obtained by executing image quality improving processing is being displayed. If the examiner wishes to display a low quality image in a state prior to image quality improving processing, the examiner can display the low quality image by performing an operation to specify the button 3420 to thereby release the active state. If the examiner wishes to return to the high quality image, the examiner specifies the button 3420. It is assumed that it can be specified whether or not to execute image quality improving processing on data stored in the database commonly for all of the data stored in the database, and with respect to respective classes of data such as for each set of imaging data (for each examination). For example, in a case where a state whereby image quality improving processing is to be executed for the entire database has been stored, if the examiner stored a state whereby image quality improving processing is not to be executed with respect to an individual item of imaging data (individual examination), the next time the relevant imaging data is displayed, the imaging data will be displayed in a state in which image quality improving processing has not been executed thereon. A user interface (not illustrated) (for example, a "Store" button) may be used to store a state in which image quality improving processing has been executed for each item of imaging data (for each examination). Further, when transitioning to other imaging data (another examination) or other patient data (for example, changing to a display screen other than the report screen in accordance with an instruction from the examiner), based on the display state (for example, the state of the button 3420) a state whereby execution of image quality improving processing is to be performed may be stored. By this means, in a case in which whether or not to execute image quality improving processing in imaging data units (examination units) has not been specified, processing can be performed based on information specified with respect to the entire database, while in a case where execution of image quality improving processing in imaging data units (examination units) has been specified, processing can executed individually based on the information in question.

Although an example has been illustrated in which images Im3407 and Im3408 are displayed as OCTA en-face images in the present embodiment, it is possible to change an OCTA en-face image to be displayed in accordance with a specification of the examiner. Therefore, a description will now be given regarding changing an image when execution of image quality improving processing has been specified (the button 3420 is in an active state).

Changing of an image is performed using a user interface (not illustrated) (for example, a combo box). For example, when the examiner changes the kind of image from a surface layer image to a choroidal vascular network image, the image quality improving unit 404 executes image quality improving processing for the choroidal vascular network image, and the outputting unit 405 displays a high quality image which the image quality improving unit 404 generated on the report screen. In other words, in response to an instruction from the examiner, the outputting unit 405 may change the display of a high quality image of a first depth range to the display of a high quality image of a second depth range that is at least partially different from the first depth range. At this time, by first depth range being changed to the second depth range in response to an instruction from the examiner, the outputting unit 405 may change the display of a high quality image of the first depth range to the display of a high quality image of the second depth range. Note that, in a case where, as described above, high quality images have already been generated with respect to images for which the possibility of being displayed upon transitioning to the report screen is high, the outputting unit 405 may display a high quality image which has already been generated. Note that, a method for changing the kind of image is not limited to the method described above, and it is also possible to generate OCTA en-face images for which different depth ranges are set by changing the layer that serves as a reference and an offset value. In this case, when the layer that serves as a reference or an offset value is changed, the image quality improving unit 404 executes image quality improving processing with respect to an arbitrary OCTA en-face image, and the outputting unit 405 displays a high quality image on the report screen. Changing of a layer that serves as a reference or an offset value can be performed using a user interface (not illustrated) (for example, a combo box or text box). Further, a range for generating an OCTA en-face image can be changed by dragging either of the boundary lines 3413 and 3414 (moving the layer boundary) displayed in a superimposed manner on the tomographic images Im3411 and Im3412. In a case where a boundary line is changed by dragging, an execution command with respect to image quality improving processing is continuously issued. Therefore, the image quality improving unit 404 may always perform processing with respect to the execution command, or may be configured to execute processing after the layer boundary is changed by dragging. Alternatively, although execution of image quality improving processing is continuously issued, the image quality improving unit 404 may be configured to cancel the previous command at the time point at which the next command arrives, and execute the most recent command. Note that, image quality improving processing takes a relatively long time in some cases. Consequently, even when the command is executed at any of the timings described above, it may take a relatively long time until a high quality image is displayed. Therefore, during a period from when a depth range for generating an OCTA en-face image is set in response to an instruction from the examiner until a high quality image is displayed, an OCTA en-face image (low quality image) corresponding to the set depth range may be displayed. In other words, a configuration may be adopted so that when the aforementioned depth range is set, an OCTA en-face image (low quality image) corresponding to the set depth range is displayed, and when the image quality improving processing is completed, the display of the relevant OCTA en-face image (the low quality image) is changed to a display of the high quality image. Further, information indicating that image quality improving processing is being executed may be displayed during the period from when the aforementioned depth range is set until the high quality image is displayed. Note that, the foregoing can be applied not only to a case where it is assumed that the state is one in which execution of image quality improving processing has already been specified (the button 3420 is in an active state), and can also be applied, for example, with respect to a period until a high quality image is displayed when execution of image quality improving processing was instructed in accordance with an instruction from the examiner.

Although in the present embodiment an example was illustrated in which different layers are displayed as the images Im3407 and Im3408 as OCTA en-face images, and a low quality image and a high quality image are displayed by switching therebetween, the present invention is not limited thereto. For example, a low-quality OCTA en-face image as the image Im3407 and a high-quality OCTA en-face image as the image Im3408 may be displayed side by side. In the case of displaying the images by switching therebetween, since images are switched at the same place it is easy to make a comparison of portions at which there is a change, while in the case of displaying images side by side, it is easy to compare the entire images since the images can be displayed at the same time.

Figure 38:
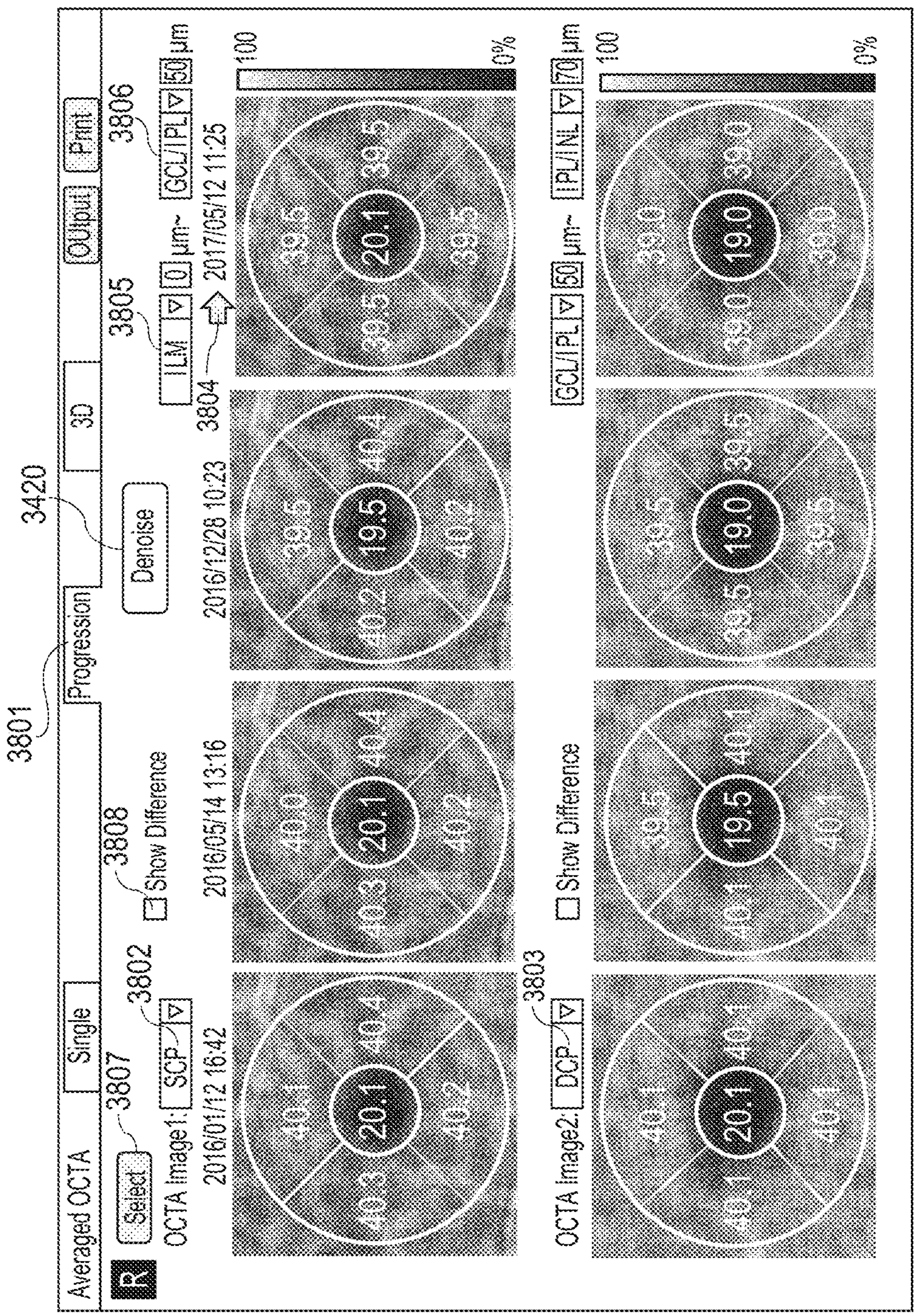
FIG. 38 is a view illustrating an example of the user interface according to the twenty-fourth embodiment.

Next, FIG. 34A and FIG. 34B will be used to describe execution of image quality improving processing in the case of screen transition. FIG. 34B is an example of a screen on which the OCTA en-face image Im3407 illustrated in FIG. 34A is displayed in an enlarged manner. In FIG. 34B also, similarly to FIG. 34A, the button 3420 is displayed. A screen transition from the screen illustrated in FIG. 34A to the screen illustrated in FIG. 34B is specified, for example, by double clicking on the OCTA en-face image Im3407, and a screen transition from the screen illustrated in FIG. 34B to the screen illustrated in FIG. 34A is specified by clicking on a "Close" button 3430. Note that, with regard to screen transition, a method for transitioning from one screen to another is not limited to the method described here, and a user interface (not illustrated) may also be used. In a case where execution of image quality improving processing has been specified (the button 3420 is active) at the time of screen transition, that state is also maintained when the screen transition occurs. In other words, in a case where the screen illustrated in FIG. 34B is transitioned to in a state in which a high quality image is displayed on the screen illustrated in FIG. 34A, the high quality image is also displayed on the screen illustrated in FIG. 34B. Further, the button 3420 is placed in an active state. The same applies in the case of transitioning from the screen illustrated in FIG. 34B to the screen illustrated in FIG. 34A. On the screen illustrated in FIG. 34B, the display can also be switched to a low quality image by specifying the button 3420. With regard to the screen transitions, the screen transitions are not limited to the screens described here, and as long as the transition is to a screen displaying the same imaging data, such as a display screen for follow-up observation or a display screen for a panorama image, transition is performed while maintaining the display state of the high quality image. In other words, on the display screen after transition, an image is displayed that corresponds to the state of the button 3420 on the display screen before transition. For example, if the button 3420 is in an active state on the display screen before transition, a high quality image is displayed on the display screen after transition. Further, for example, if the active state of the button 3420 is released on the display screen before transition, a low quality image is displayed on the display screen after transition. Note that, a configuration may be adopted so that, if the button 3420 is in an active state on the display screen for follow-up observation, a plurality of images obtained at different dates and times (different examination days) that are displayed side by side on the display screen for follow-up observation are switched to high quality images. In other words, a configuration may be adopted so that, if the button 3420 is in an active state on the display screen for follow-up observation, switching to high quality images is collectively performed with respect to a plurality of images obtained at different dates and times. An example of a display screen for follow-up observation is illustrated in FIG. 38. Upon a tab 3801 being selected in response to an instruction from the examiner, a display screen for follow-up observation as illustrated in FIG. 38 is displayed. At this time, the depth range of an en-face image can be changed by the examiner performing an operation to select from a predefined depth range set (3802 and 3803) displayed in list boxes. For example, superficial capillary is selected in the list box 3802, and deep capillary is selected in the list box 3803. Analysis results for en-face images of the superficial capillary are displayed in a display region on the upper side, and analysis results for en-face images of the deep capillary are displayed in a display region on the lower side. In other words, when a depth range is selected, a plurality of images obtained at different dates and times are collectively changed to a parallel display of analysis results for a plurality of en-face images in the selected depth range. At this time, if the display of analysis results is placed in a non-selected state, the display may be collectively changed to a parallel display of analysis results of a plurality of en-face images obtained at different dates and times. Further, if the button 3420 is specified in accordance with an instruction from the examiner, the display of a plurality of en-face images is collectively changed to the display of a plurality of high quality images. Further, in a case where the display of analysis results is in a selected state, if the button 3420 is specified in accordance with an instruction from the examiner, the display of analysis results for a plurality of en-face images is collectively changed to the display of analysis results for a plurality of high quality images. Here, the display of analysis results may be performed such that the analysis results are displayed in a superimposed manner on the images with any degree of transparency. At this time, changing to the display of analysis results may be, for example, a change to a state in which the analysis results are superimposed with any degree of transparency on the images that are being displayed. Further, changing to the display of analysis results may be, for example, a change to the display of respective analysis results and images (for example, two-dimensional maps) obtained by subjecting the respective analysis results and images to blending processing with any degree of transparency. Further, the kind of layer boundary and the offset position used to specify a depth range can each be collectively changed from user interfaces such as denoted by reference numerals 3805 and 3806. Note that, the depth ranges of a plurality of en-face images obtained at different dates and times may be collectively changed by also causing tomographic images to be displayed together therewith, and moving layer boundary data superimposed on the tomographic images, in accordance with an instruction from the examiner. At such time, a plurality of tomographic images obtained at different dates and times may be displayed side by side, and when the aforementioned movement is performed on one tomographic image, the layer boundary data may be similarly moved on the other tomographic images. Further, the image projection method and whether or not the projection artifact removal processing is to be performed can be changed, for example, by a selection from a user interface such as a context menu. Further, a selection button 3807 may be selected to display a selection screen, and an image selected from an image list displayed on the selection screen may be displayed. Note that, an arrow 3804 displayed at the upper part of the screen illustrated in FIG. 38 is a mark that indicates the currently selected examination, and the reference examination (baseline) is the examination (leftmost image in FIG. 38) selected at the time of follow-up imaging. Naturally, a mark indicating the reference examination may be displayed on the display unit. Further, in a case where a "Show Difference" check box 3808 is specified, a measurement value distribution (map or sector map) with respect to the reference image is displayed on the reference image. In addition, in this case, in a region corresponding to an examination date other than the examination date of the reference image, a differential measurement value map is displayed that shows differences between the measurement value distribution calculated for the reference image and the measurement value distribution calculated for an image in which the relevant region is displayed. As a measurement result, a trend graph (a graph of measurement values with respect to images for the respective examination dates that is obtained by measuring changes over time) may be displayed on the report screen. In other words, time-series data (for example, a time-series graph) for a plurality of analysis results corresponding to a plurality of images obtained at different dates and times may be displayed. At such time, with regard to analysis results relating to dates and times other than the plurality of dates and times corresponding to the displayed plurality of images also, the analysis results may be displayed as time-series data in a state in which the analysis results can be distinguished (for example, the color of each point on a time-series graph differs according to whether or not the corresponding image is displayed) from the plurality of analysis results corresponding to the plurality of images that are being displayed. Further, a regression line (curve) of the trend graph and a corresponding mathematical expression may be displayed on the report screen.

Although a description relating to an OCTA en-face image has been given in the present embodiment, the present invention is not limited thereto. An image relating to processing for displaying an image, image quality improving, and image analysis and the like according to the present embodiment may be an intensity en-face image. In addition, the kind of image is not limited to an en-face image, and may be a different kind of image such as a tomographic image, an SLO image, a fundus image, or a fluorescence fundus image. In this case, a user interface for executing image quality improving processing may be a user interface for instructing the execution of image quality improving processing with respect to a plurality of images of different kinds, or may be a user interface for selecting any image from a plurality of images of different kinds and instructing the execution of image quality improving processing.

According to the foregoing configuration, the outputting unit 405 can display an image which the image quality improving unit 404 according to the present embodiment processed on the display unit 20. At such time, as described above, in the case of a state in which at least one condition is selected among a plurality of conditions relating to the display of high quality images, the display of analysis results, the depth range of a front image to be displayed and the like, even if the display screen is transitioned to another display screen, the selected state may be maintained. Further, as described above, in the case of a state in which at least one condition among a plurality of conditions is selected, even if another condition is changed to a selected state, the state in which the at least one condition is selected may be maintained. For example, in a case where a display of analysis results is in a selected state, in response to an instruction from the examiner (for example, when the button 3420 is specified), the outputting unit 405 may change a display of analysis results for a low quality image to a display of analysis results for a high quality image. Further, in a case where a display of analysis results is in a selected state, in response to an instruction from the examiner (for example, when specification of the button 3420 is released), the outputting unit 405 may change the display of analysis results for a high quality image to a display of analysis results for a low quality image. Furthermore, in a case where a display of a high quality image is in a non-selected state, in response to an instruction from the examiner (for example, when specification of a display of analysis results is released), the outputting unit 405 may change the display of analysis results for a low quality image to a display of a low quality image. In addition, in a case where a display of a high quality image is in a non-selected state, in response to an instruction from the examiner (for example, when the display of analysis results is specified) the outputting unit 405 may change the display of a low quality image to a display of analysis results for a low quality image. Further, in a case where a display of a high quality image is in a selected state, in response to an instruction from the examiner (for example, when specification of a display of analysis results is released), the outputting unit 405 may change the display of analysis results for a high quality image to a display of a high quality image. Further, in a case where a display of a high quality image is in a selected state, in response to an instruction from the examiner (for example, when the display of analysis results is specified), the outputting unit 405 may change the display of a high quality image to a display of analysis results for a high quality image. Furthermore, let us consider a case where the display of a high quality image is in a non-selected state and a display of a first kind of analysis results is in a selected state. In this case, in response to an instruction from the examiner (for example, when the display of a second kind of analysis results is specified), the outputting unit 405 may change the display of the first kind of analysis results for a low quality image to a display of the second kind of analysis results for a low quality image. Further, let us consider a case where the display of a high quality image is in a selected state and a display of a first kind of analysis results is in a selected state. In this case, in response to an instruction from the examiner (for example, when the display of a second kind of analysis results is specified), the outputting unit 405 may change the display of the first kind of analysis results for a high quality image to a display of the second kind of analysis results for a high quality image. Note that, a configuration may be adopted so that, on the display screen for follow-up observation, as described above, changing of these displays is collectively reflected with respect to a plurality of images obtained at different dates and times. Here, the display of analysis results may be performed such that the analysis results are displayed in a superimposed manner on the images with any degree of transparency. At such time, changing to the display of analysis results may be, for example, a change to a state in which the analysis results are superimposed with any degree of transparency on the images that are being displayed. Further, changing to the display of analysis results may be, for example, a change to the display of respective analysis results and images (for example, two-dimensional maps) obtained by subjecting the respective analysis results and images to blending processing with any degree of transparency.

Twenty-Fifth Embodiment

Figure 35:
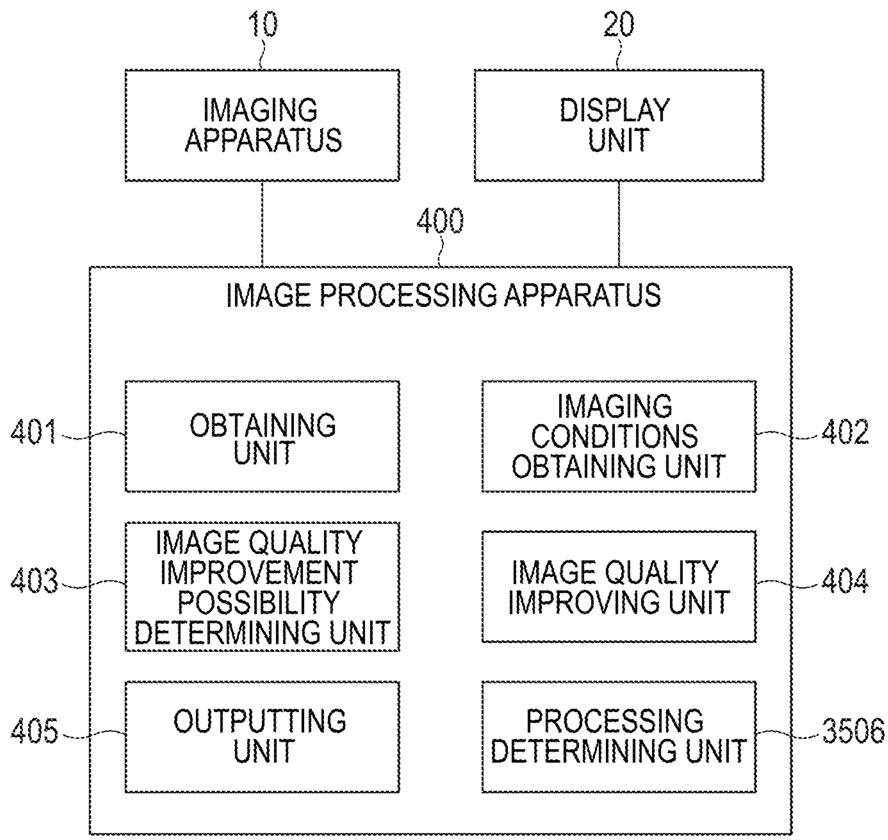
FIG. 35 is a view illustrating an example of a schematic configuration of an image processing apparatus according to a twenty-fifth embodiment.

Next, an image processing apparatus according to a twenty-fifth embodiment is described referring to FIG. 35. In the present embodiment, a processing determining unit 3506 will be described.

Unless explicitly stated otherwise, the configuration and processing of the image processing apparatus according to the present embodiment are the same as the configuration and processing of the image processing apparatus 400 according to the first embodiment. Therefore, hereunder, the processing determining unit 3506 according to the present embodiment will be described.

The processing determining unit 3506 determines whether image quality improving processing by the image quality improving unit 404 is to be performed by a GPU (graphics processing unit) or by the CPU.

The processing determining unit 3506 determines whether or not the environment with respect to a GPU installed in the apparatus for executing processing of the image quality improving unit 404, such as the GPU name, GPU driver and the memory size of the GPU, is an adequate environment for executing image quality improving processing using machine learning. If it is determined by the processing determining unit 3506 that the GPU is usable, the image quality improving unit 404 performs processing using the GPU. On the other hand, if it is determined by the processing determining unit 3506 that the GPU is unusable, the image quality improving unit 404 performs processing using the CPU. In a case where it is determined by the processing determining unit 3506 that the GPU is unusable, since the time taken for processing by the CPU is longer compared to the GPU, the outputting unit 405 displays information indicating that the processing is performed using the CPU and not the GPU on the display unit 20. Note that, in a case where the GPU is usable, information indicating that the processing is performed using the GPU may be displayed. With regard to the manner of displaying such information on the display unit 20, a message may be displayed or only a word such as GPU or CPU may be displayed. Note that, in a case where processing of the image quality improving unit 404 will take a long time (for example, from several tens of seconds to several minutes or more) because the CPU will be used to perform the processing, for example, a configuration may be adopted in which the button 3420 illustrated in FIG. 34A and FIG. 34B is not displayed, to thereby to disable execution of the image quality improving processing. By not displaying the user interface for executing image quality improving processing, the function thereof cannot be used. In a case where use of the function is disabled, information indicating that the function cannot be used may be displayed on the display unit 20.

The processing determining unit 3506 is not limited to only making determination regarding the GPU and CPU, and can also make determination with respect to execution of the image quality improving processing itself. For example, a case will be described in which license registration is required in order to execute image quality improving processing. The processing determining unit 3506 makes determination as to whether or not license registration has been performed, and if license registration has been performed, the processing determining unit 3506 enables execution of image quality improving processing by, for example, displaying the button 3420 illustrated in FIG. 34A and FIG. 34B. If license registration has not been performed, the button 3420 illustrated in FIG. 34A and FIG. 34B is not displayed, so that the function of the button 3420 cannot be used. Note that, in a case where license registration is required in order to execute image quality improving processing, determination as to whether or not license registration has been performed is made prior to the aforementioned determination regarding GPU processing and CPU processing.

The processing determining unit 3506 may be configured to not only automatically perform determination regarding execution of processing, but to also perform determination based on an instruction of the examiner. For example, in a case where the examiner uses a user interface (not illustrated) to specify that processing be executed by the CPU, the processing determining unit 3506 determines that the CPU, and not the GPU, is to be used for processing. In this case, it is not necessary for the processing determining unit 3506 to evaluate the GPU installed in the apparatus, and the image quality improving unit 404 performs the processing using the CPU.

The processing of the processing determining unit 3506 described above need not be executed every time processing of the image quality improving unit 404 is performed, and it suffices to perform the processing of the processing determining unit 3506 when the image processing apparatus is started up. Alternatively, the processing determining unit 3506 may make determination periodically (for example, once a day).

By this configuration, the processing determining unit 3506 according to the present embodiment determines whether or not image quality improving processing can be executed. Further, it is possible to select the appropriate environment and execute processing for machine learning.

Modification 1

In the various embodiments described above, a configuration may be adopted so as to enhance the efficiency and accuracy of an image quality improving engine and an authenticity evaluating engine by performing training in a manner such that the machine learning model of the image quality improving engine and the machine learning model of the authenticity evaluating engine contest with each other. In this case, a generative adversarial network (GAN) is an example of a network in which training is performed in a manner such that a plurality of models contest with each other. At such time, the machine learning model of the image quality improving engine corresponds to a generator model (generator) for generating an image. Further, the machine learning model of the authenticity evaluating engine corresponds to a discriminator model (discriminator) for discriminating whether or not a generated image is genuine. For example, the machine learning model of the image quality improving engine is trained so that the real label is output when an image which is the correct answer of image quality improving is evaluated by the authenticity evaluating engine. Further, the machine learning model of the authenticity evaluating engine is trained so as to output the fake label when an image that the image quality improving engine generates is evaluated by the authenticity evaluating engine. Accordingly, training is repeated so that an image which the image quality improving engine generates and an image which is the correct answer of image quality improving become indistinguishable from each other. As a result, the efficiency and accuracy of the image quality improving engine and the authenticity evaluating engine are enhanced.

Note that, the image quality improving engine may be a learned model obtained by learning using training data including at least one image generated by a generative adversarial network. At such time, a configuration may be adopted that enables the examiner to input an instruction for selecting whether or not at least one image generated by the generative adversarial network is used as training data for learning.

Modification 2

In the various embodiments and modifications described above, a high quality image which an image quality improving engine generated and an input image may be combined and output. For example, in a case where the pixel values of an input image are low (dark as an image) or the like, a situation in which the image quality improving engine reduces a pixel value as a noise component is conceivable. Therefore, a configuration may be adopted so as to change a ratio for combining an image which the image quality improving engine generated and an input image based on the brightness of the input image, and output the resultant composite image. In other words, the outputting unit 405 (display controlling unit) may output a composite image obtained by combining an input image (first image) and a high quality image (second image) according to a ratio obtained using information relating to at least a partial region of the input image. At such time, the ratio for combining the two images may be determined by using pixel values (brightness of at least a partial region) in at least a partial region of the input image as the aforementioned information. At such time, for example, the lower (darker) that pixel values in the input image are, the higher that the ratio of combining the input image with respect to the high quality image is set to. Further, for example, the higher (brighter) that pixel values in the input image are, the lower that the ratio of combining the input image with respect to the high quality image is set to. Specifically, the ratio for combining the images is changed based on a statistical value (average value, median value, mode value, minimum value, maximum value, variance, standard deviation, or the like) with respect to the pixel values of the entire image. For example, in a case where the statistical value with respect to the pixel values of the input image is lower than a first threshold value, a composite image obtained by combining the image which the image quality improving engine generated and the input image at a ratio of 0.5:0.5 (average of the two images) is output. Alternatively, in a case where the statistical value with respect to the pixel values of the input image is higher than a second threshold value, a composite image obtained by combining the image which the image quality improving engine generated and the input image at a ratio of 0.9:0.1 (weighted average of the two images) is output. Note that, it is assumed that the combining ratios between the first threshold value and the second threshold value change smoothly. A statistical value calculated based on the input image may be determined with respect to the entire image, or a configuration may be adopted in which the input image is divided into a number of regions and local statistical values are determined. In the case of dividing the image into a number of regions, the ratio values may be corrected to be smooth values so that the ratios at which the images are combined do not change sharply between adjacent regions. In addition, instead of dividing the image into regions, by gradating the image using a smoothing filter such as a Gaussian filter, a combining ratio may be determined for each pixel by comparing values with the first and second threshold values in pixel units. Note that, an image to be used for calculating a statistical value for the pixel values is not limited to the input image. For example, when the input image is an OCTA image, the statistical value for the pixel values may be calculated using an intensity en-face image or a projection image.

In addition, instead of using a statistical value for pixel values of the input image, a configuration may be adopted so as to change the ratio for combining the two images according to a difference between the input image and the high quality image which the image quality improving engine generated. In other words, a ratio for combining two images may be determined by using a differential value between pixel values in at least corresponding partial regions of the two images as the aforementioned information. Specifically, a configuration may be adopted so as to increase the ratio of the input image in a case where there is a large difference between the input image and the high quality image. In other words, in a case where denoising was performed excessively in the high quality image, a natural high quality image is generated by increasing the ratio of the input image and combining the images. Note that, when determining the differential value, a determination may be made based on not only simple difference information, but also on structural difference information. For example, a configuration may be adopted so as to extract only linear structures using a filter such as a Hessian filter. As a result, random noise is not detected as a difference, and only noise having a certain degree of continuity such as a blood vessel can be extracted. Further, a configuration may be adopted so as to simply subject noise components to labelling processing to extract only noise having a certain size or more. In a case where the ratio for combining the images is changed depending on a difference, similarly to when using a statistical value, the difference may be determined with respect to the entire image, or a configuration may be adopted in which the image is divided into a number of regions and local differential values are determined.

In addition, the combining ratio may be determined after a site or an image is recognized. In this regard, for example, the case of an OCTA image of a surface layer will be described. In an OCTA image of a surface layer, because a blood vessel is not present in an FAZ (foveal avascular zone), the FAZ may be dark in the OCTA image. Therefore, with regard to an FAZ, it is conceivable to increase the ratio of the high quality image with respect to the input image. In other words, the ratio of the image in which noise is reduced more is increased. On the other hand, if there is a dark region at a position other than the position of a FAZ, it is difficult to determine whether the region in question is an avascular zone (NPA: nonperfusion area), or the region is a region in which a blood vessel is actually present but for which the brightness decreased due to a shadow or the like. Thus, it is conceivable to lower the ratio of the high quality image with respect to the input image. In other words, the ratio of the image with respect to which there is a possibility that a region of low intensity which originally existed disappeared from the image is lowered. Thus, the combining ratio may be changed based on a result of recognizing a site, and not only based on the brightness of an image or a differential change. Next, a case of recognizing an image will be described. In the case of an OCTA image, the appearance and brightness of the image vary depending on the depth between a surface layer, a deep layer and an outer layer. Therefore, the kind of layer which the target image is may be recognized, and the ratio may be changed according to the kind of layer. Recognition of an image may be performed using information regarding the position of boundary lines when generating layers, or layers may be automatically recognized from the image. In other words, the combining ratio may be changed according to which depth the OCTA image was generated from, and not by only determining the brightness of the image. For example, an OCTA image of the surface layer is bright overall, while an OCTA image of the outer layer is dark overall. Therefore, first and second threshold values of a combining ratio according to a statistical value of pixel values and the ratios corresponding thereto may be set as respectively different values with regard to an OCTA image of the surface layer and an OCTA image of the outer layer. For example, a configuration may be adopted so that the image which the image quality improving engine generated and the input image are combined at a ratio of 0.5:0.5 if the statistical value is lower than the first threshold value for the surface layer, while the image which the image quality improving engine generated and the input image are combined at a ratio of 0.7:0.3 if the statistical value is lower than the first threshold value for the outer layer.

Note that, although in the above description of image combining, processing that combines the pixel values themselves is described, a configuration may be adopted that changes the opacity of an image. In other words, the combining ratio may be an alpha blending value. Therefore, for example, a configuration may be adopted so that, in a case where the ratio of the input image is taken as 0.3, an image for which the alpha value of the image generated by the image quality improving engine was taken as 1 and the alpha value of the input image was taken as 0.3 is displayed. In this case, it is desirable to ensure that the image that the image quality improving engine generated is displayed without fail, and to change the alpha value of the input image to display the image semi-transparently.

Further, in the case of outputting an image obtained by combining an image that the image quality improving engine generated and an input image, a configuration may be adopted so as to output an image for which the image quality improving engine automatically determined the ratio as described above. A configuration may also be adopted that allows the ratio for combining two images to be changed in accordance with an instruction from the examiner using a user interface (not illustrated). At such time, as the user interface, a configuration may be adopted so that the ratio can be changed using a slider bar or by input of a numerical value to a text box or the like, or a configuration may be adopted that presents a plurality of images obtained by changing the combining ratio to the examiner and allows the examiner to select an image.

Further, a ratio for combining an input image and a high quality image may be determined based on information relating to at least a partial region of the input image using a learned model obtained by learning using training data in which a medical image is adopted as input data, and information relating to a ratio for combining the medical image and a high-quality medical image obtained by subjecting the medical image to image quality improving is adopted as correct answer data (ground truth). At such time, the information relating to the ratio may be, for example, a value of a ratio that is set (changed) in accordance with an instruction from the examiner. Further, the learned model, for example, may be obtained by learning using training data including input data in which a medical image and a high-quality medical image obtained by subjecting the medical image to image quality improving are taken as a set. At such time, the learned model can be obtained by machine learning using the aforementioned training data.

Here, for example, deep learning which is composed of a multi-level neural network is one kind of machine learning. Further, for example, a convolutional neural network (CNN) can be used for at least a part of a multi-level neural network. In addition, technology pertaining to auto-encoders may be used for at least a part of a multi-level neural network. Furthermore, technology pertaining to back-propagation (error back-propagation method) may be used for learning. However, the machine learning is not limited to deep learning, and any model may be used as long as the model is capable of, by itself, extracting (representing) a feature value of training data such as an image by learning. Further, the machine learning is also not limited to such a model, and may be implemented by learning using feature values obtained using a medical image in advance before learning as training data. For example, the machine learning may be Support Vector Machine, AdaBoost, Random Forest, a Bayesian network, or the like. In addition, the learned model may be updated by incremental learning in which the value of a ratio that was set (changed) in accordance with an instruction from the examiner is adopted as training data. For example, if the examiner tends to set the ratio of the input image to the high quality image high when the input image is relatively dark, the learned model performs incremental learning so as to have such a tendency. Thus, for example, the learned model can be customized as a learned model that can obtain a combining ratio that matches the preference of the examiner. At such time, a button for determining, in accordance with an instruction from the examiner, whether or not to use the set (changed) value of the ratio as training data for incremental learning may be displayed on the display screen. Further, a configuration may be adopted in which a ratio determined using the learned model is taken as a default value and, thereafter, it is possible to change the ratio value from the default value in accordance with an instruction from the examiner. Furthermore, the image quality improving engine may be a learned model obtained by incremental learning using training data including at least one high quality image generated by an image quality improving engine. At such time, a configuration may be adopted that enables a selection as to whether or not a high quality image is to be used as training data for incremental learning to be made by an instruction from the examiner.

Note that, a composite image output upon combining an image generated by an image quality improving engine and an input image described in the present modification can be output instead of a high quality image described in the various embodiments described above, and for example, the same applies with respect to a display screen for a follow-up observation or a panorama image or the like. In other words, a composite image according to the present modification may be obtained at a plurality of positions, and a wide-angle image may be generated using a plurality of composite images. Further, an obtained wide-angle image generated using a plurality of composite images may be displayed on a display screen for a panorama image. Furthermore, a composite image according to the present modification may be obtained at different dates and times, and a plurality of composite images may be displayed side by side on a display screen for follow-up observation. It is also possible to perform analytical processing such as blood vessel analysis processing on a composite image according to the present modification.

Modification 3

Analysis results such as the thickness of a desired layer or various blood vessel densities may be displayed on a report screen described in the various embodiments and modifications described above. Further, a parameter value (distribution) relating to a site of interest including at least one of the optic nerve head, the macular area, a vascular zone, a nerve fascicle, a vitreous region, a macular region, a choroid region, a sclera region, a lamina cribrosa region, a retinal layer boundary, a retinal layer boundary edge, a photoreceptor cell, a blood cell, a blood vessel wall, a blood vessel inner wall boundary, a blood vessel external boundary, a ganglion cell, a corneal region, a corner region, and Schlemm's canal and the like may be displayed as an analysis result. At such time, for example, an accurate analysis result can be displayed by analyzing a medical image subjected to various kinds of artifact removal processing. Note that, an artifact may be, for example, a false image region caused by light absorption by a vascular zone or the like, a projection artifact, or a band-like artifact in a front image that arises in the main scanning direction of the measurement light due to the state of the eye to be examined (movement or blinking or the like). Further, an artifact may be of any kind as long as it is an imaging failure region that, for example, randomly arises at each imaging on a medical image of a predetermined site of the subject. Further, the value (distribution) of a parameter relating to a region including at least one of the kind of artifacts (imaging failure regions) described above may be displayed as an analysis result. Furthermore, the value (distribution) of a parameter relating to a region including at least one abnormal site such as drusen, a neovascular site, leucoma (hard exudates), pseudodrusen or the like may be displayed as an analysis result. An analysis result may be displayed using an analysis map, or using sectors which indicate statistical values corresponding to respective divided regions or the like. Note that, an analysis result may be generated using a learned model (analysis result generating engine, or a learned model for generating analysis results) obtained by learning the analysis results of a medical image as training data. At such time, the learned model may be a model obtained by learning using training data including a medical image and an analysis result for the medical image, or training data including a medical image and an analysis result for a medical image of a different kind from the relevant medical image or the like. Further, a learned model may be a model obtained by learning using training data including input data in which a plurality of medical images of different kinds of a predetermined site, such as an intensity front image and a motion contrast front image, are taken as a set. Here, an intensity front image corresponds to an intensity en-face image, and a motion contrast front image corresponds to an OCTA en-face image. Further, a configuration may be adopted so as to display an analysis result obtained using a high quality image generated by an image quality improving engine. In addition, input data included in the training data may be a high quality image generated by an image quality improving engine, or may be a set composed of a low quality image and a high quality image. Further, the training data may be, for example, data obtained by labeling input data for which information including at least one kind of information among an analysis value (for example, an average value or a median value) obtained by analyzing an analysis region, a table including analysis values, an analysis map, and a position of an analysis region such as a sector in an image or the like, is adopted as correct answer data (of supervised learning). Note that, a configuration may be adopted so that an analysis result obtained by a learned model for analysis result generation is displayed in response to an instruction from the examiner.

Further, various kinds of diagnosis results such as results relating to glaucoma or age-related macular degeneration may be displayed on a report screen in the various embodiments and modifications described above. At such time, for example, an accurate diagnosis result can be displayed by analyzing a medical image subjected to various kinds of artifact removal processing as described above. Further, in the diagnosis result, the position of a specified abnormal site may be displayed on the image, and the state of an abnormal site or the like may be displayed using characters or the like. Further, a classification result (for example, Curtin's classification) for an abnormal site may be displayed as a diagnosis result. Note that, a diagnosis result may be a result generated using a learned model (diagnosis result generating engine, or a learned model for generating diagnosis results) obtained by learning using diagnosis results for medical images as training data. At such time, the learned model may be a model obtained by learning using training data including a medical image and a diagnosis result for the medical image, or training data including a medical image and a diagnosis result for a medical image of a different kind from the relevant medical image or the like. Further, a configuration may be adopted so as to display a diagnosis result obtained using a high quality image generated by an image quality improving engine. In addition, input data included in the training data may be a high quality image generated by an image quality improving engine, or may be a set composed of a low quality image and a high quality image. Further, the training data may be, for example, data obtained by labeling input data for which information including at least one kind of information among the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information) is adopted as correct answer data (of supervised learning). Note that, a configuration may be adopted so that a diagnosis result obtained by a learned model for diagnosis result generation is displayed in response to an instruction from the examiner.

Further, an object recognition result (object detection result) or a segmentation result with respect to a site of interest, an artifact, an abnormal site or the like as described above may be displayed on a report screen in the various embodiments and modifications described above. At such time, for example, a rectangular frame or the like may be superimposed around an object on the image and displayed. Further, for example, a color or the like may be superimposed on an object on the image and displayed. Note that, an object recognition result or a segmentation result may be a result generated using a learned model obtained by learning using training data in which information that indicates object recognition or segmentation is labeled on a medical image as correct answer data. Note that, the aforementioned analysis result generation or diagnosis result generation may be realized by utilizing the aforementioned object recognition result or segmentation result. For example, processing for generating an analysis result or for generating a diagnosis result may be performed with respect to a site of interest obtained by object recognition processing or segmentation processing.

The learned model described above may be a learned model obtained by learning using training data including input data in which a plurality of medical images of different kinds that are images of a predetermined site of a subject are taken as a set. At such time, for example, data in which a motion contrast front image of the fundus and an intensity front image (or intensity tomographic image) are taken as a set is conceivable as input data included in the training data. Further, for example, data in which a tomographic image (B-scan image) of the fundus and a color fundus image (or fluorescence fundus image) are taken as a set is conceivable as input data included in the training data. In addition, the plurality of medical images of different kinds may be of any kind as long as the medical images were obtained by different modalities, different optical systems, or different principles or the like. Further, the learned model described above may be a learned model obtained by learning using training data including input data in which a plurality of medical images of different sites of a subject are taken as a set. At such time, for example, data in which a tomographic image (B-scan image) of the fundus and a tomographic image (B-scan image) of the anterior ocular segment are taken as a set is conceivable as input data included in the training data. Further, for example, data in which a three-dimensional OCT image (three-dimensional tomographic image) of the macula of the fundus and a tomographic image obtained by circular scanning (or raster scanning) of the optic nerve head of the fundus are taken as a set is also conceivable as input data included in the training data. Note that, the input data included in the training data may be a plurality of medical images of different sites of the subject and of different kinds. At such time, for example, input data in which a tomographic image of the anterior ocular segment and a color fundus image are taken as a set is conceivable as input data included in the training data. Further, the learned model described above may be a learned model obtained by learning using training data including input data in which a plurality of medical images of different imaging angles of view that are images of a predetermined site of the subject are taken as a set. Further, input data included in the training data may be data obtained by joining together a plurality of medical images obtained by time-dividing a predetermined site into multiple regions, such as in the case of a panorama image. At such time, by using a wide-angle image such as a panorama image as training data, the result of each processing can be enhanced since there is a possibility that a feature value of the image can be acquired with good accuracy for reasons such as the fact that the amount of information is greater than in the case of a narrow-angle image. Further, input data included in the training data may be input data in which a plurality of medical images obtained at different dates and times of a predetermined site of the subject are taken as a set.

Further, a display screen on which at least one result among an analysis result, a diagnosis result, an object recognition result and a segmentation result described above is to be displayed is not limited to the report screen. Such a display screen may be, for example, at least one display screen among an imaging confirmation screen, a display screen for follow-up observation, and a preview screen for performing various kinds of adjustments before imaging (a display screen on which various kinds of live moving images are displayed) and the like. For example, by causing the aforementioned at least one result obtained using a learned model described above to be displayed on the imaging confirmation screen, the examiner can check an accurate result even immediately after imaging. Further, changing the display between a low quality image and a high quality image described above may be, for example, changing the display between an analysis result for a low quality image and an analysis result for a high quality image.

Modification 4

A configuration may be adopted so that, on a preview screen in the various embodiments and modifications described above, a learned model described above is used for every at least one frame of a live moving image. At such time, a configuration may be adopted so that, in a case where a plurality of live moving images of different sites or different kinds are displayed on the preview screen, learned models that correspond to the respective live moving images are used. By this means, for example, since the processing time can be shortened even for a live moving image, the examiner can obtain highly accuracy information prior to the start of imaging. Therefore, for example, since failures of re-imaging and the like can be reduced, the accuracy and efficiency of diagnosis can be improved. Note that, the plurality of live moving images may include at least one kind of moving image among, for example, a moving image of the anterior ocular segment for alignment in the XYZ-directions, a front moving image of the fundus for focus adjustment or OCT focus adjustment of a fundus observation optical system, and a tomographic moving image of the fundus for coherence gate adjustment in OCT (adjustment of the optical path length difference between the measurement optical path length and the reference optical path length).

Furthermore, a moving image to which a learned model described above can be applied is not limited to a live moving image, and for example the moving image may be a moving image stored (saved) in a storage unit. At such time, for example, a moving image obtained by performing alignment with respect to every at least one frame of a tomographic moving image of the fundus stored (saved) in a storage unit may be displayed on the display screen. For example, in a case where it is desired to suitably observe the vitreous body, first, a reference frame based on conditions such as that the vitreous body is present as much as possible in the frame may be selected. At such time, each frame is a tomographic image (B-scan image) in the X-Z direction. Subsequently, a moving image in which other frames have been aligned in the X-Z direction with respect to the selected reference frame may be displayed on the display screen. At such time, for example, a configuration may be adopted so as to cause high quality images (high image quality frames) sequentially generated by the image quality improving engine for every at least one frame of the moving image to be consecutively displayed. In this case there is a possibility that, during various kinds of adjustment, the imaging target such as the retina of the eye to be examined could not yet be successfully imaged. Thus, since there is a large difference between the medical image input to the learned model and the medical image used as training data, there is a possibility that a high quality image was not accurately obtained. Therefore, a configuration may be adopted so that when an evaluation value such as a value obtained when the image quality of a tomographic image (B scan) is evaluated exceeds a threshold value, display of a high-quality moving image (consecutive display of high image quality frames) is automatically started. Further, a configuration may be adopted so that when an evaluation value such as a value obtained when the image quality of a tomographic image (B scan) is evaluated exceeds a threshold value, the image quality improving button is changed to a state (active state) in which the button can be selected by the examiner. Further, a configuration may be adopted in which different image quality improving engines are prepared for each imaging mode for which scanning patterns or the like are different, and an image quality improving engine that corresponds to a selected imaging mode is selected. Further, one image quality improving engine obtained by learning using training data including various medical images obtained in different imaging modes may be used. Note that, as methods for performing alignment among frames described above, the same method may be applied with respect to the method for performing alignment in the X-direction and the method for performing alignment in the Z-direction (depth direction), or the methods that are applied may all be different. In addition, alignment in the same direction may be performed a plurality of times by different methods. For example, a coarse alignment may be performed, and thereafter a precise alignment may be performed. Further, the methods for alignment include, for example, (coarse Z-direction) alignment using a retinal layer boundary obtained by subjecting a tomographic image (B-scan image) to segmentation processing, (precise X-direction or Z-direction) alignment using correlation information (similarity) between a plurality of regions obtained by dividing a tomographic image and a reference image, (X-direction) alignment using a one-dimensional projection image generated for each tomographic image (B scan image), and (X-direction) alignment using a two-dimensional front image. Further, a configuration may be adopted so as to perform precise alignment in sub-pixel units after coarse alignment was performed in pixel units.

Modification 5

In the various embodiments and modifications described above, in a case where a learned model is undergoing incremental learning, there is a possibility that it will be difficult to output (infer/predict) using the learned model which is undergoing incremental learning itself. Therefore, input of a medical image to a learned model which is undergoing incremental learning may be prohibited. Further, a learned model that is the same as a learned model which is undergoing incremental learning may be prepared as another auxiliary learned model. At such time, a configuration may be adopted so that input of a medical image to the auxiliary learned model can be executed which incremental learning is being performed. Subsequently, after the incremental learning is completed, the learned model which underwent the additional learning is evaluated, and if there is no problem, it suffices to switch from the auxiliary learned model to the learned model which underwent the additional learning. Further, a configuration may be adopted so that the auxiliary learned model is used if there is a problem.

Further, a configuration may be adopted so that learned models obtained by learning for respective imaged sites can be selectively utilized. Specifically, a plurality of learned models can be prepared that include a first learned model obtained using training data including a first imaged site (lung, eye to be examined, or the like), and a second learned model obtained using training data including a second imaged site that is different from the first imaged site. Further, a configuration may be adopted so as to select any one of this plurality of learned models. At such time, the configuration may have a control unit configured to, in response to an instruction from the examiner, retrieve (for example, through a network from a server or the like of an external facility such as a hospital or a laboratory) data in which an imaged site (site specified by header information or manually input by the examiner) corresponding to a selected learned model and an image obtained by imaging the relevant imaged site form a pair, and execute learning in which the retrieved and obtained data is adopted as training data as incremental learning with respect to the selected learned model. By this means, incremental learning can be efficiently performed for each imaged site by using an image obtained by imaging an imaged site that corresponds to the learned model.

Further, when obtaining training data for incremental learning through a network from a server or the like of an external facility such as a hospital or a laboratory, it is desired to reduce a decrease in reliability due to falsification or system trouble during incremental learning or the like. Therefore, the correctness of the training data for incremental learning may be detected by confirming the consistency by a digital signature or hashing. By this means the training data for incremental learning can be protected. At such time, in a case where the correctness of the training data for incremental learning could not be detected as the result of confirming the consistency by a digital signature or hashing, a warning to that fact is given and incremental learning is not performed using the training data in question. Note that, the server may be any form of server, such as a cloud server, a FOG server, or an edge server, regardless of the installation location thereof.

Modification 6

In the various embodiments and modifications described above, an instruction from the examiner may be a voice instruction or the like in addition to a manual instruction (for example, an instruction using a user interface or the like). At such time, for example, a machine learning engine including a speech recognition engine (a speech recognition model or a learned model for speech recognition) obtained by machine learning may be used. In addition, a manual instruction may be an instruction by character input using a keyboard, a touch panel, or the like. At such time, for example, a machine learning engine including a character recognition engine (a character recognition model, a learned model for character recognition) obtained by machine learning may be used. Further, an instruction from the examiner may be an instruction by a gesture or the like. At such time, a machine learning engine including a gesture recognition engine (a gesture recognition model, a learned model for gesture recognition) obtained by machine learning may be used. Further, an instruction from the examiner may be a result of detection of the line of sight of the examiner on a monitor or the like. The line-of-sight detection result may be, for example, a pupil detection result using a moving image of the examiner obtained by imaging from around the monitor. At such time, the pupil detection from the moving image may use an object recognition engine as described above. Further, an instruction from the examiner may be an instruction by brain waves, or a faint electric signal flowing through the body or the like. In such a case, for example, the training data may be training data in which character data or voice data (waveform data) or the like indicating an instruction to display a result obtained by processing of various learned models as described above is adopted as input data, and an execution command for actually causing a result obtained by processing of various learned models to be actually displayed on a display unit is adopted as correct answer data. Further, the training data may be training data in which, for example, character data or voice data or the like indicating an instruction to display a high quality image obtained with a learned model for improving image quality is adopted as input data, and an execution command for displaying a high quality image and an execution command for changing the button 3420 to an active state are adopted as correct answer data. Naturally, any kind of training data may be used as long as, for example, the instruction content indicated by the character data or voice data or the like and the execution command content correspond with each other. Further, voice data may be converted to character data using an acoustic model or a language model or the like. Further, processing that reduces noise data superimposed on voice data may be performed using waveform data obtained with a plurality of microphones. Further, a configuration may be adopted so that a selection between an instruction issued by characters or voice or the like and an instruction input using a mouse or a touch panel or the like can be made according to an instruction from the examiner. In addition, a configuration may be adopted so that a selection can be made to turn instruction by characters or voice or the like on or off according to an instruction from the examiner.

Figure 36A:
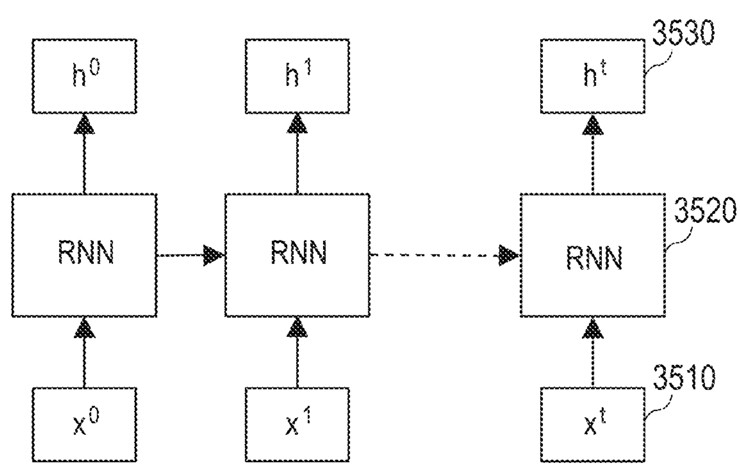
FIG. 36A is a view illustrating an example of a configuration of a neural network that is used as a machine learning engine according to Modification 6.
Figure 36B:
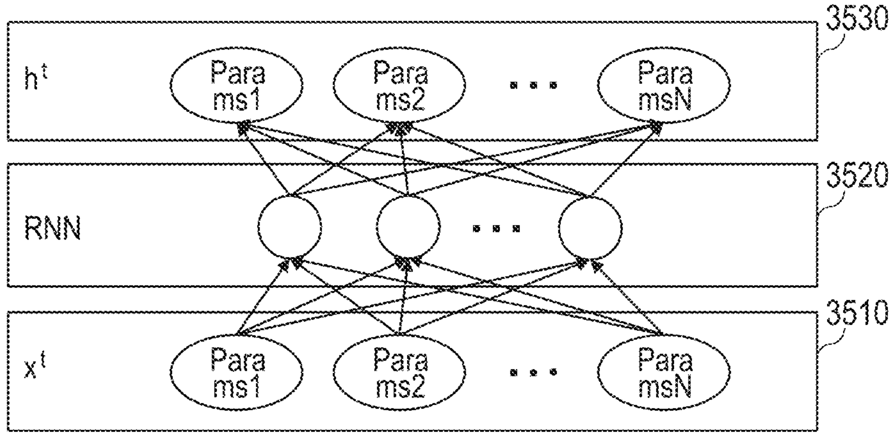
FIG. 36B is a view illustrating an example of the configuration of the neural network that is used as the machine learning engine according to Modification 6.
Figure 37A:
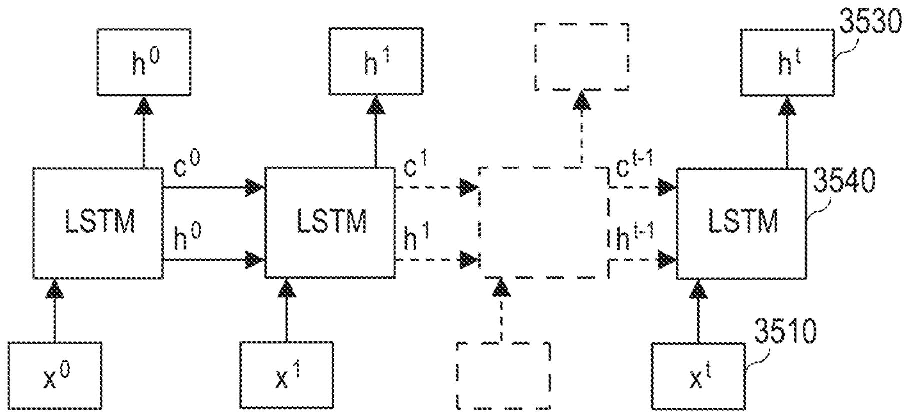
FIG. 37A is a view illustrating an example of the configuration of the neural network that is used as the machine learning engine according to Modification 6.
Figure 37B:
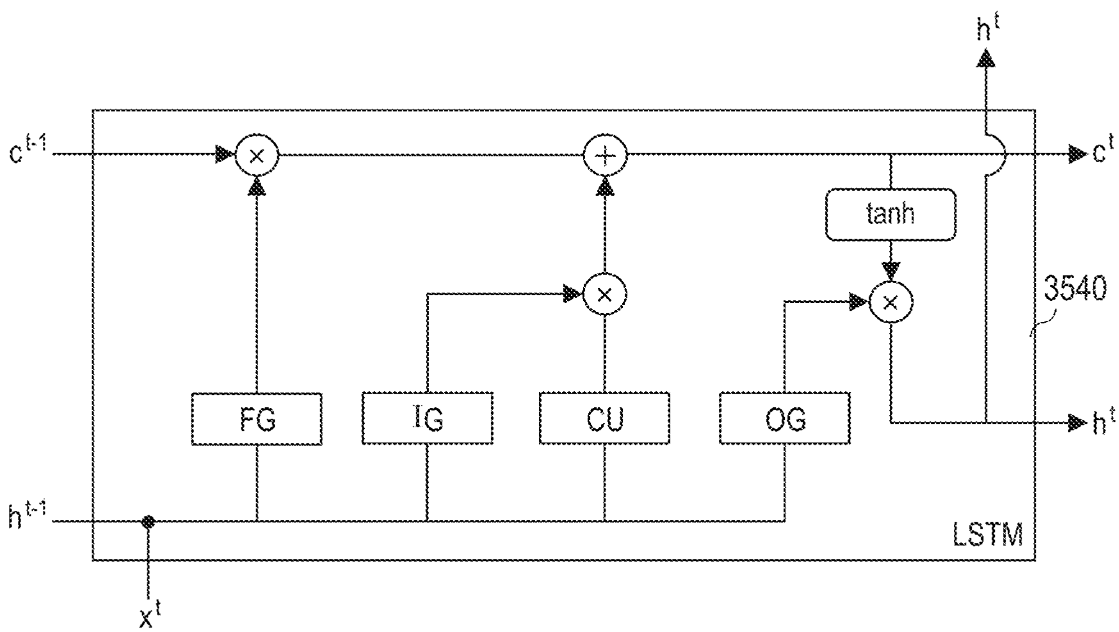
FIG. 37B is a view illustrating an example of a configuration of a neural network that is used as a machine learning engine according to Modification 7.

In this case, the machine learning includes deep learning as described above, and for example, a recurrent neural network (RNN) can be used as at least a part of the multi-layer neural network. Here, as an example of the machine learning engine according to the present modification, an RNN that is a neural network that handles time-series information will be described with reference to FIG. 36A and FIG. 36B. Further, a long short-term memory (hereinafter referred to as an "LSTM"), which is a kind of RNN, will be described with reference to FIG. 37A and FIG. 37B. FIG. 36A illustrates a structure of an RNN that is a machine learning engine. An RNN 3520 has a loop structure in the network, and inputs data $x^t$3510 at time t, and outputs data $h^t$3530. Since the RNN 3520 has a loop function in the network, the state at the current time can be taken over to the next state, and hence time-series information can be handled. FIG. 36B illustrates an example of the input/output of parameter vectors at time t. The data $x^t$3510 includes N pieces of data (Para ms1 to Para msN). Further, the data $h^t$3530 output by the RNN 3520 includes N pieces of data (Para ms1 to Para msN) corresponding to the input data. However, since the RNN cannot handle long-time information during back propagation, the LSTM may be used. The LSTM can learn long-term information by providing a forget gate, an input gate, and an output gate. FIG. 37A illustrates a structure of the LSTM. In an LSTM 3540, information that the network takes over at the next time t is an internal state $c^{t-1}$ of the network called a cell and output data $h^{t-1}$. Note that lowercase letters (c, h, x) in the figure represent vectors. Next, the LSTM 3540 is illustrated in detail in FIG. 37B. In FIG. 37B, reference characters FG denote a forget gate network, reference characters IG denote an input gate network, and reference characters OG denote an output gate network, and each of these networks is a sigmoid layer. Therefore, a vector in which each element has a value from 0 to 1 is output. The forget gate network FG determines how much past information is held, and the input gate network IG determines which value is to be updated. Reference characters CU denote a cell update candidate network, which is an activation function tan h layer. This creates a vector of new candidate values to be added to the cell. The output gate network OG selects an element of a cell candidate and selects how much information is to be transmitted at the next time. Note that, the LSTM model described above is a basic form, and the present invention is not limited to the network illustrated here. The coupling between networks may be changed. A QRNN (quasi-recurrent neural network) may be used instead of an LSTM. In addition, the machine learning engine is not limited to a neural network, and Boosting or Support Vector Machine or the like may be used. Further, in a case where an instruction from the examiner is input by characters or voice or the like, a technique relating to natural language processing (for example, Sequence to Sequence) may be applied. Further, a dialogue engine (a dialogue model or a learned model for dialogue) that responds to the examiner with an output such as text or voice may be applied.

Modification 7

The various embodiments and modifications described above include at least each of the elements described hereunder, and also include at least each of the various combinations described hereunder, within a range in which no technical contradiction arises. Note that, for example, various kinds of learning described above can be applied to the following machine learning. Further, at least an partial region described hereunder is, for example, the partial region described above, and is a rectangular region or the like.

First, the image quality improving engine may include a machine learning engine that performs machine learning for generating a two-dimensional high quality image using a two-dimensional medical image of a predetermined site of the subject. At such time, the image quality improving engine may be a learned model obtained by performing learning of training data including at least a partial region of a two-dimensional medical image. For example, the image quality improving engine may be a learned model obtained by performing learning of training data including at least a partial region of a first front image of a first depth range of an eye to be examined. Further, as another image quality improving engine, another learned model may be generated that is obtained by performing learning of training data including at least a partial region of a second front image of a second depth range of the eye to be examined that is a second depth range in which at least some of the range is different from the first depth range. In other words, in a case where a feature value of the second front image and a feature value of the first front image differ comparatively, not only the first learned model is generated, but the second learned model may also be generated. Thus, for example, a plurality of learned models can be selectively used in accordance with a plurality of medical images. Therefore, a plurality of medical images having feature values which differ comparatively from each other can be subjected to accurate image quality improving. Note that, in a case where these feature values are comparatively similar, the second learned model need not be generated, and it suffices to generate a common learned model obtained by learning using the first front image and the second front image as training data.

Further, the image quality improving engine may include a machine learning engine that performs machine learning for generating a three-dimensional high quality image using a three-dimensional medical image of a predetermined site of the subject. At such time, the image quality improving engine may be a learned model obtained by performing learning of training data including at least a partial region of a three-dimensional medical image. Here, a case will be considered in which a three-dimensional medical image is composed of a plurality of two-dimensional medical images obtained at different positions. At such time, for example, B-scan images are tomographic images on the X-Z plane, and the different positions are in the Y-direction. In this case, the training data or the data input to the learned model may be a three-dimensional medical image constituted by a plurality of two-dimensional medical images for which a misalignment in the X-Z direction was corrected (aligned). Further, in the case of generating a three-dimensional high quality image from a three-dimensional medical image using a learned model, since the processing time will be longer than in the case of a two-dimensional medical image, for example, a configuration may be adopted so as to perform processing at a server that is capable of high-speed processing. In this case, a configuration may be adopted so that medical image data obtained by an imaging apparatus is transmitted from a client to the server, and after processing is performed using a learned model at the server, the resulting data after the processing is transmitted from the server to the client. Note that, the server may be any form of server, such as a cloud server, a FOG server, or an edge server, regardless of the installation location thereof. Further, as methods for performing alignment of a plurality of two-dimensional medical images as described above, the same method may be applied with respect to the method for performing alignment in the X-direction and the method for performing alignment in the Z-direction (depth direction), or the methods that are applied may all be different. In addition, alignment in the same direction may be performed a plurality of times by different methods. For example, a coarse alignment may be performed, and thereafter a precise alignment may be performed. Further, the methods for alignment include, for example, (coarse Z-direction) alignment using a retinal layer boundary obtained by subjecting a tomographic image (B-scan image) to segmentation processing, (precise X-direction or Z-direction) alignment using correlation information (similarity) between a plurality of regions obtained by dividing a tomographic image and a reference image, (X-direction) alignment using a one-dimensional projection image generated for each tomographic image (B scan image), and (X-direction) alignment using a two-dimensional front image. Further, a configuration may be adopted so as to perform precise alignment in sub-pixel units after coarse alignment was performed in pixel units.

Further, the image quality improving engine may be a learned model obtained by performing learning of learned data that includes two-dimensional medical images of a plurality of ranges which differ from each other with respect to at least some of the range in the three-dimensional medical image data of a predetermined site of the subject. For example, the image quality improving engine may be a learned model obtained by performing learning of training data that includes at least a partial region of a first front image in a first depth range of the eye to be examined, and at least a partial region of a second front image for a second depth range in which at least some of the range is different from the first depth range. In other words, the image quality improving engine may be a learned model obtained by performing learning of training data including a plurality of medical images obtained using three-dimensional medical image data of a predetermined site of a subject, that are a plurality of medical images in which the feature values are different from each other. By this means, the image quality improving engine can obtain, for example, a feature value with a high level of abstraction as a learning result with respect to a plurality of feature values that are different from each other. Therefore, for example, even in the case of a medical image having a feature value that is different from the plurality of feature values, if the extracted feature value with a high level of abstraction is within the applicable range, image quality improving can be performed with relatively good accuracy. For example, by using a learned model obtained by performing learning of training data including at least a partial region of a first front image in a first depth range, and at least a partial region of a second front image in a second depth range, a high quality image can be accurately generated from at least a partial region of a third front image in a third depth range with respect to which at least some of the range is different from the first depth range and the second depth range. At such time, for example, the first depth range is a surface layer in which relatively thick blood vessels are distributed, and the second depth range is a deep layer in which relatively thin blood vessels are distributed (or blood vessels are not distributed). Therefore, the feature value of the first front image and the feature value of the second front image are different from each other.

Furthermore, a set of input data and correct answer data (ground truth) included in the training data may be a set of a low quality image and a high quality image. For example, the high quality image may be an image that is obtained by averaging a plurality of low quality images. At such time, by averaging, a site which was not imaged commonly in the plurality of low quality images but which was imaged in any of the low quality images is visualized in some cases in the high quality image. In other words, a site that is not present in a low quality image may appear in the high quality image in some cases. In such a case, there is a possibility that the image quality improving engine will not only obtain a feature value for image quality improving as a learning result, but will also obtain a feature value that will newly generate a nonexistent site. For example, there is a possibility that a false blood vessel will be generated in a region in which, in reality, a blood vessel does not exist, in the high quality image.

Therefore, a plurality of medical images in which differences between sites that are present in the images are comparatively small with respect to each other may be adopted as a set of input data and correct answer data included in the training data. For example, the set of input data and correct answer data may be a set composed of a high quality image to which noise was added and a high quality image, or may be a set composed of a plurality of high quality images to which noises that are different from each other were added. At such time, the noise may be noise of a degree such that a feature value of a site or the like that is present in the image is not lost. Further, a noise pattern with respect to which whether or not to add noise for each pixel is randomly determined may be different for each image. Note that, the magnitude of the added noise may be different for each image. Furthermore, the set may be composed of a plurality of medical images for which the respective numbers of images used for averaging are different from each other. Thus, the image quality improving engine can, for example, accurately obtain a feature value as a learning result. Therefore, by using the image quality improving engine, a high quality image can be accurately generated from an input low quality image. At such time, the input low quality image may be a medical image subjected to processing for reducing various kinds of artifacts as described above. Note that, the reduction processing may also be applied to a high quality image. Further, a configuration may be adopted such that the reduction processing can be selected in accordance with an instruction from the examiner.

In this case, noises that are different from each other may be added to at least a partial region of the plurality of medical images for which feature values are mutually different. For example, if noise that is suitable for a relatively bright medical image is added to a relatively dark medical image, there is a possibility that a site which is present on the relatively dark medical image will be lost. Therefore, for example, the magnitude of noise added to at least a partial region of a relatively dark medical image may be smaller than the magnitude of noise added to at least a partial region of a relatively bright image. Further, the high quality image used as training data may be a high quality image generated by another image quality improving engine.

Further, even if various methods described above are used, in a case where the low quality image is a relatively dark medical image or the like, there is a possibility that a part of a site which was present in the low quality image may be lost from the high quality image because the image quality improving engine regards the part in question as noise or the like. Therefore, for example, a configuration may be adopted so as to obtain a composite image by combining the low quality image and the high quality image at a ratio corresponding to the brightness of the images or the like. Thus, for example, since a site is present in the low quality image even if the relevant site is lost in the high quality image, such a site can be restored in the high quality image.

Further, the high quality image or the composite image or the like may be stored in the storage unit in accordance with an instruction from the examiner. At such time, after the instruction from the examiner to save the high quality image or the composite image or the like, when registering a file name, a file name that includes information (for example, characters) indicating that the image is an image generated by processing using a learned model for improving image quality (image quality improving processing) at any part of the file name (for example, the first part or the last part) may be displayed as a recommended file name in a state in which the file name can be edited according to an instruction from the examiner. Further, when causing the display unit to display a high quality image on various display screens such as the report screen as described above, a display indicating that the image being displayed is a high quality image generated by processing using a learned model for improving image quality may be displayed together with the high quality image. In this case, since a user can easily discern by the relevant display that the displayed high quality image is not the actual image obtained by imaging, misdiagnosis can be reduced and the diagnosis efficiency can be improved. Note that, a display indicating that a high quality image was generated by processing that used a learned model for improving image quality may be of any form as long as it is a display which makes it possible to distinguish between the input image and the high quality image generated by the relevant processing. Further, with regard to processing using various learned models as described above also, and not just processing using a learned model for improving image quality, a display indicating that the result which is being displayed was generated by processing using the relevant kind of learned model may be displayed together with the relevant result. At such time, the display screen such as a report screen may be stored in the storage unit in accordance with an instruction from the examiner. For example, a report screen may be stored in the storage unit as a single image in which high quality images or composite images or the like and a display indicating that these images are high quality images generated by processing using a learned model for improving image quality are displayed side by side. Further, with respect to the display indicating that a high quality image was generated by processing that used a learned model for improving image quality, a display indicating what kind of training data the learned model for improving image quality used when performing learning may be displayed on the display unit. The display in question may include a display of a description of the kinds of input data and correct answer data of the training data, or any display relating to the input data and the correct answer data such as an imaged site included in the correct answer data or the like. Note that, with regard to processing using various learned models as described above also, and not just processing using a learned model for improving image quality, a display indicating what kind of training data the relevant kind of learned model used when performing learning may be displayed on the display unit. Further, a configuration may be adopted so that information (for example, characters) indicating that the image was generated by processing using a learned model for improving image quality may be displayed or stored in a state in which the information is superimposed on the high quality image or composite image or the like. At such time, a place at which the information is superimposed on the image may be any place as long as the place is in a region (for example, at an edge of the image) which does not overlap with a region in which the site of interest or the like that is the imaging target is displayed. Further, a non-overlapping region may be determined, and the information may be superimposed in the determined region.

Further, a configuration may be adopted so that in a case where, as an initial display screen of the report screen, the default setting is set so that the button 3420 enters an active state (image quality improving processing is set to "on"), a report image corresponding to the report screen that includes a high quality image or a composite image or the like is transmitted to a server in accordance with an instruction from the examiner. Further, a configuration may be adopted so that in a case where the default setting is set so that the button 3420 enters an active state, when an examination ends (for example, in a case where the imaging confirmation screen or the preview screen is changed to the report screen in accordance with an instruction from the examiner), a report image corresponding to the report screen that includes a high quality image or a composite image or the like is (automatically) transmitted to a server. At such time, a configuration may be adopted so that a report image generated based on various kinds of settings of the default settings (for example, settings relating to at least one of the depth range for generating an en-face image on the initial display screen of the report screen, whether or not to superimpose an analysis map, whether or not the image is a high quality image, and whether or not to show a display screen for follow-up observation and the like) is transmitted to a server.

Further, among the various learned models described above, an image obtained with a first kind of learned model (for example, a high quality image, an image showing an analysis result such as an analysis map, an image showing an object recognition result, or an image showing a segmentation result) may be input to a second kind of learned model that is different from the first kind. At such time, a configuration may be adopted so that a result (for example, an analysis result, a diagnosis result, an object recognition result or a segmentation result) is generated by processing of the second kind of learned model. Further, among the various learned models described above, an image to be input to a second kind of learned model that is different from a first kind of learned model may be generated from an image input to the first kind of learned model by using a result (for example, an analysis result, a diagnosis result, an object recognition result or a segmentation result) obtained by processing of the first kind of learned model. At such time, there is a high possibility that the generated image is an image that is suitable as an image for processing by the second kind of learned model. Therefore, the accuracy of an image (for example, a high quality image, an image showing an analysis result such as an analysis map, an image showing an object recognition result or an image showing a segmentation result) obtained when the generated image is input to the second kind of learned model can be enhanced. Further, retrieval of similar images utilizing an external database that is stored in a server or the like may be performed using an analysis result or a diagnosis result or the like, as a search key, obtained by processing of the learned models as described above. Note that, in a case where a plurality of images stored in the database are already being managed in a state in which respective feature values of the plurality of images have been attached as supplementary information by machine learning or the like, a similar image search engine (a similar image search model, or a learned model for similar image searching) that utilizes an image itself as a search key may be used.

VARIOUS EMBODIMENTS

Embodiment 1 of the present disclosure relates to a medical image processing apparatus. The medical image processing apparatus includes: an obtaining unit configured to obtain a first image that is an image of a predetermined site of a subject; and an image quality improving unit configured to generate, from the first image, a second image subjected to at least one of noise reduction and contrast enhancement compared to the first image, using an image quality improving engine that includes a machine learning engine.

Embodiment 2 includes the medical image processing apparatus according to Embodiment 1, in which the image quality improving engine includes a machine learning engine for which an image obtained by performing at least one kind of processing among averaging processing, maximum a posteriori processing, smoothing filter processing, gradation conversion processing and noise reduction processing is adopted as training data.

Embodiment 3 includes the medical image processing apparatus according to Embodiment 1, in which the image quality improving engine includes a machine learning engine for which an image imaged with an imaging apparatus with higher performance than an imaging apparatus used for imaging of the first image, or an image obtained by an imaging step including a number of steps that is greater than a number of steps of an imaging step for imaging the first image is adopted as training data.

Embodiment 4 includes the medical image processing apparatus according to any one of Embodiments 1 to 3, and further includes a determining unit configured to determine whether the second image can be generated using the image quality improving engine with respect to the first image.

Embodiment 5 includes the medical image processing apparatus according to Embodiment 4, in which the determining unit performs the determination based on at least one of an imaged site, an imaging system, an imaging angle of view and an image size of the first image.

Embodiment 6 includes the medical image processing apparatus according to Embodiment 4 or 5, in which the image quality improving unit generates the second image in response to an input from an examiner with respect to a determination result obtained by the determining unit.

Embodiment 7 includes the medical image processing apparatus according to any one of Embodiments 1 to 6, in which the image quality improving unit includes a plurality of image quality improving engines which performed learning using different training data from each other.

Embodiment 8 includes the medical image processing apparatus according to Embodiment 7, in which each of the plurality of image quality improving engines performs learning using different training data from each other with respect to at least one of an imaged site, an imaging angle of view, and an image resolution, and the image quality improving unit generates the second image using the image quality improving engine that corresponds to at least one of an imaged site, an imaging angle of view, and an image resolution of the first image.

Embodiment 9 includes the medical image processing apparatus according to Embodiment 7, in which the image quality improving unit generates the second image using the image quality improving engine that corresponds to an instruction of an examiner among the plurality of image quality improving engines.

Embodiment 10 includes the medical image processing apparatus according to Embodiment 7, in which the image quality improving unit generates a plurality of the second images from the first image using the plurality of image quality improving engines, and the medical image processing apparatus outputs at least one image among the plurality of second images in accordance with an instruction of an examiner.

Embodiment 11 includes the medical image processing apparatus according to Embodiment 7, and further includes an evaluating unit configured to evaluate image quality of the second image, in which the image quality improving unit generates a plurality of the second images from the first image using the plurality of image quality improving engines, and the medical image processing apparatus outputs at least one image among the plurality of second images in accordance with an evaluation result obtained by the evaluating unit.

Embodiment 12 includes the medical image processing apparatus according to Embodiment 11, in which the evaluating unit includes a machine learning engine that used an evaluation value obtained by a predetermined evaluation technique as training data, and the medical image processing apparatus outputs the second image for which an evaluation value obtained by the evaluating unit is highest among the plurality of second images.

Embodiment 13 includes the medical image processing apparatus according to any one of Embodiments 1 to 10, and further includes an evaluating unit configured to evaluate image quality of the second image, in which the evaluating unit includes an authenticity evaluating engine that evaluates the authenticity of an image, and the medical image processing apparatus outputs the second image in a case where an output from the authenticity evaluating engine of the evaluating unit is "True".

Embodiment 14 includes the medical image processing apparatus according to Embodiment 13, in which the authenticity evaluating engine includes a machine learning engine that, as training data, uses an image generated by a different image quality improving engine in which the accuracy of image quality improving processing is lower than the image quality improving engine.

Embodiment 15 includes the medical image processing apparatus according to any one of Embodiments 1 to 14, and further includes an estimating unit configured to estimate at least one of an imaged site and an imaged region of the first image.

Embodiment 16 includes the medical image processing apparatus according to Embodiment 15, in which the estimating unit includes a machine learning engine which used an image to which a label of at least one of an imaged site and an imaged region is attached as training data.

Embodiment 17 includes the medical image processing apparatus according any one of Embodiments 1 to 16, in which the image quality improving unit adjusts an image size of the first image to an image size which the image quality improving engine is capable of handling and inputs the first image for which the image size was adjusted to the image quality improving engine, and generates the second image by adjusting a size of an output image from the image quality improving engine to an original image size of the first image.

Embodiment 18 includes the medical image processing apparatus according any one of Embodiments 1 to 17, in which the image quality improving unit: adjusts an image size of the first image so that a resolution of the first image becomes a predetermined resolution; with respect to the first image for which the image size was adjusted, inputs an image obtained by performing padding so that the adjusted image size becomes an image size which the image quality improving engine is capable of handling to the image quality improving engine; with respect to an output image from the image quality improving engine, performs trimming so as to trim only a region corresponding to a region in which padding was performed; and adjusts an image size of the image on which trimming was performed to an original image size of the first image to generate the second image.

Embodiment 19 includes the medical image processing apparatus according to any one of Embodiments 1 to 18, in which the image quality improving unit: divides the first image into a plurality of third images of a predetermined image size; inputs the plurality of third images to the image quality improving engine to generate a plurality of fourth images; and integrates the plurality of fourth images to generate the second image.

Embodiment 20 includes the medical image processing apparatus according to any one of Embodiments 1 to 19, in which the image quality improving unit: divides the first image with three dimensions into a plurality of two-dimensional images or a plurality of one-dimensional images and inputs the plurality of two-dimensional images or the plurality of one-dimensional images into the image quality improving engine; and integrates a plurality of output images from the image quality improving engine to generate the second image.

Embodiment 21 includes the medical image processing apparatus according to any one of Embodiments 1 to 20, in which the image quality improving unit includes a plurality of the image quality improving engines, and divides the first image with three dimensions into a plurality of two-dimensional images or a plurality of one-dimensional images, generates a plurality of second images from the plurality of two-dimensional images or the plurality of one-dimensional images by using the plurality of image quality improving engines in parallel, and integrates the plurality of second images to generate the second image with three dimensions.

Embodiment 22 includes the medical image processing apparatus according to any one of Embodiments 1 to 21, in which the image quality improving unit generates, as the second image, an image that, in comparison to the first image, is subjected to at least one of noise reduction and contrast enhancement, and is also subjected to at least one of image size enlargement and spatial resolution increasing.

Embodiment 23 includes the medical image processing apparatus according to any one of Embodiments 1 to 22, and further includes a display controlling unit configured to display the second image on a display unit.

Embodiment 24 includes the medical image processing apparatus according to Embodiment 23, in which the display controlling unit causes the second image to be displayed on the display unit in accordance with an instruction of an examiner.

Embodiment 25 includes the medical image processing apparatus according to Embodiment 23 or 24, in which the display controlling unit causes a display indicating that the second image is an image generated by the image quality improving engine to be displayed together with the second image on the display unit.

Embodiment 26 includes the medical image processing apparatus according to any one of Embodiments 23 to 25, in which the display controlling unit causes the second image to be displayed on the display unit, and the medical image processing apparatus outputs the second image in accordance with an input from an examiner with respect to the displayed second image.

Embodiment 27 includes the medical image processing apparatus according to any one of Embodiments 23 to 26, and further includes an analyzing unit configured to perform image analysis of the second image, in which the display controlling unit causes an analysis result obtained by the analyzing unit to be displayed on the display unit.

Embodiment 28 includes the medical image processing apparatus according to any one of Embodiments 1 to 27, in which the image quality improving unit generates the second image that is one image, from a plurality of the first images.

Embodiment 29 includes the medical image processing apparatus according to any one of Embodiments 1 to 28, in which the first image is an image generated using a plurality of images of a predetermined site of a subject.

Embodiment 30 includes the medical image processing apparatus according to any one of Embodiments 1 to 29, in which the image quality improving unit generates a plurality of the second images, and averages the plurality of second images.

Embodiment 31 includes the medical image processing apparatus according to any one of Embodiments 1 to 30, in which the predetermined site is an eye to be examined.

Embodiment 32 includes the medical image processing apparatus according to any one of Embodiments 1 to 31, in which the obtaining unit obtains the first image from an imaging apparatus.

Embodiment 33 includes the medical image processing apparatus according to any one of Embodiments 1 to 31, in which the obtaining unit obtains data of the predetermined site of a subject from an imaging apparatus, and obtains the first image based on the data.

Embodiment 34 includes the medical image processing apparatus according to any one of Embodiments 1 to 31, in which the obtaining unit obtains the first image from an image management system.

Embodiment 35 includes the medical image processing apparatus according to any one of Embodiments 1 to 34, in which the image quality improving engine does not use the second image as training data.

Embodiment 36 relates to a medical image processing method. The medical image processing method includes: obtaining a first image that is an image of a predetermined site of a subject; and generating, from the first image, a second image subjected to at least one of noise reduction and contrast enhancement compared to the first image, using an image quality improving engine that includes a machine learning engine.

Embodiment 37 relates to a program. When the program is executed by a processor, the program causes the processor to execute respective steps of the medical image processing method according to Embodiment 36.

Additional Embodiment 1 of the present disclosure relates to a medical image processing apparatus. The medical image processing apparatus includes: an obtaining unit configured to obtain a first image that is a motion contrast front image corresponding to at least a partial depth range of three-dimensional motion contrast data of an eye to be examined; and an image quality improving unit configured to generate, from the first image, a second image subjected to image quality improving compared to the first image using an image quality improving engine including a machine learning engine.

Additional Embodiment 2 includes the medical image processing apparatus according to additional Embodiment 1, in which the image quality improving engine includes a machine learning engine obtained by performing learning of training data obtained using an image obtained by subjecting a plurality of pieces of motion contrast data of an eye to be examined to averaging processing.

Additional Embodiment 3 includes the medical image processing apparatus according to additional Embodiment 1, in which the image quality improving engine includes a machine learning engine obtained using training data including an image obtained by OCTA imaging performed by an OCT imaging apparatus with higher performance than an OCT imaging apparatus used for OCTA imaging of the first image, or an image obtained by an OCTA imaging step that includes a greater number of steps than an OCTA imaging step used for obtaining the first image.

Additional Embodiment 4 includes the medical image processing apparatus according to any one of additional Embodiments 1 to 3, in which the image quality improving unit generates the second image by dividing the first image into a plurality of two-dimensional images and inputting the plurality of two-dimensional images into the image quality improving engine, and integrating a plurality of output images from the image quality improving engine.

Additional Embodiment 5 includes the medical image processing apparatus according to additional Embodiment 4, in which the image quality improving engine includes a machine learning engine obtained using training data including an image pair having a corresponding positional relationship to each other, and the image quality improving unit divides the first image into a plurality of two-dimensional images having an image size corresponding to an image size of the image pair and inputs the plurality of two-dimensional images to the image quality improving engine.

Additional Embodiment 6 includes the medical image processing apparatus according to additional Embodiment 4 or 5, in which the image quality improving engine includes a machine learning engine obtained using training data that, with respect to an image and a region including an outer periphery of the image, includes images of a plurality of partial regions set so that parts of partial regions that are adjacent overlap with each other.

Additional Embodiment 7 includes the medical image processing apparatus according to any one of additional Embodiments 1 to 6, in which the image quality improving engine includes a machine learning engine obtained by performing learning of training data obtained using an image obtained by adding noise to a motion contrast front image of an eye to be examined.

Additional Embodiment 8 includes the medical image processing apparatus according to any one of additional Embodiments 1 to 7, in which the image quality improving engine includes a machine learning engine obtained by performing learning of training data obtained using an image obtained by adding noise to an image obtained by performing averaging processing of a plurality of pieces of motion contrast data of an eye to be examined.

Additional Embodiment 9 includes the medical image processing apparatus according to any one of additional Embodiments 1 to 8, in which the image quality improving engine includes a machine learning engine obtained by performing learning of training data obtained using an image pair obtained by adding noise of different patterns from each other to an image obtained by performing averaging processing of a plurality of pieces of motion contrast data of an eye to be examined.

Additional Embodiment 10 includes the medical image processing apparatus according to any one of additional Embodiments 1 to 9, and further includes a wide-angle image generating unit configured to generate a wide-angle image using a plurality of the second images obtained from a plurality of the first images, the plurality of first images being obtained by performing OCTA imaging of different positions of an eye to be examined so that partial regions of motion contrast front images that are adjacent overlap with each other.

Additional Embodiment 11 includes the medical image processing apparatus according to any one of additional Embodiments 1 to 10, in which the image quality improving engine includes a machine learning engine obtained by learning a plurality of motion contrast front images corresponding to a plurality of depth ranges of an eye to be examined as training data, and the obtaining unit obtains a motion contrast front image corresponding to the at least partial depth range set in accordance with an instruction from an examiner as the first image.

Additional Embodiment 12 includes the medical image processing apparatus according to any one of additional Embodiments 1 to 11, and further includes a determining unit configured to determine whether or not the second image can be generated by using the image quality improving engine with respect to the first image, in which the determining unit performs the determination based on at least one of an imaged site, an imaging system, an imaging angle of view and an image size of the first image.

Additional Embodiment 13 includes the medical image processing apparatus according to any one of additional Embodiments 1 to 12, in which the image quality improving unit includes a plurality of image quality improving engines which performed learning using different training data from each other, and in which each of the plurality of image quality improving engines performs learning using different training data from each other with respect to at least one of an imaged site, an imaging angle of view, and an image resolution, and the image quality improving unit generates the second image using the image quality improving engine that corresponds to at least one of an imaged site, an imaging angle of view, and an image resolution of the first image.

Additional Embodiment 14 includes the medical image processing apparatus according to any one of additional Embodiments 1 to 12, in which the image quality improving unit includes a plurality of image quality improving engines which performed learning using different training data from each other, and the image quality improving unit generates the second image using the image quality improving engine that corresponds to an instruction of an examiner among the plurality of image quality improving engines.

Additional Embodiment 15 includes the medical image processing apparatus according to any one of additional Embodiments 1 to 12, in which the image quality improving unit includes a plurality of image quality improving engines which performed learning using different training data from each other, and the image quality improving unit generates a plurality of the second images from the first image using the plurality of image quality improving engines, and the medical image processing apparatus outputs at least one image among the plurality of second images in accordance with an instruction of an examiner.

Additional Embodiment 16 includes the medical image processing apparatus according to any one of additional Embodiments 1 to 12, and which further includes an evaluating unit configured to evaluate image quality of the second image, in which the image quality improving unit includes a plurality of image quality improving engines that performed learning using different training data from each other, the image quality improving unit generates a plurality of the second images from the first image using the plurality of image quality improving engines, and the medical image processing apparatus outputs at least one image among the plurality of second images in accordance with an evaluation result obtained by the evaluating unit.

Additional Embodiment 17 includes the medical image processing apparatus according to additional Embodiment 16, in which the evaluating unit includes a machine learning engine that used an evaluation value obtained by a predetermined evaluation technique as training data, and the medical image processing apparatus outputs the second image for which an evaluation value obtained by the evaluating unit is highest among the plurality of second images.

Additional Embodiment 18 includes the medical image processing apparatus according to any one of additional Embodiments 1 to 17, in which the image quality improving unit generates the second image by adjusting an image size of the first image to an image size which the image quality improving engine is capable of handling, inputting the first image for which the image size was adjusted to the image quality improving engine, and adjusting a size of an output image from the image quality improving engine to an original image size of the first image.

Additional Embodiment 19 includes the medical image processing apparatus according to any one of additional Embodiments 1 to 18, in which the image quality improving unit generates the second image by adjusting an image size of the first image so that a resolution of the first image becomes a predetermined resolution, with respect to the first image for which the image size was adjusted, inputting, to the image quality improving engine, an image obtained by performing padding so that the image size which was adjusted becomes an image size which the image quality improving engine is capable of handling, with respect to an output image from the image quality improving engine, performing trimming so as to trim only a region corresponding to a region in which padding was performed, and adjusting an image size of the image on which trimming was performed to an original image size of the first image.

Additional Embodiment 20 includes the medical image processing apparatus according to any one of additional Embodiments 1 to 19, in which the image quality improving unit generates the second image by dividing the first image into a plurality of third images of a predetermined image size, inputting the plurality of third images to the image quality improving engine to generate a plurality of fourth images, and integrating the plurality of fourth images.

Additional Embodiment 21 includes the medical image processing apparatus according to any one of additional Embodiments 1 to 20, in which the image quality improving unit includes a plurality of the image quality improving engines, and generates the second image by dividing the first image into a plurality of two-dimensional images, generating a plurality of second images from the plurality of two-dimensional images by using the plurality of image quality improving engines in parallel, and integrating the plurality of second images.

Additional Embodiment 22 includes the medical image processing apparatus according to any one of additional Embodiments 1 to 21, in which the image quality improving unit generates, as the second image, an image that, in comparison to the first image, is subjected to at least one of noise reduction and contrast enhancement, and is also subjected to at least one of image size enlargement and spatial resolution increasing.

Additional Embodiment 23 includes the medical image processing apparatus according to any one of additional Embodiments 1 to 22, and further includes a display controlling unit configured to display the second image on a display unit.

Additional Embodiment 24 includes the medical image processing apparatus according to additional Embodiment 23, in which the display controlling unit causes the second image to be displayed on the display unit in accordance with an instruction of an examiner.

Additional Embodiment 25 includes the medical image processing apparatus according to additional Embodiment 23 or 24, in which the display controlling unit causes a display indicating that the second image is an image generated by the image quality improving engine to be displayed together with the second image on the display unit.

Additional Embodiment 26 includes the medical image processing apparatus according to any one of additional Embodiments 23 to 25, in which the display controlling unit causes the second image to be displayed on the display unit, and the medical image processing apparatus outputs the second image in accordance with an input from an examiner with respect to the displayed second image.

Additional Embodiment 27 includes the medical image processing apparatus according to any one of additional Embodiments 23 to 26, and further includes an analyzing unit configured to perform image analysis of the second image, in which the display controlling unit causes an analysis result relating to a blood vessel in the second image to be displayed on the display unit.

Additional Embodiment 28 includes the medical image processing apparatus according to any one of additional Embodiments 1 to 27, in which the image quality improving unit generates the second image that is one image, from a plurality of the first images.

Additional Embodiment 29 includes the medical image processing apparatus according to any one of additional Embodiments 1 to 28, in which the first image is one piece of motion contrast front image generated using a plurality of motion contrast front images of an eye to be examined.

Additional Embodiment 30 includes the medical image processing apparatus according to any one of additional Embodiments 1 to 29, in which the image quality improving unit generates a plurality of the second images, and averages the plurality of second images.

Additional Embodiment 31 includes the medical image processing apparatus according to any one of additional Embodiments 1 to 30, in which the obtaining unit obtains the first image from an OCT imaging apparatus.

Additional Embodiment 32 includes the medical image processing apparatus according to any one of additional Embodiments 1 to 30, in which the obtaining unit obtains three-dimensional motion contrast data of an eye to be examined from an OCT imaging apparatus, and generates the first image that is the motion contrast front image using data of at least a partial range in a depth direction of an eye to be examined with respect to the three-dimensional motion contrast data.

Additional Embodiment 33 includes the medical image processing apparatus according to any one of additional Embodiments 1 to 30, in which the obtaining unit obtains the first image from an image management system.

Additional Embodiment 34 includes the medical image processing apparatus according to any one of additional Embodiments 1 to 33, in which the image quality improving engine does not use the second image as training data.

Additional Embodiment 35 relates to a medical image processing method. The medical image processing method includes: obtaining a first image that is a motion contrast front image corresponding to at least a partial depth range of three-dimensional motion contrast data of an eye to be examined; and generating, from the first image, a second image subjected to image quality improving compared to the first image using an image quality improving engine including a machine learning engine.

Additional Embodiment 36 relates to a program. When the program is executed by a processor, the program causes the processor to execute respective steps of the medical image processing method according to Additional Embodiment 35.

Other Embodiment 1 of the present disclosure relates to a medical image processing apparatus. The medical image processing apparatus includes: an obtaining unit configured to obtain a first image that is a medical image of a predetermined site of a subject; an image quality improving unit configured to generate, from the first image, a second image in which image quality is improved compared to the first image, using an image quality improving engine including a machine learning engine; and a display controlling unit configured to cause a composite image obtained by combining the first image and the second image according to a ratio obtained using information relating to at least a partial region of the first image to be displayed on a display unit.

Other Embodiment 2 includes the medical image processing apparatus according to other Embodiment 1, in which a ratio for combining the first image and the second image is obtained by using a pixel value in at least a partial region of the first image as the information.

Other Embodiment 3 includes the medical image processing apparatus according to other Embodiment 1 or 2, in which a ratio for combining the first image and the second image is obtained by using a differential value between pixel values in at least partial regions corresponding to each other in the first image and the second image as the information.

Other Embodiment 4 includes the medical image processing apparatus according to any one of other Embodiments 1 to 3, in which a ratio for combining the first image and the second image is configured to be changeable in accordance with an instruction from an examiner.

Other Embodiment 5 includes the medical image processing apparatus according to any one of other Embodiments 1 to 4, in which a ratio for combining the first image and the second image is determined based on the information by using a learned model obtained by learning using training data in which a medical image is adopted as input data, and information relating to a ratio for combining the medical image and a medical image obtained by subjecting the medical image to image quality improving is adopted as correct answer data.

Other Embodiment 6 includes the medical image processing apparatus according to any one of other Embodiments 1 to 5, in which the image quality improving engine includes a machine learning engine obtained using training data in which noise is added to at least a partial region of a medical image.

Other Embodiment 7 includes the medical image processing apparatus according to any one of other Embodiments 1 to 6, in which the image quality improving engine includes a machine learning engine obtained by using training data in which noise corresponding to a state of at least a partial region of a medical image is added to the at least partial region.

Other Embodiment 8 relates to a medical image processing apparatus. The medical image processing apparatus includes: an obtaining unit configured to obtain a first image that is a medical image of a predetermined site of a subject; and an image quality improving unit configured to generate, from the first image, a second image in which image quality is improved compared to the first image, using an image quality improving engine including a machine learning engine obtained using training data in which noise corresponding to a state of at least a partial region of a medical image is added to the at least partial region.

Other Embodiment 9 includes the medical image processing apparatus according to any one of other Embodiments 1 to 8, in which the image quality improving engine includes a machine learning engine obtained using training data in which noise of a size corresponding to a pixel value of at least a partial region of a medical image is added to the at least partial region.

Other Embodiment 10 includes the medical image processing apparatus according to any one of other Embodiments 1 to 9, in which the image quality improving engine includes a machine learning engine obtained using training data that includes a plurality of medical images to which noise of different patterns from each other is added.

Other Embodiment 11 includes the medical image processing apparatus according to any one of other Embodiments 1 to 10, in which the image quality improving engine includes a machine learning engine obtained using training data including, as an image pair, a plurality of medical images obtained by adding noises of different patterns from each other to a medical image obtained by averaging processing.

Other Embodiment 12 includes the medical image processing apparatus according to any one of other Embodiments 1 to 11, and further includes a specifying unit configured to specify a partial depth range in a depth range of the predetermined site in three-dimensional medical image data of the predetermined site in accordance with an instruction from an examiner, in which the obtaining unit obtains a front image corresponding to the specified partial depth range as the first image, and the image quality improving engine includes a machine learning engine obtained using training data that includes a plurality of front images corresponding to a plurality of depth ranges of a predetermined site of a subject.

Other Embodiment 13 relates to a medical image processing apparatus. The medical image processing apparatus includes: a specifying unit configured to specify a partial depth range in a depth range of a predetermined site of a subject in three-dimensional medical image data of the predetermined site in accordance with an instruction from an examiner; an obtaining unit configured to obtain a first image that is a front image of the predetermined site that corresponds to the specified partial depth range, using the three-dimensional data; and an image quality improving unit configured to generate, from the first image, a second image in which image quality is improved compared to the first image, using a machine learning engine obtained using training data that includes a plurality of front images corresponding to a plurality of depth ranges of a predetermined site of a subject.

Other Embodiment 14 includes the medical image processing apparatus according to other Embodiment 12 or 13, in which the image quality improving engine includes a machine learning engine obtained using training data including the plurality of front images to which noise of different sizes is added with respect to each of at least two depth ranges among the plurality of depth ranges.

Other Embodiment 15 includes the medical image processing apparatus according to any one of other Embodiments 12 to 14, and further includes a wide-angle image generating unit configured to generate a wide-angle image using a plurality of the second images obtained from a plurality of the first images, the plurality of first images being obtained by imaging different positions of the predetermined site in a direction that intersects with a depth direction of the predetermined site so that partial regions of a plurality of front images that are adjacent to each other which correspond to the specified partial depth range overlap.

Other Embodiment 16 includes the medical image processing apparatus according to any one of other Embodiments 1 to 15, in which the image quality improving engine includes a machine learning engine obtained using training data including an image obtained by OCTA imaging performed by an OCT imaging apparatus with higher performance than an OCT imaging apparatus used for OCTA imaging of the first image, or an image that is obtained by an OCTA imaging step that includes a greater number of steps than an OCTA imaging step used for obtaining the first image.

Other Embodiment 17 includes the medical image processing apparatus according to any one of other Embodiments 1 to 16, in which the image quality improving unit generates the second image by dividing the first image into a plurality of two-dimensional images and inputting the plurality of two-dimensional images into the image quality improving engine, and integrating a plurality of output images from the image quality improving engine.

Other Embodiment 18 includes the medical image processing apparatus according to other Embodiment 17, in which the image quality improving engine includes a machine learning engine obtained using training data including a plurality of medical images having a corresponding positional relationship to each other as an image pair, and the image quality improving unit divides the first image into the plurality of two-dimensional images with an image size corresponding to an image size of the image pair and inputs the plurality of two-dimensional images to the image quality improving engine.

Other Embodiment 19 includes the medical image processing apparatus according to other Embodiment 17 or 18, in which the image quality improving engine includes a machine learning engine obtained using training data that, with respect to a medical image and a region including an outer periphery of the medical image, includes images of a plurality of partial regions set so that parts of partial regions that are adjacent overlap with each other.

Other Embodiment 20 includes the medical image processing apparatus according to any one of other Embodiments 1 to 19, in which the image quality improving engine includes a machine learning engine obtained using training data that includes a medical image obtained by averaging processing.

Other Embodiment 21 relates to a medical image processing method. The medical image processing method includes: obtaining a first image that is a medical image of a predetermined site of a subject; generating, from the first image, a second image in which image quality is improved compared to the first image, using an image quality improving engine including a machine learning engine; and causing a composite image obtained by combining the first image and the second image according to a ratio obtained using information relating to at least a partial region of the first image to be displayed on a display unit.

Other Embodiment 22 relates to a medical image processing method. The medical image processing method includes: obtaining a first image that is a medical image of a predetermined site of a subject; and generating, from the first image, a second image in which image quality is improved compared to the first image, using an image quality improving engine including a machine learning engine obtained using training data in which noise corresponding to a state of at least a partial region of a medical image is added to the at least partial region.

Other Embodiment 23 relates to a medical image processing method. The medical image processing method includes: specifying a partial depth range in a depth range of a predetermined site of a subject in three-dimensional medical image data of the predetermined site in accordance with an instruction from an examiner; obtaining a first image that is a front image of the predetermined site that corresponds to the specified partial depth range, using the three-dimensional data; and generating, from the first image, a second image in which image quality is improved compared to the first image, using a machine learning engine obtained using training data that includes a plurality of front images corresponding to a plurality of depth ranges of a predetermined site of a subject.

Other Embodiment 24 relates to a program. When the program is executed by a processor, the program causes the processor to execute respective steps of the medical image processing method according to any one of other Embodiments 21 to 23.

According to one of the embodiments, modifications and Embodiments that are described above, an image can be generated that is more suitable for image diagnosis than an image generated according to the conventional technology.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical image processing apparatus comprising at least one of (a) one or more processors connected to one or more memories storing a program including instructions executed by the one or more processors and (b) circuitry configured to function as:

an obtaining unit configured to obtain a first image that is an image of a predetermined site of an eye to be examined; and a display controlling unit configured to control a display unit to display one of the first image and a second image generated by inputting the first image into an image quality improving engine including a machine learning engine as an input image of the image quality improving engine wherein:

in a case where an imaging condition of the first image is an imaging angle with which an image quality improvement is capable of being performed by the image quality improving engine, the display unit is controlled to display the second image; and in a case where the imaging condition of the first image is not the imaging angle with which the image quality improvement is capable of being performed by the image quality improving engine, the display unit is controlled to display the first image.

2. The medical image processing apparatus according to claim 1, wherein:

in a case where an imaging condition of the first image is the imaging angle with which the image quality improvement is capable of being performed by the image quality improving engine, the display unit is controlled to change the display of the first image into the display of the second image in accordance with an instruction from an operator.

3. The medical image processing apparatus according to claim 1, wherein:

in a case where an imaging condition of the first image is the imaging angle with which the image quality improvement is capable of being performed by the image quality improving engine, the display unit is controlled to change the display of the first image into the display of the second image in accordance with an instruction of a button on a user interface displayed on the display unit.

4. The medical image processing apparatus according to claim 1, wherein:

the first image is an image included in a moving image of the predetermined site of the eye to be examined; and the second image is sequentially generated.

5. The medical image processing apparatus according to claim 1, wherein:

the image quality improving engine including a machine learning engine obtained using an OCTA image as training data;

the first image is an OCTA image; and an OCTA image is a motion contrast image indicating temporal change of the predetermined site, the motion contrast image obtained from an imaging result obtained by repeatedly imaging a same location.

6. The medical image processing apparatus according to claim 5, wherein:

the image quality improving engine includes a machine learning engine for which an OCTA image obtained by performing averaging process is adopted as training data.

7. The medical image processing apparatus according to claim 5, wherein:

the display unit is controlled to display an analysis result obtained by performing an image analysis relating to blood vessel density measurement on the second image in accordance with an instruction from an operator.

8. The medical image processing apparatus according to claim 1, wherein:

the second image has a higher image quality than the first image.

9. The medical image processing apparatus according to claim 1, wherein:

the second image has at least one of lower noise and higher contrast than the first image.

10. The medical image processing apparatus according to claim 1, wherein:

input data of training data of the image quality improving engine includes an image based on one or more images of an eye to be examined, and output data of the training data includes an image based on images of an eye to be examined which are more than the one or more images of the eye to be examined.

11. The medical image processing apparatus according to claim 1, wherein:

the second image is generated using an image quality improving engine selected in accordance with an imaging condition corresponding to the first image from among a plurality of image quality improving engines, and each of the plurality of image quality engines obtained by using different training data from each other with respect to imaging condition.

12. The medical image processing apparatus according to claim 1, wherein:

in a case where imaging conditions of the first image are an imaging system according to OCTA and the imaging angle with which the image quality improvement is capable of being performed by the image quality improving engine as imaging conditions with which the image quality improvement is capable of being performed by the image quality improving engine, the display unit is controlled to display the second image.

13. The medical image processing apparatus according to claim 1, wherein:

the image quality improving engine further includes a machine learning engine obtained using an OCT image as training data; and in a case where the imaging condition of the first image is an imaging system according to OCT as an imaging condition with which the image quality improvement is capable of being performed by the image quality improving engine, the display unit is controlled to display the second image.

14. An optical coherence tomography apparatus comprising:

an imaging unit arranged to image an eye to be examined; and the medical image processing apparatus according to claim 1.

15. A medical image processing method comprising:

obtaining a first image that is an image of a predetermined site of an eye to be examined; and controlling a display unit to display one of the first image and a second image generated by inputting the first image into an image quality improving engine including a machine learning engine as an input image of the image quality improving engine, wherein:

in a case where an imaging condition of the first image is an imaging angle with which an image quality improvement is capable of being performed by the image quality improving engine, the display unit is controlled to display the second image; and in a case where the imaging condition of the first image is not the imaging angle with which the image quality improvement is capable of being performed by the image quality improving engine, the display unit is controlled to display the first image.

16. A non-transitory computer-readable medium having stored thereon a program for causing, when executed by a processor, the processor to execute respective steps of the medical image processing method according to claim 15.

* * * * *